United States Patent
Marathi et al.

(10) Patent No.: US 9,216,150 B2
(45) Date of Patent: *Dec. 22, 2015

(54) PH DEPENDENT CARRIERS FOR TARGETED RELEASE OF PHARMACEUTICALS ALONG THE GASTROINTESTINAL TRACT, COMPOSITIONS THEREFROM, AND MAKING AND USING SAME

(71) Applicant: PLX PHARMA INC., Houston, TX (US)

(72) Inventors: Upendra K. Marathi, Houston, TX (US); Susann Edler Childress, Houston, TX (US); Shaun L. Gammill, Houston, TX (US); Robert W. Strozier, Houston, TX (US)

(73) Assignee: PLx Pharma Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/908,233

(22) Filed: Jun. 3, 2013

(65) Prior Publication Data

US 2014/0094439 A1    Apr. 3, 2014

Related U.S. Application Data

(63) Continuation of application No. 13/631,963, filed on Sep. 29, 2012.

(60) Provisional application No. 61/540,699, filed on Sep. 29, 2011.

(51) Int. Cl.
*A61K 31/192* (2006.01)
*A61K 31/196* (2006.01)
(Continued)

(52) U.S. Cl.
CPC ............. *A61K 9/0002* (2013.01); *A61K 9/4858* (2013.01); *A61K 31/192* (2013.01);
(Continued)

(58) Field of Classification Search
CPC . A61K 31/192; A61K 31/196; A61K 31/405; A61K 31/60; A61K 31/616; A61K 45/06; A61K 47/12; A61K 47/14; A61K 47/24; A61K 9/002; A61K 9/4858
See application file for complete search history.

(56) References Cited

U.S. PATENT DOCUMENTS 4,079,131 A   3/1978   Lin et al.
4,079,132 A   3/1978   Lin et al.
(Continued)

FOREIGN PATENT DOCUMENTS

EP      51833 A1      5/1982
EP    0 287 036 A2   10/1988
(Continued)

OTHER PUBLICATIONS

Chowdhury et al. (Bangladesh J Sci Ind Res. 2007, 42(3), 311-316).*
(Continued)

*Primary Examiner* — Ernst V Arnold
(74) *Attorney, Agent, or Firm* — Foley & Lardner LLP

(57) ABSTRACT

Novel drug carriers capable of targeted and/or pH dependent release of biologically active agents into selected pH environments including the gastrointestinal (GI), ophthalmic, urinary, or reproductive tracts. Unexpectedly, carriers including free fatty acids (FFA) are able to deliver biologically active agents to various pH environments. Such targeted delivery is tailorable and useful for active agents that are: (a) injurious to the upper GI tract (esophagus, stomach, and duodenum), (b) acid labile, (c) impermeable/insoluble compounds in GI fluids, (d) susceptible to first pass metabolism, and/or (e) cause stomach irritation, upset, or dyspepsia.

16 Claims, 20 Drawing Sheets

Gastrointestinal Hemoglobin After Treatment

(51) Int. Cl.

| | | |
|---|---|---|
| A61K 31/405 | (2006.01) | |
| A61K 31/60 | (2006.01) | |
| A61K 31/616 | (2006.01) | |
| A61K 45/06 | (2006.01) | |
| A61K 47/12 | (2006.01) | |
| A61K 47/14 | (2006.01) | |
| A61K 9/00 | (2006.01) | |
| A61K 47/24 | (2006.01) | |
| A61K 9/48 | (2006.01) | |

(52) U.S. Cl.
CPC ............ *A61K31/196* (2013.01); *A61K 31/405* (2013.01); *A61K 31/60* (2013.01); *A61K 31/616* (2013.01); *A61K 45/06* (2013.01); *A61K 47/12* (2013.01); *A61K 47/14* (2013.01); *A61K 47/24* (2013.01)

(56) References Cited

U.S. PATENT DOCUMENTS

| | | | |
|---|---|---|---|
| 4,309,420 A | 1/1982 | Ghyczy et al. | |
| 4,332,795 A | 6/1982 | Ghyczy et al. | |
| 4,369,182 A | 1/1983 | Ghyczy et al. | |
| 4,378,354 A | 3/1983 | Ghyczy et al. | |
| 4,421,747 A | 12/1983 | Ghyczy et al. | |
| 4,474,798 A * | 10/1984 | Inagi et al. | 514/420 |
| 4,684,632 A | 8/1987 | Schulz et al. | |
| 4,687,762 A | 8/1987 | Fukushima et al. | |
| 4,849,227 A | 7/1989 | Cho | |
| 4,918,063 A | 4/1990 | Lichtenberger | |
| 4,950,656 A | 8/1990 | Lichtenberger | |
| 5,032,585 A | 7/1991 | Lichtenberger | |
| 5,043,329 A | 8/1991 | Lichtenberger | |
| 5,059,626 A | 10/1991 | Park et al. | |
| 5,091,188 A | 2/1992 | Haynes | |
| 5,110,606 A | 5/1992 | Geyer et al. | |
| 5,145,684 A | 9/1992 | Liversidge et al. | |
| 5,154,930 A | 10/1992 | Popescu et al. | |
| 5,213,804 A | 5/1993 | Martin et al. | |
| 5,314,909 A | 5/1994 | Dollerup | |
| 5,505,960 A | 4/1996 | Lucchetti et al. | |
| 5,552,160 A | 9/1996 | Liversidge et al. | |
| 5,603,959 A * | 2/1997 | Horrobin et al. | 424/490 |
| 5,763,422 A | 6/1998 | Lichtenberger et al. | |
| 5,807,541 A | 9/1998 | Aberg et al. | |
| 5,891,466 A * | 4/1999 | Yesair | 424/450 |
| 5,916,591 A | 6/1999 | Bierdel-Willkommen et al. | |
| 5,942,248 A * | 8/1999 | Barnwell | 424/457 |
| 5,955,451 A | 9/1999 | Lichtenberger | |
| 6,045,821 A | 4/2000 | Garrity et al. | |
| 6,096,336 A | 8/2000 | Cao et al. | |
| 6,096,338 A | 8/2000 | Lacy et al. | |
| 6,120,800 A | 9/2000 | Forsesen et al. | |
| 6,248,363 B1 | 6/2001 | Patel et al. | |
| 6,569,463 B2 | 5/2003 | Patel et al. | |
| 6,759,057 B1 | 7/2004 | Weiner et al. | |
| 6,923,988 B2 | 8/2005 | Patel et al. | |
| 7,374,779 B2 | 5/2008 | Chen et al. | |
| 7,473,432 B2 | 1/2009 | Cevc et al. | |
| 2002/0035264 A1 | 3/2002 | Karali et al. | |
| 2003/0219461 A1 | 11/2003 | Britten et al. | |
| 2004/0077604 A1 | 4/2004 | Lichtenberger | |
| 2004/0109894 A1 | 6/2004 | Shefer et al. | |
| 2004/0146537 A1 | 7/2004 | Radhakrishnan et al. | |
| 2005/0147659 A1 | 7/2005 | Carli et al. | |
| 2006/0100263 A1* | 5/2006 | Basile et al. | 514/412 |
| 2006/0210622 A1 | 9/2006 | Pace et al. | |
| 2007/0154559 A1 | 7/2007 | Pai et al. | |
| 2008/0260819 A1 | 10/2008 | Fleming | |
| 2010/0136105 A1 | 6/2010 | Chen et al. | |
| 2011/0034568 A1 | 2/2011 | Lichtenberger | |
| 2011/0065677 A1 | 3/2011 | Lichtenberger | |
| 2011/0071118 A1 | 3/2011 | Lichtenberger | |

FOREIGN PATENT DOCUMENTS

| | | | | |
|---|---|---|---|---|
| EP | 0 407 815 A2 | 1/1991 | | |
| EP | 1158959 A1 | 12/2001 | | |
| GB | WO 9206680 | * | 4/1992 | ............... A61K 9/48 |
| JP | 5589225 | | 7/1980 | |
| JP | 57108021 A | | 7/1982 | |
| JP | 3176425 A | | 7/1991 | |
| WO | 9622780 A | | 8/1996 | |
| WO | 9813073 A2 | | 4/1998 | |
| WO | 0002554 A2 | | 1/2000 | |
| WO | 0022908 A3 | | 4/2000 | |
| WO | 02085414 A2 | | 10/2002 | |
| WO | WO 02/083099 | * | 10/2002 | |
| WO | WO 2008/025819 A2 | | 3/2008 | |
| WO | WO 2008/068276 A1 | | 6/2008 | |
| WO | 2011082384 A2 | | 7/2011 | |

OTHER PUBLICATIONS

Abstract of JP01313884 published Jul. 31, 1991. 2 pages.*
Phosal® 35 SB data sheet (Feb. 2007) 1 page.*
Pathan et al. (TJPR 2009; 8(2):173-179).*
Stomach pH [online] retrieved on Aug. 27, 2014 from: http://chemistry.about.com/b/2013/07/08/what-is-the-ph-of-the-stomach.htm 1 page.*
Hollander eta l. (Chapter 10 in: Gastric Cytoprotection. 1989:187-195).*
Tarnawski et al. (Abstract of: Clin Invest Med. 1987; 10(3):132-5).*
Mandel et al. (Vet Pathol. 1994. 31:679-688).*
Lichtenberger et a. (Science 1983. 219(4590):1327-1329).*
Lichtenberger et al. (British Journal of Pharmacology 2007: 150;913-919).*
English translation to wo 02083099.*
Kim et al. (Drug Delivery 2008;15:303-309.*
Strickley (Pharmaceutical Research 2004;21(2):201-230).*
Sokovic et al. (Molecules 2010;15:7532-7546).*
Piao et al. (International Journal of Pharmaceutics 2006;313:159-162.*
PCT ISR and Written Opinion, Jun. 2013.
Chang, C. -M et al, "Effect of dissolution media and additives on the drug release from cubic delivery systems" Journal of Controlled Release, 1997, vol. 46, pp. 215-222.
Hazemoto, N. et al., "pH-sensitive liposome composed of phosphatidylethanolamine and fatty acid," Chem. Pharm, Bull., 1990, vol. 38, No. 3, pp. 748-751.
Phoeung, T. et al., "pH-triggered release from nonphospholipid LUVs modulated by the pKa of the included fatty acid," 2010, vol. 26, No. 15, pp. 12769-12776.
Fernandez, A.G , et al. "Aspirin, Salicylate and Gastrointestinal Injury," Nature Medicine, vol. 1, No. 7, Jul. 1995. pp. 602-603.
Huang et al., "Short- and medium-chain fatty acids exhibit antimicrobial activity for oral microorganisms," *Archives of Oral Biology*, vol. 56, pp. 650-654 (2011).
Office Action cited in related U.S. Appl. No. 13/791,189, dated Nov. 6, 2013.
Stomach Acid Medline Plus [online] retrieved on Feb. 18, 2014 from http://www.nlm.nih.gov/medlineplus/ency/article/003883.htm; 2 pages.
Shiratori et al., Intestinal Fat Digestion Plays a Significant Role in Fat-Induced Suppression of Gastric Acid Secretion and Gastrin Release in the Rat, *Digestive Diseases and Sciences*, vol. 38, No, 12, pp. 2267-2272 (1993).
Russell, "Protection from NSAID-Induced Gastrointestinal Damage," *Inflammopharmacology*, vol. 3, pp. 327-333 (1995).
Wiseman, "Non-Steroidal Anti-Inflammatory Drugs: Facts and Fallacies," *CME*, vol. 21, No. 2, pp. 80-84 (2003).
Final Office Action cited in related U.S. Appl. No. 13/791,189, dated Feb. 20, 2014.
Office Action issued in related U.S. Appl. No. 13/631,963, dated Sep. 2, 2014.
Anderson, et al., (Abstract of Euro. J. Clin. Pharmacol. 1998: 54(5) pp. 399-404).

(56) References Cited

OTHER PUBLICATIONS

Helmenstine (Stomach pH [online] retrieved on Aug. 27, 2014 from http://chemistry.about.com/b/2013/07/08/what-is-the-ph-of-the-stomach.htm 1 page).

Takamura et al., "Determination of Higher Fatty Acids in Fats and Oils by High-Performance Liquid Chromatography with Electrochemical Detection," *The Electrochemical Society*, pp. 568, 571, 575, 576 in part (1997).

Yen, "Influence of Seed Roasting Process on the Changes in Composition and Quality of Sesame (*Sesame indicum*) Oil," *J. Sci. Food Agric.*, vol. 50, pp. 563-570 (1990).

Carvalho et al., "Extraction, Fatty Acid Profile and Antioxidant Activity of Sesame Extract," *Brazilian Journ. of Chem. Eng.*, vol. 29, No. 2, pp. 409-420 (2012).

Nzikou et al., "Chemical Composition on the Seeds and Oil of Sesame (*Sesamum indicum* L. ) Grown in Congo-Brazzaville," *Advance Journ. of Food Science and Technology*, vol. 1, No. 1, pp. 6-11 (2009).

Lecithin (Medical Dictionary [online] retrieved on Sep. 2, 2014 from: http://medical-dictionary.thefreedictionary.com/lecithin.

Sesame Seed Oil [online] retrieved Sep. 2, 2014 from http://www.oilsandplants.com/sesameseed.htm; 2 pages.

Chakrabarty et al., "The Fatty Acids and Glycerides of an Indian sesame Oil," *J. Sci. Food Agric.*, vol. 2, pp. 255-259 (1951).

Matthaus et al., "Comparison of Different Methods for the Determination of the Oil Content in Oilseeds," *JAOCS*, vol. 748, pp. 95-201 (2001).

Office Action issued in related U.S. Appl. No. 13/791,189, dated Sep. 4, 2014.

Office Action issued in related U.S. Appl. No. 13/631,963, dated Jun. 23, 2014.

Smith et al., Introduction to the Principles of Drug Design and Action, Fourth Edition, CRC Press, 2005, pp. 40-41).

Office Action issued in related U.S. Appl. No. 13/631,963, dated Jan. 26, 2015.

Office Action issued in related U.S. Appl. No. 13/791,189, dated Jan. 26, 2015.

Advisory Action and references issued in related U.S. Appl. No. 13/791,189, dated Jun. 9, 2015.

European Extended Search Report issued in related European Patent Application No. EP 12 83 7423, dated Jun. 3, 2015.

Notice of Allowance issued in related U.S. Appl. No. 13/791,189, dated Jul. 13, 2015.

U.S. Office Action issued in related U.S. Appl. No. 13/631,963, dated Aug. 7, 2015.

\* cited by examiner

PH DEPENDENT CARRIERS FOR TARGETED RELEASE OF PHARMACEUTICALS ALONG THE GASTROINTESTINAL TRACT, COMPOSITIONS THEREFROM, AND MAKING AND USING SAME

RELATED APPLICATIONS

The present application claims the benefit of and priority to U.S. patent application Ser. No. 13/631,963 filed 29 Sep. 2012 (Sep. 29, 2012)(29 Sep. 2012), which claims the benefit of and priority to U.S. Provisional Patent Application Ser. No. 61/540,699 filed 29 Sep. 2011 (Sep. 29, 2011)(29 Sep. 2011).

BACKGROUND OF THE INVENTION

1. Field of the Invention

Embodiments of the present invention relate to targeted release carriers and/or pH dependent release carriers and compositions including a targeted release and/or pH dependent release carrier of this invention and at least one biologically active agent and to methods for making and using same.

More particularly, embodiments of the present invention relate to targeted release carriers and/or pH dependent release carriers and compositions including a targeted release and/or pH dependent release carrier of this invention and an effective amount of at least one active agent (one active agent or a plurality of active agents), where the targeted release and/or pH dependent release carriers include at least one biocompatible agents (one active agent or a plurality of biocompatible agents), and where the active agents include nutraceutical agents and/or pharmaceutical agents and where the targeted release and/or pH dependent release carriers include at least one targeted release and/or pH dependent release agent for the active agents so that the biologically active agents may be released into the tracts of an animal, mammal, or human in a targeted manner. Embodiments of the invention also relate to methods for making and using the carriers and/or compositions.

2. Description of the Related Art

U.S. Pat. No. 4,666,701 disclosed gamma-linolenic acid or dihomo-gamma-linolenic acid for use in the reduction or prevention of gastrointestinal bleeding and other side effects of non-steroidal, anti-inflammatory drugs (NSAIDs), when administered on a continuing basis, including use in allowing said administration to be replaced by administration of said acid alone in arthritis and other conditions without exacerbation of symptoms. This patent also included no teaching on targeted release of biologically active agents mediated by free fatty acids.

However, free fatty acids are known to be injurious to the upper GI tract. See, e.g., Velasquez et al. "Oleic acid-induced mucosal injury in developing piglets intestine," *Am. J. Physiol* 64, g576-81, 1993; Velasquez et al. "Fatty acid-induced injury in developing piglet intestine: effect of degree of saturation and carbon chain length," *Pediatr. Res.* 33, 543-7, 1993; and such membrane injuries action has been therapeutically exploited (See Croffie et al. "Sclerosing agents for use in GI endoscopy," *Gastrointestinal Endoscopy* 66, 1-6, 2007 (ethanolamine oleate, a drug used to induce endothelial membrane damage for the treatment of esophageal varices). Thus, the formulations of this invention include large quantities of two components known to be injurious to the upper GI tract, an NSAID and free fatty acids (Davenport, "Gastric mucosal injury by fatty and acetylsalicylic acids", Gastroenterology, 46, 245-253, 1964, yet the formulations of this invention show comparable if not superior protection against NSAID GI toxicity.

U.S. patent application Ser. No. 10/433,454 filed 6 Nov. 2003 disclosed a composition including a biocompatible oil carrier having a relatively high phospholipid content for non-steroidal anti-inflammatory drugs (NSAIDs) showing reduced gastrointestinal (GI) NSAID toxicity. The preferred neutral lipids in these carriers were uncharged lipids: triglycerides, which remain uncharged at all relevant pHs pH between 1 and 9.

In U.S. Pat. Nos. 4,950,656, 5,043,329, 5,763,422, and 5,955,451, saturated zwitterionic phospholipids in combination with saturated triglycerides were used to reduce GI toxicity, to increase the cyclohexane solubility of the NSAIDs, and to improve NSAID efficacy. U.S. Pat. Nos. 5,763,422, and 5,955,451 specifically demonstrated that aspirin (ASA): dipalmitoyl phosphatidylcholine (DPPC) solubility in cyclohexane was enhanced by the addition of a triglyceride, tripalmtin. It was believed that the enhanced cyclohexane solubility was linked to the improved NSAID efficacy and/or reduced ASA GI toxicity.

In publications and patents by Lichtenberger and coworkers, compositions including a phospholipid and an NSAID were formed either by initially dissolving the components in an organic solvent, such as methanol, ethanol or chloroform, and removing the solvent by distillation or evaporation; or the NSAID was dissolved in an aqueous solution at or above the pKa of the NSAID and to a phospholipid film, followed by lyophilization if a solid product was required. These processes allow the two components to chemically interact to form associated complexes. These processes most often used a phosphatidylcholine (PC) as the phospholipid either synthetically prepared such as dipalmitoylphosphatidylcholine (DPPC) or as a purified or semipurified PC compound.

More recently, in U.S. Pat. No. 6,451,339, Patel et al. disclosed compositions and for improved delivery of hydrophobic agents, where the compositions are substantially triglyceride-free and include a combination of a hydrophilic surfactant and a hydrophobic surfactant.

While these patents and applications disclose compositions and methods for preparing the compositions, where the compositions are effective in reducing the GI toxicity of NSAIDs, the patents and applications fail to disclose any information for the preparation of carrier that possess the ability to target the release of NSAIDs into different parts of the GI tract. Targeted release of biologically active agents exploiting the differential pH profile of the GI tract has been disclosed using various pH sensitive polymers as coatings for acid labile drugs and drugs having upper gastrointestinal toxicity. However, this approach has been limited by stochastic pharmacokinetics and marked food effects (Leonards, J. R. and G. Levy, *JAMA* 193: 99-104, 1965, Bogentoft, C., I. Carlsson, et al., *European Journal of Clinical Pharmacology*, 14(5), 351-355, 1978.

Thus, there is a need in the art for new and novel carriers and compositions including the carriers that are capable of targeted release of active agents into different areas of the GI tract and other tracts such as the urinary or reproductive tracts. There is also a need in the art for carriers and compositions including the carriers that are capable of a targeted release and/or pH dependent release of an active ingredient, where the targeted and/or pH dependence conforms to a targeting profile and/or pH profile of the tract in the body of an animal, mammal or human so that biologically active agents such as NSAIDs are released selectively in the tract such as into the duodenum or the small intestine and not the stomach of the GI tract, i.e., the carriers release the biologically active agents slowly and inefficiently in low pH environments such as gastric fluid, but release the biologically active agents rapidly and efficiently at higher pH environments (e.g., pH values between 4 and 5) such as the upper duodenum, and even higher pH environments (e.g., pH values between 7 and 8) in the presence of bile acids in small intestinal fluid.

SUMMARY OF THE INVENTION

Overview

The carriers of this invention and compositions including the carriers of this invention possess the capability of targeted release of a biologically active agent into a selected region of a targeted tissue, organs, or tracts, such as release into a region of the gastrointestinal (GI) tract, urinary tract, reproductive tract, or other tracts that have mucosal gels. Carrier-mediated targeted release is particularly useful for active ingredients that are: (a) injurious to the upper GI tract (esophagus, stomach, and duodenum), (b) acid labile, (c) impermeable/insoluble compounds GI fluids, (d) susceptible to first pass metabolism, and (e) cause stomach irritation, upset, or dyspepsia. In certain embodiments, the targeted release is a pH dependent release so that the biologically active agent(s) is(are) released minimally at low pH of the stomach (e.g., a pH less about 3-<pH 3) and are efficiently released at higher pH of the upper duodenum (e.g., at pH greater than to or equal to 4-≥pH 4). In certain embodiments, the targeted release is a pH dependent release so that the active agent(s) is (are) released minimally at low pH of the stomach (e.g., a pH less about 3-<pH 3) and upper duodenum (e.g., at pH greater than to or equal to 4 to 5), and are efficiently released at the higher pH of the small intestine in presence of high concentration of bile. In certain embodiments, the pH dependent release of the active agent(s) is due to the inclusion in the carrier of pH dependent release agents such as at least one oil soluble or miscible compound including at least one ionizable group such as a carboxylic acid group, hydroxy group, amino group, amide groups, or other similarly ionizable groups. In other embodiments, the at least one ionizable group includes at least one carboxylic acid group or at least one oil soluble or miscible compound including at least one carboxylic acid group. In other embodiments, the compounds including at least one carboxylic acid group are fatty acids sometimes referred to herein as free fatty acids to fully distinguished these acids from the ester group of mono-, di, and tri-glycerides. Fatty acids are particularly useful for tailored release of biologically active agents along the GI tract and other tracts having a pH profile, because most fatty acid are nonionized or neutral at low pH (e.g., gastric fluid pH), but become ionized at higher pH (e.g., intestinal fluid pH), which enables them to selectively deliver a biologically active agent payload. We present herein partitioning data, dissolution data, Fourrier Transform Infra Red (FTIR) spectrometry data, and animal data that demonstrate the targeted release of NSAIDS, the pH dependent release of NSAIDs, and the efficacy of these targeted NSAID release, and/or pH dependent release carriers in mammals. These data clearly demonstrated that the carriers of the invention are ideally suited for the targeted release of NSAIDs into different regions of the GI tract. The partitioning data and the animal toxicity data demonstrated that these carriers are effective at targeting the release of aspirin in a pH dependent manner and that the targeted release selectively to the small intestine is efficient in reducing aspirin gastric toxicity. The data also showed that the targeted and/or pH dependent release agents are operable even in the presence of other components at relatively low and relatively high levels such as phospholipids, triglycerides, etc. The data also showed that the targeted and/or pH dependent release characteristics of the carriers of this invention are effective for different NSAIDs and NSAID classes. As these NSAIDs are all weak acids, the efficacy of these compositions to demonstrate targeted and/or pH dependent release of different NSAIDs, strongly supports the capability for the carriers of this invention to also be useful for the targeted and/or pH dependent release of other pharmaceuticals and/or nutraceuticals. The data also showed that the release characteristics of the carriers may be designed such that the biologically active agent(s) is(are) released at low pH instead of higher pH so that the active agent may be targeted to tissue in contact with low pH environments such as the stomach. Thus, the carriers of the present invention produce new, novel and readily tailored active agent compositions having unique active agent release characteristics, unique active agent efficacies, and/or unique active agent GI bioavailability and/or toxicity. As this targeted release of the active agents from the lipid matrix appears to be due to ionization state of the targeted release agents in the carrier relative to pH and other physiological milieu of in selected regions of the tracts such as the GI tract, targeted release of any biologically active agent may be possible.

Carriers

Embodiments of the present invention provide carriers that possess the capability for targeted active agent release and/or pH dependent active agent release. The carriers generally include at least one targeting release agent, where the agent is capable of releasing an active agent or plurality of active agents in a targeted manner. In certain embodiments, the targeting release agents are pH dependent release agents that release the active agents in a pH dependent manner. The carriers may also include other biocompatible agents to modulate the desired release and/or dissolution characteristics or to modify and/or alter other properties of the carrier and/or biologically active agents. Besides targeting the release for example in a pH dependent manner, the carriers and/or components thereof may also modify and/or alter the chemical properties, physical properties, and/or behavior of the active agents in tissues and/or organs, when administered to an animal, mammal, or human.

Embodiments of the present invention provide carriers capable of pH dependent release of an active agent or plurality of active agents, where the carriers include at least one pH dependent release agent such as at least one oil soluble or miscible compound including at least one ionizable group such as a carboxylic acid group, hydroxy group, amino group, amide groups, or other similarly ionizable groups. In other embodiments, the carriers include at least one carboxylic acid group or at least one oil soluble compound including at least one carboxylic acid group are free fatty acids.

Compositions

Embodiments of the present invention provide compositions including a carrier of this invention and an effective amount of at least one biologically active agent, where the carrier is designed to effect a targeted release of the active agents and/or to modify and/or alter the chemical properties, physical properties, and/or behavior of the active agents in tissues and/or organs, when administered to an animal, mammal, or human.

Embodiments of the present invention provide compositions including a carrier of this invention and an effective amount of at least one pharmaceutical agent and/or nutraceutical agent, where the carrier is designed to effect a targeted release of the pharmaceutical agents and/or nutraceutical agents and/or to modify and/or alter the chemical properties, physical properties, and/or behavior of the agents in tissues and/or organs, when administered to an animal, mammal, or human.

The above compositions may be in the form of a solution of the active agents in the carrier, a suspension of the active agents in the carrier, where some of the active agents may be dissolved in the carrier, a suspension of the active agents in the carrier, where no active agent is dissolved in the carrier, a paste of the active agents in the carrier, or any other mixture or combination of the active agents in the carrier or surrounded by the carrier. The active agents may be present in the carrier in an amount sufficient to produce a paste like suspension, a coated solid material such as coated crystals or coated micro or nano particles, where the coating may be from a monolayer to millimeters in thickness, a matrix of coated solid material, or any other form including a carrier of this invention and one or more active agents.

Methods for Making

Embodiments of the present invention provide methods for making the carriers of this invention by mixing desired components together under conditions of temperature, pressure, and time sufficient in the presence or absence of a solvent system to form a carrier having tailored active agent release properties and/or tailored active agent interaction properties. If a solvent system is used, the solvent is removed by distillation and/or evaporation.

Embodiments of the present invention provide methods for making the compositions of this invention by contacting a carrier of this invention and an effective amount of at least one active agent under conditions of temperature, pressure, and time sufficient in the present or absence of a solvent system to form a composition having tailored active agent release properties and/or tailored active agent interaction properties. If a solvent system is used, the solvent is removed by distillation and/or evaporation and this method is sometimes referred to as the solvation/evaporation method. In the absence of a solvent system, the active agents are simply admixed with the carrier under conditions of temperature, pressure, and time sufficient to form the designed composition and this method is sometimes referred to as the admix method. In certain embodiments, the active agents comprise at least one pharmaceutical agent and/or at least one nutraceutical agent. It should be recognized by an ordinary artisan that the admix method reduces step and eliminates any concern for trace solvent and could include advantages such as lowered manufacturing cost, environmental manufacturing concerns, etc. Alternatively, certain formulations may benefit from solvation of the ingredients.

Methods for Using

Embodiments of the present invention provide methods for administering compositions of this invention, where the method comprises administering a composition of this invention including a carrier and an effective amount of at least one active agent to a human, mammal, or animal, where the effective amount is sufficient to illicit a desired response. The mode of administration may be oral administration, sublingual or rectal administration, or esophageal, gastric, intestinal instillation via endoscopy. In certain embodiments, the administration may be topical such as administration into ophthalmic, urinary, the reproductive, or other tract, tissue, or organ for which topical administration represents an effective treatment methodology.

Methods for Screening

Embodiments of the present invention also provide methods for screening active agents such as pharmaceutical agents and/or nutraceutical agents, where the method comprises forming a composition including a test active agent in a carrier of this invention. Once the composition is formed, the composition is placed in a differential solubility system. Once added to the differential solubility system, the method includes determining the partitioning coefficient of the active agent between the two immiscible solutions or solvents. To determine the relative release, solubility, and partitioning across the relatively pure hydrophobic mucosa or epithelial membranes of the stomach or duodenum, a two phase system comprised of cyclohexane and simulated gastric fluid (e.g., 0.1 HCl) or cyclohexane and upper duodenal fluid (e.g., pH 4.5 buffer) may be used. To determine the partitioning across epithelial, cellular, or intracellular membranes of mixed polarity of the stomach or duodenum, a two phase system comprised of octanol and simulated gastric fluid (e.g., 0.1 HCl) or octanol and upper duodenal fluid (e.g., pH 4.5 buffer) may be used. To determine the relative release, solubility, and partitioning across the relatively more hydrophilic mucosal surface than the stomach, a two phase system comprised of octanol and simulated intestinal fluids containing digestive enzyme and lipid emulsifying agents (e.g., pH 7.2 buffer with 1% Pancreatin and 20 mM cholic acid) may be used. Embodiments of the screening method may also include varying the pH of the aqueous media and determining the partitioning coefficient at different pH values to test the pH dependent partitioning characteristics of the active agent in the carrier. We believe that the differential partitioning coefficients are an indirect measure of the ability to target the delivery of the active agent from a given carrier so that carrier properties may be tailored for a given active agent delivery profile such as a targeted delivery of an active agent in the GI tract.

Methods of Testing pH Dependent Release Capabilities

Embodiments of the present invention also provide methods for testing active agents such as pharmaceutical agents and/or nutraceutical agents for pH dependent release from a carrier of this invention, where the method comprises forming a composition including a test active agent in a carrier of this invention. Once the composition is formed, the composition is filled into hard shell capsules. Once the composition is filled into the capsules, the capsules are placed in a plurality of dissolution buffers having different pH values and/or different digestive enzyme and/or bile acid levels, measuring the rate of dissolution in the different buffers and determining the pH dependent release properties of the test active agent in the carrier. We believe that the dissolution data permits the preparation of compositions designed to release the active agent at a desired location along a tract of an animal, mammal, or human tract such as the GI tract.

BRIEF DESCRIPTION OF THE DRAWINGS

The invention can be better understood with reference to the following detailed description together with the appended illustrative drawings in which like elements are numbered the same.

pH Dependent Release of Biologically Active Agents

Free Fatty Acids in Lecithin Oil Mediate pH Dependent Release of Biologically Active Agents

Targeted Release of Biologically Active Agents Along the GI Tract

Figure 7:
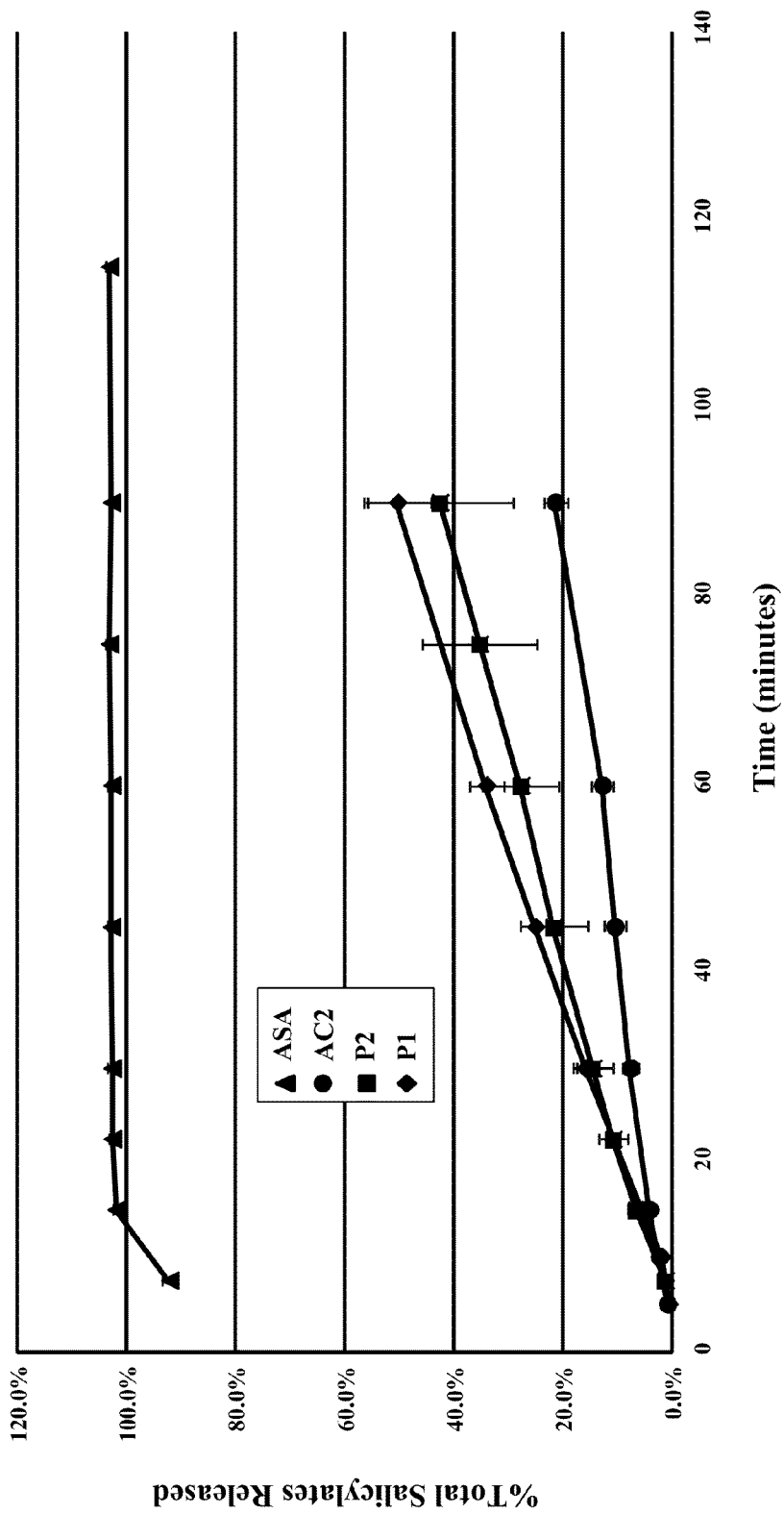

FIG. 7 depicts dissolution profiles in "simulated gastric fluid" (0.1 N HCl) pH 1 at 150 rpm. The data are mean±standard deviation (SD) of replicate determinations.

Figure 8:
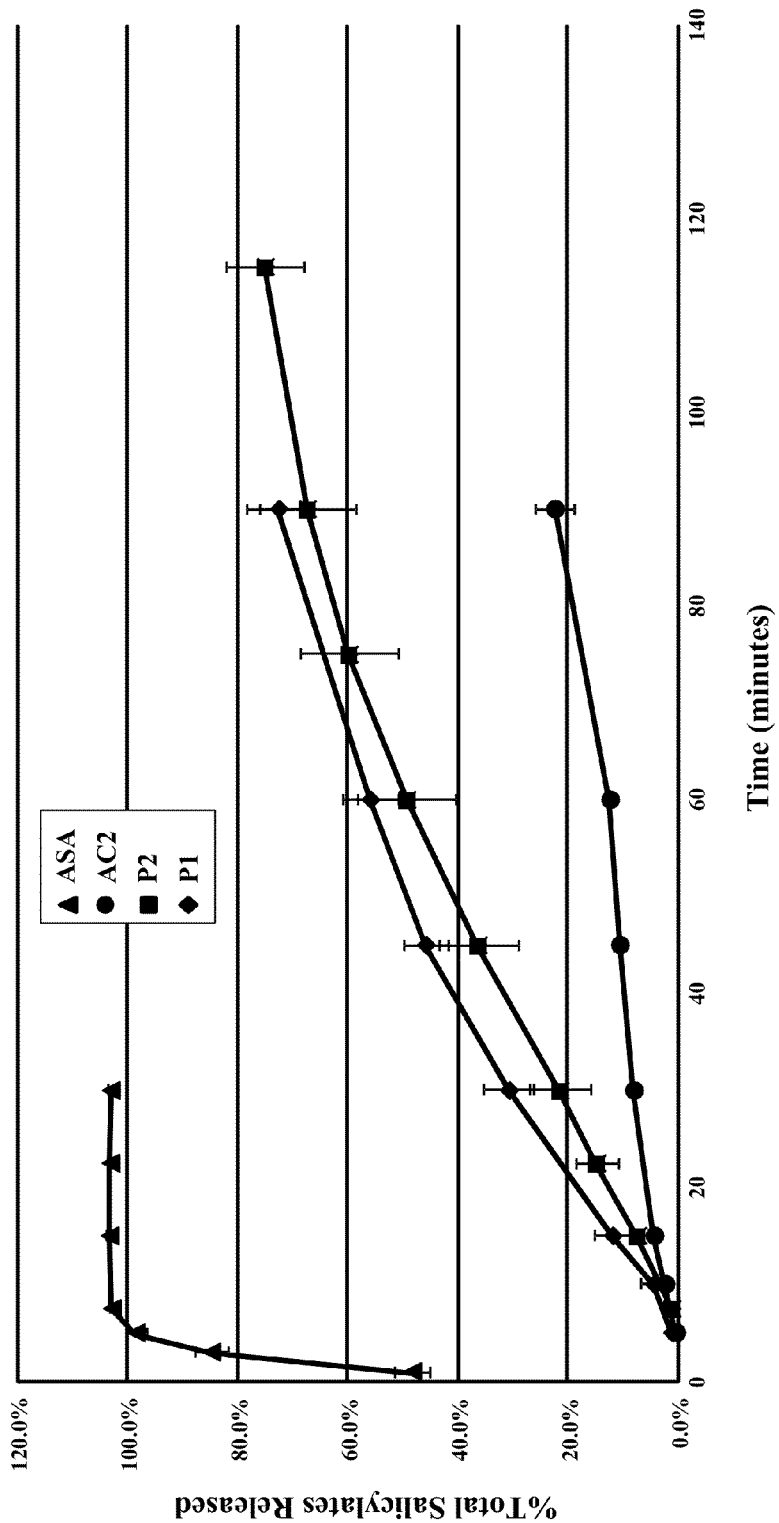

FIG. 8 depicts dissolution profiles in "simulated duodenal fluid" pH 4.5 at 150 rpm. The data are mean±standard deviation (SD) of replicate determinations.

Figure 9:
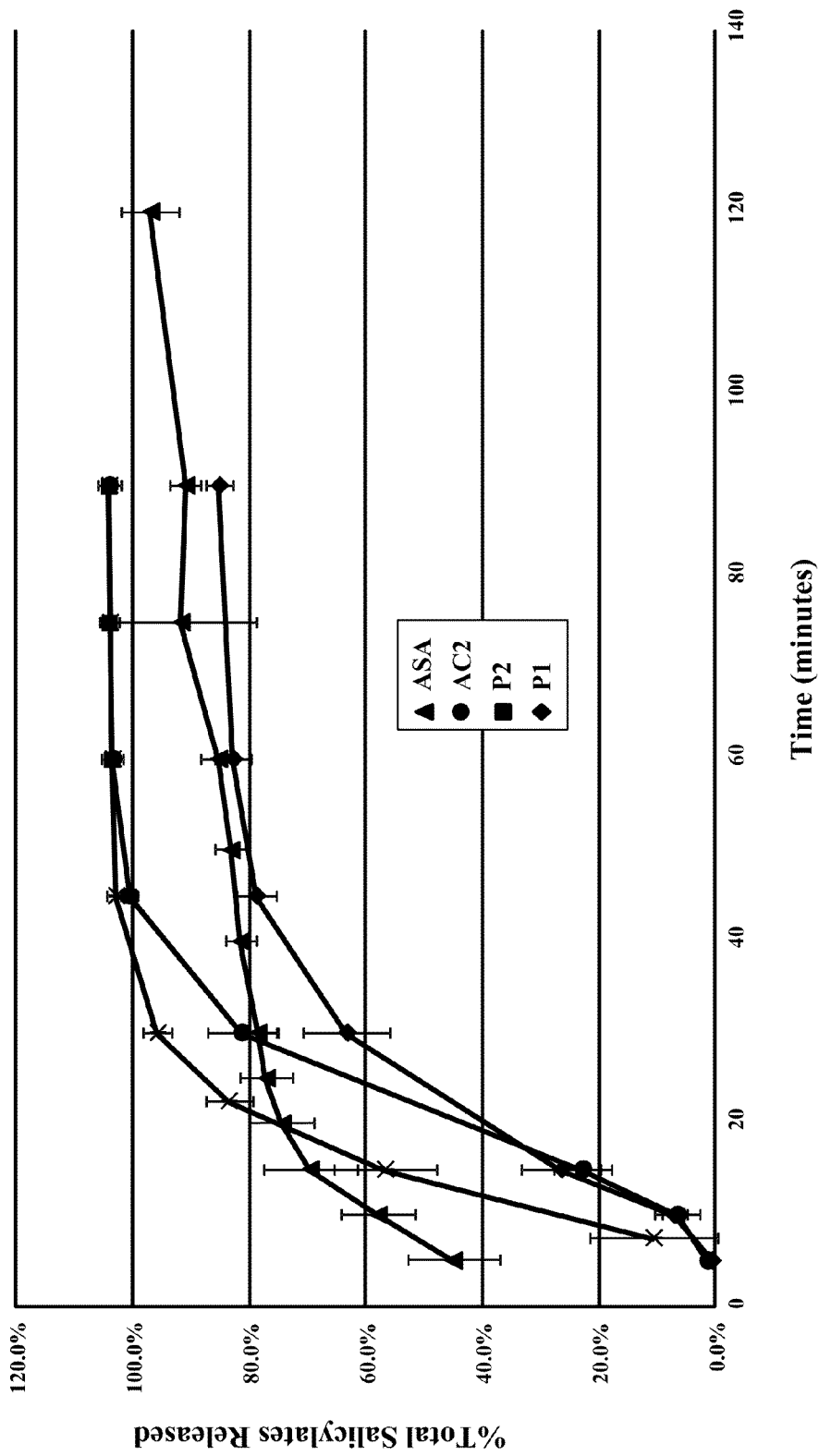

FIG. 9 depicts dissolution profiles in "simulated intestinal fluid" pH 7 at 150 rpm. The intestinal fluid is a phosphate buffer, supplemented with 1% pancreatin, and 20 mM cholic acid, pH 7. The data are mean±standard deviation (SD) of replicate determinations.

Figure 10A:
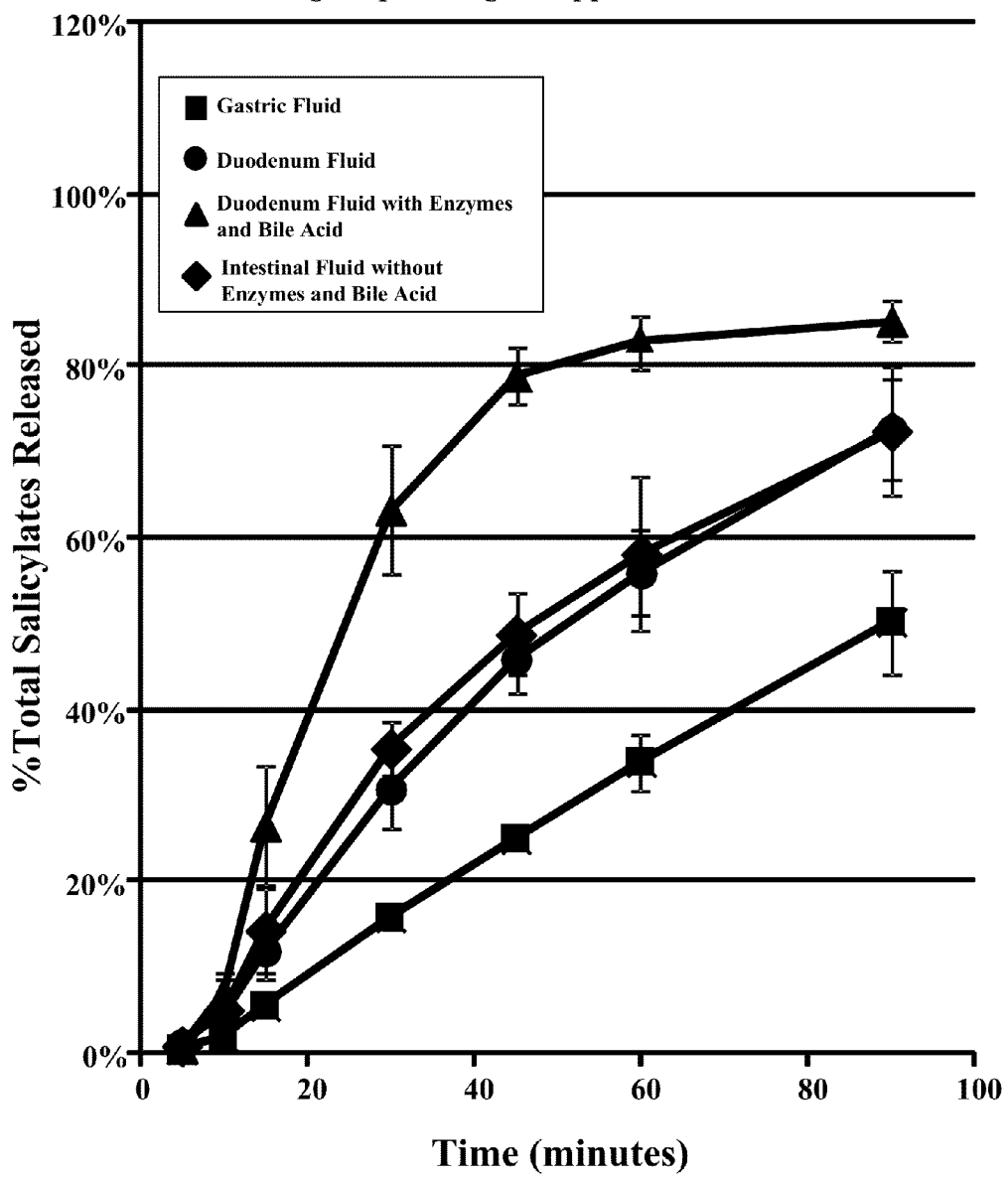
Figure 10B:
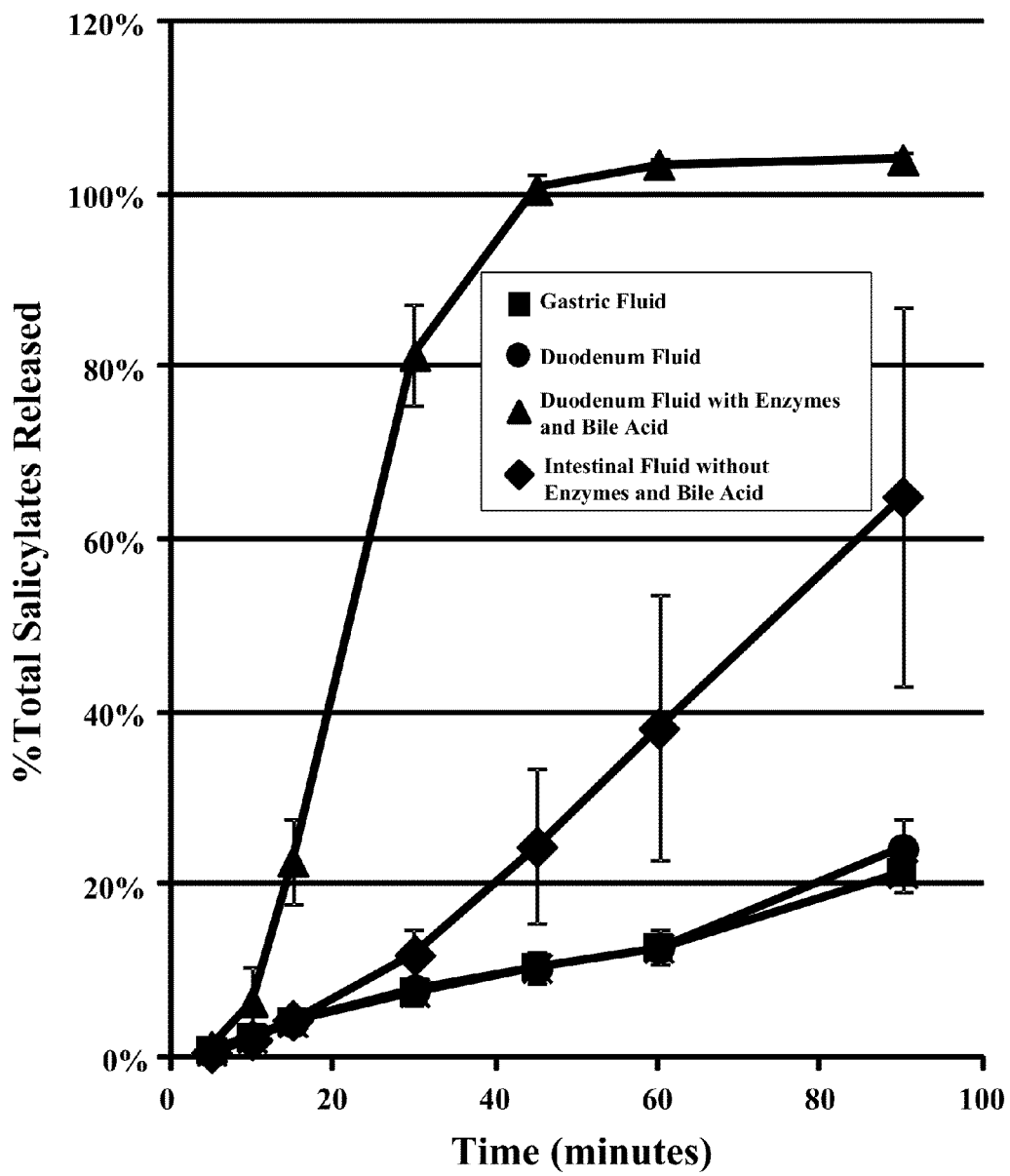

FIGS. 10A&B depict a side by side comparison of average dissolution profiles of 0 wt. % PC and 2.5 wt. % PC formulations in different media: simulated gastric, duodenal and intestinal fluid, and a phosphate buffer, pH 6.8. The data are mean±standard deviation (SD) of replicate determinations.

pH Profile and General Composition of the Luminal Fluid in Upper GI Tract

Figure 11:
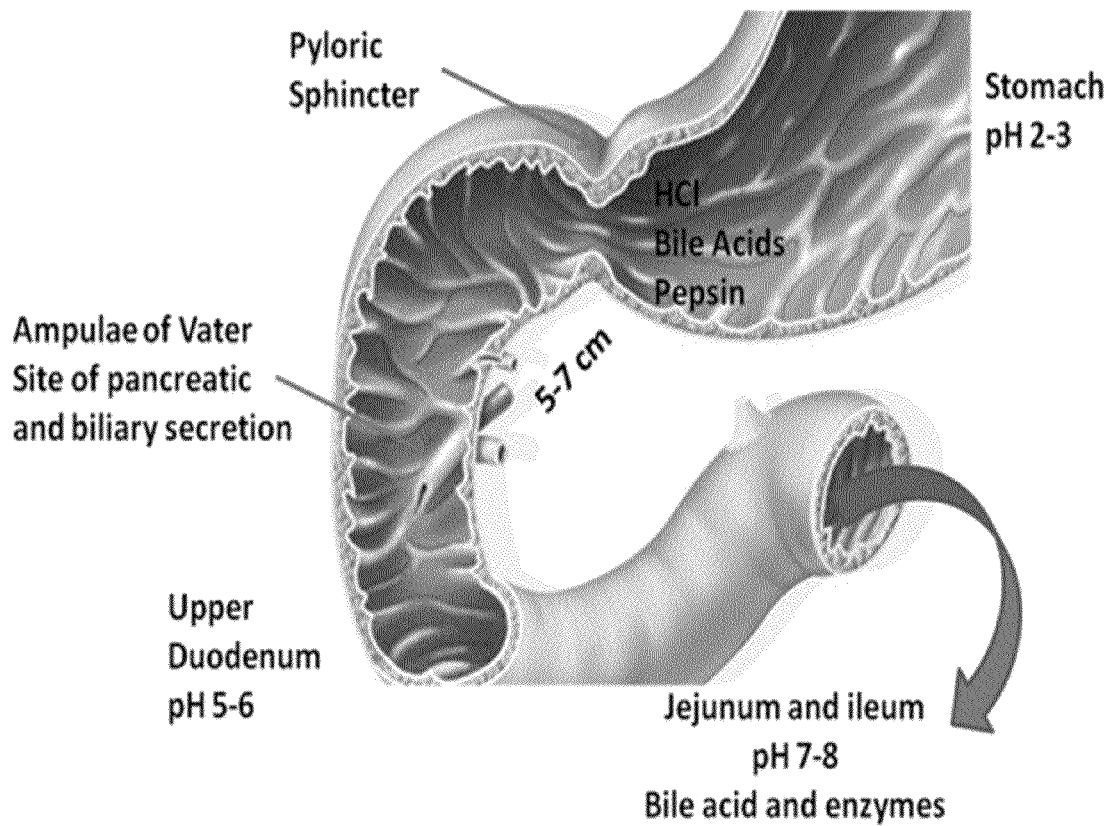

FIG. 11 depicts a drawing of the human upper GI tract including the stomach and small intestine (duodenum, jejunum, and ileum) indicating the pH ranges for the different regions of the upper GI Tract. Generally, gastric pH is acidic. Progressively distal to the stomach, the small intestine become more alkaline largely due to pancreatic secretions. The alkaline pH and high concentration of bile acids, particularly after a meal, in the jejunum and ileum enable emulsification/digestion of lipids.

Figure 12:
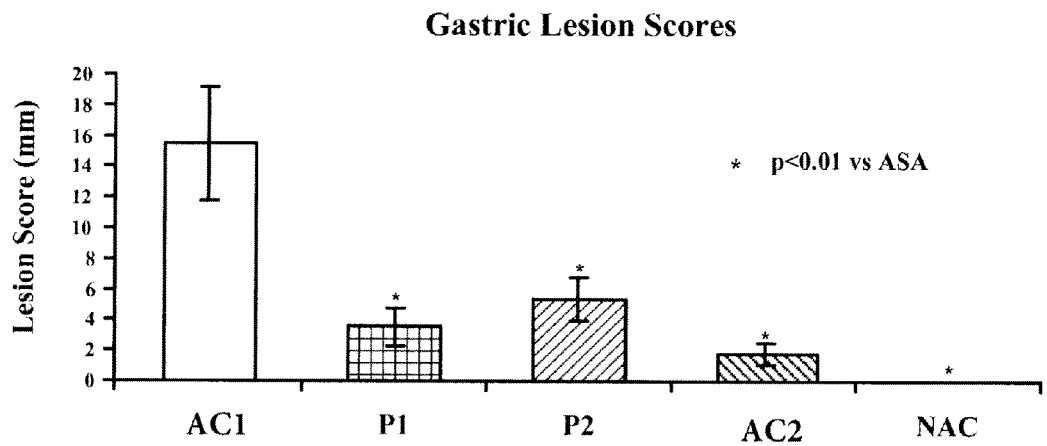

Targeted Release of Biologically Active Agents Along the GI Tract Improving GI Safety FIG. 12 depicts gastric lesions in rats treated with once daily 40 mg/kg of aspirin from the following AC1, P1, P2, and AC2 Formulas or negative control (NAC).

Figure 13:
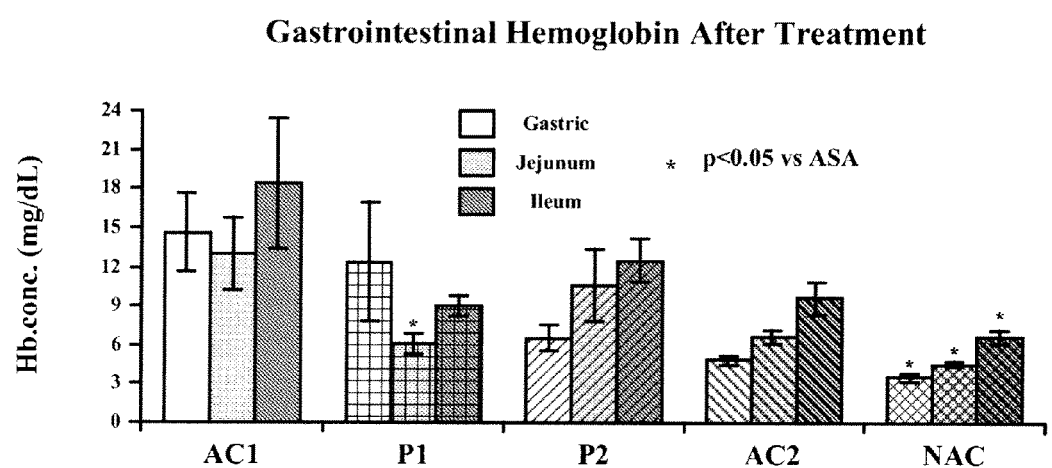

FIG. 13 depicts luminal gastric and intestinal hemoglobin following 3-day treatment with NAC, AC1, P1, P2, and AC2.

Figure 14:
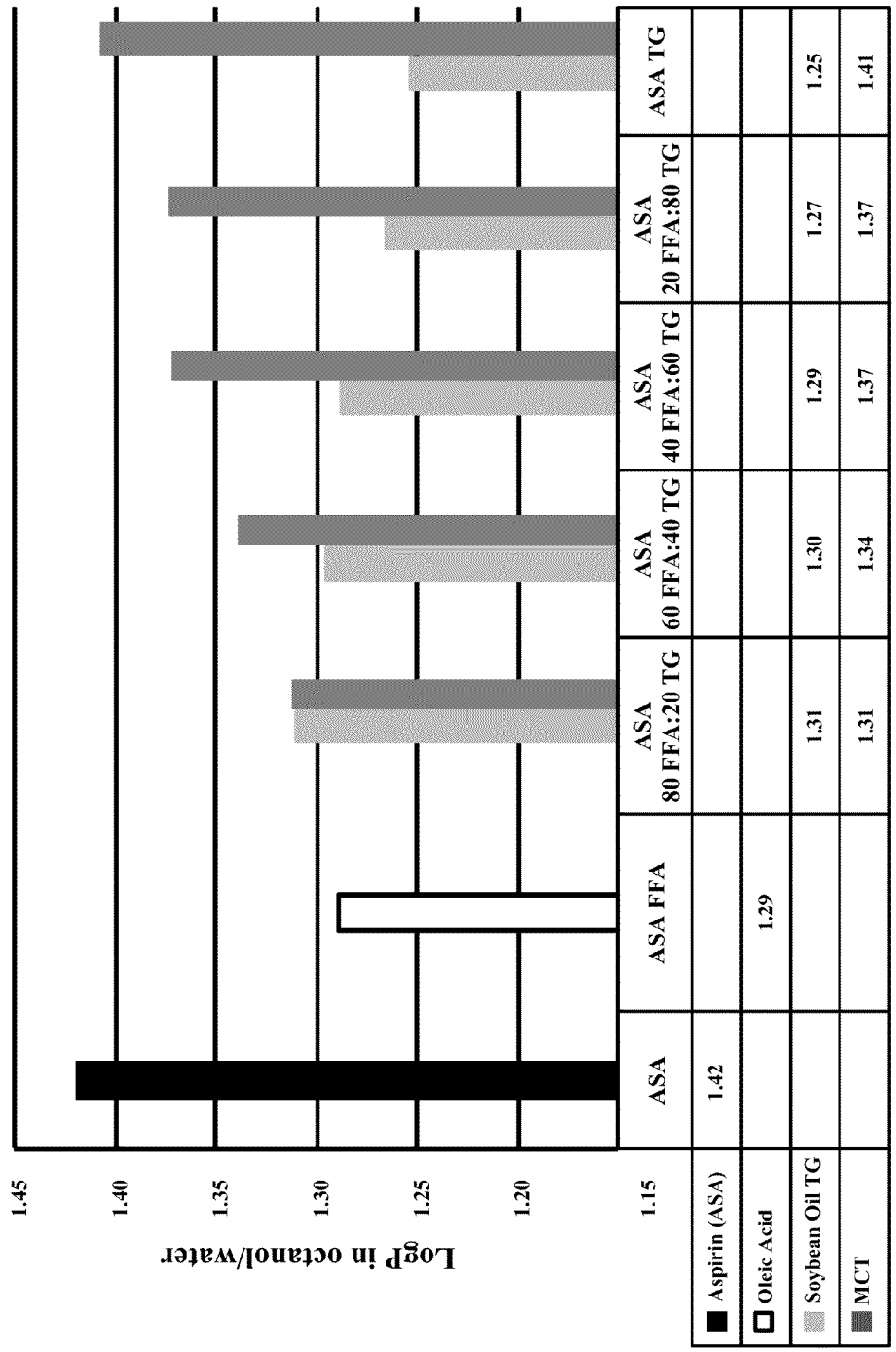

Use of Carriers to Increase Bioavailability of Poorly Permeable Biologically Active Agents FIG. 14 depicts FTIR spectra of aspirin in various carriers.

Figure 15:
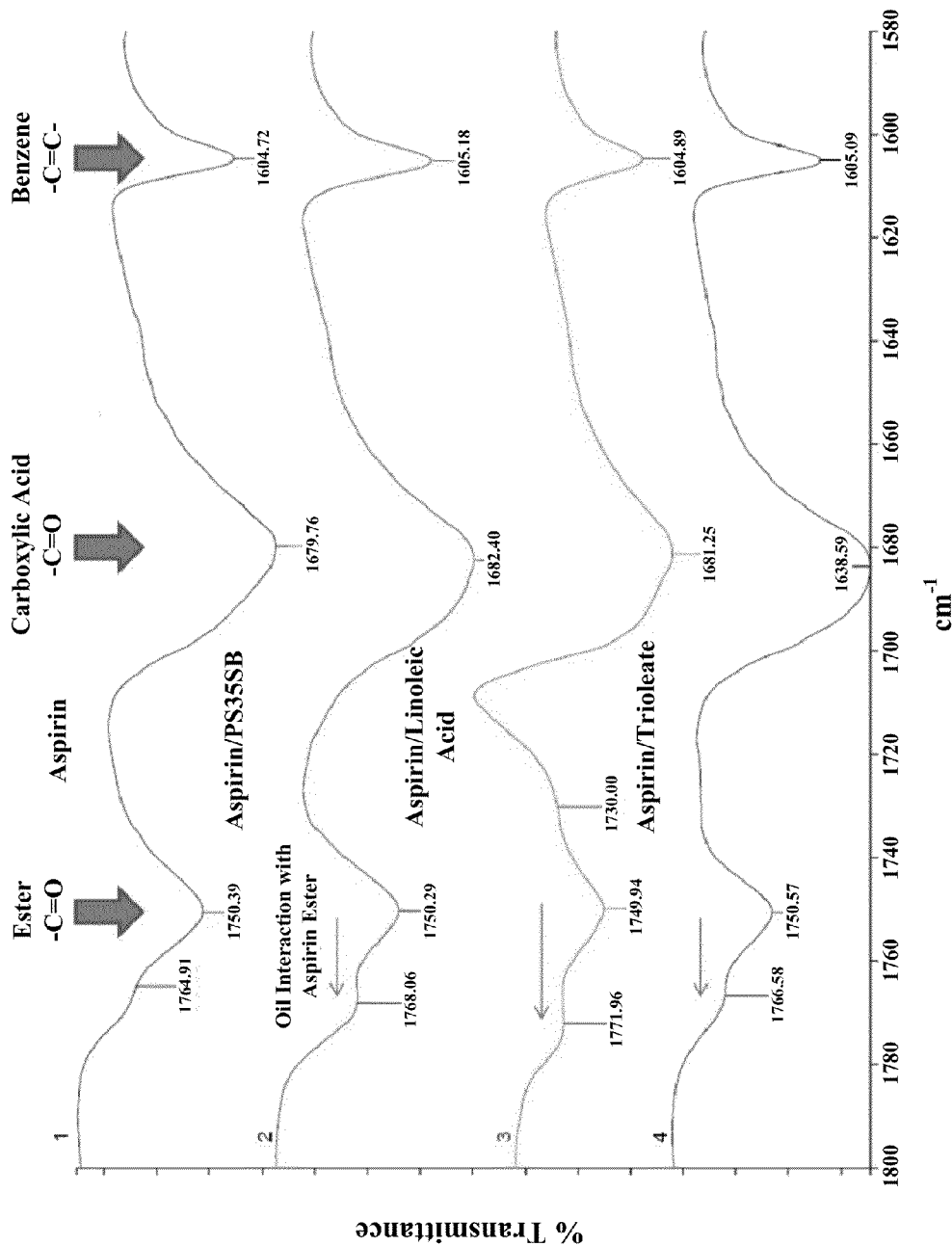

FIG. 15 depicts ASA partitioning in an octanol/0.1 N HCl system using carriers having different FFA:TG ratios ranging from 100:0 to 0:100 in increments of 20.

Generalizability of Carrier-Targeted Release to all Weak Acid Biologically Active Agents Salicylic Acid (SA)

Figure 16:
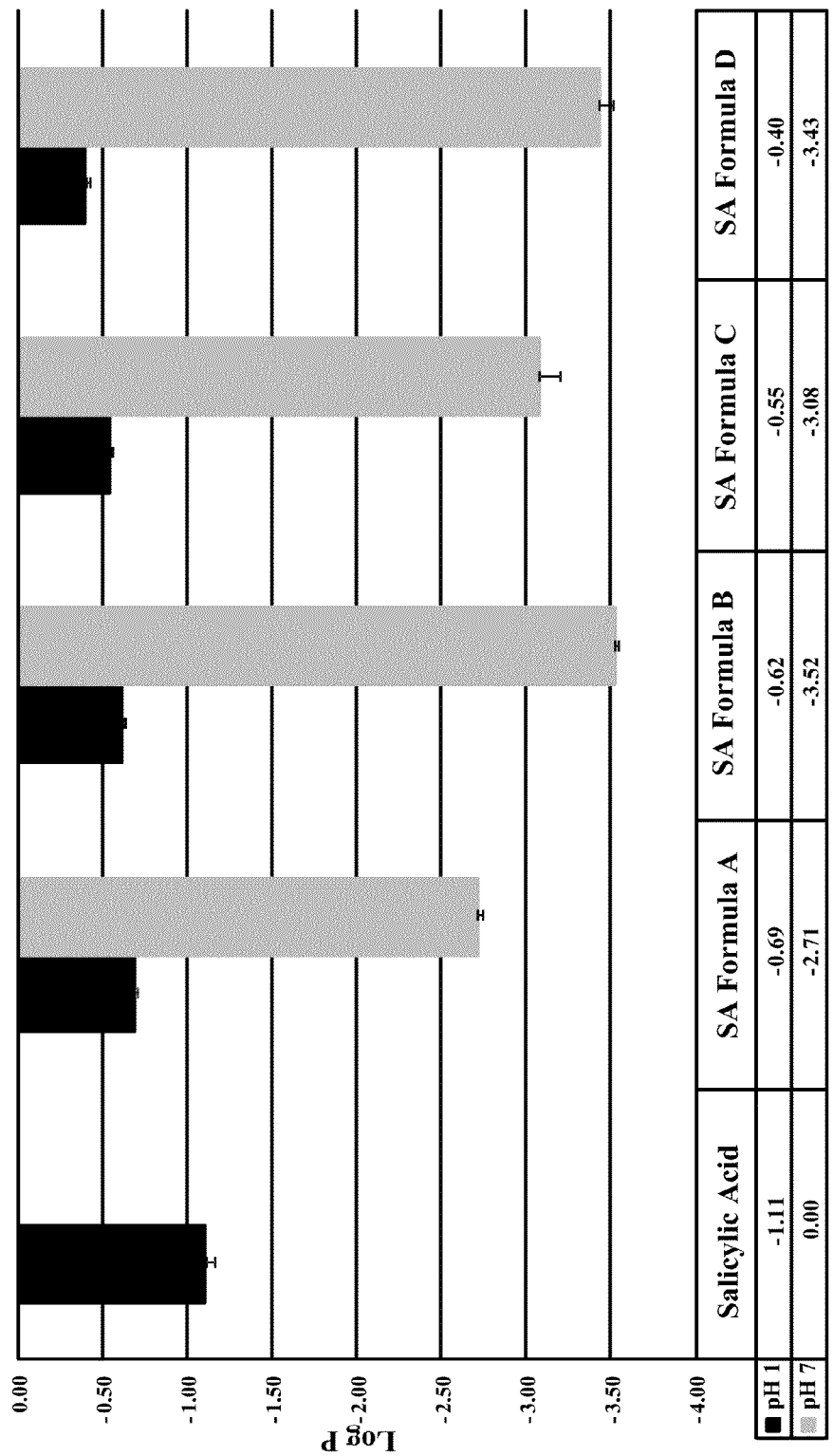

FIG. 16 depicts partitioning at low and at neutral pH for salicylic acid (SA) and SA Formulas A, C, E, and G.

Figure 17:
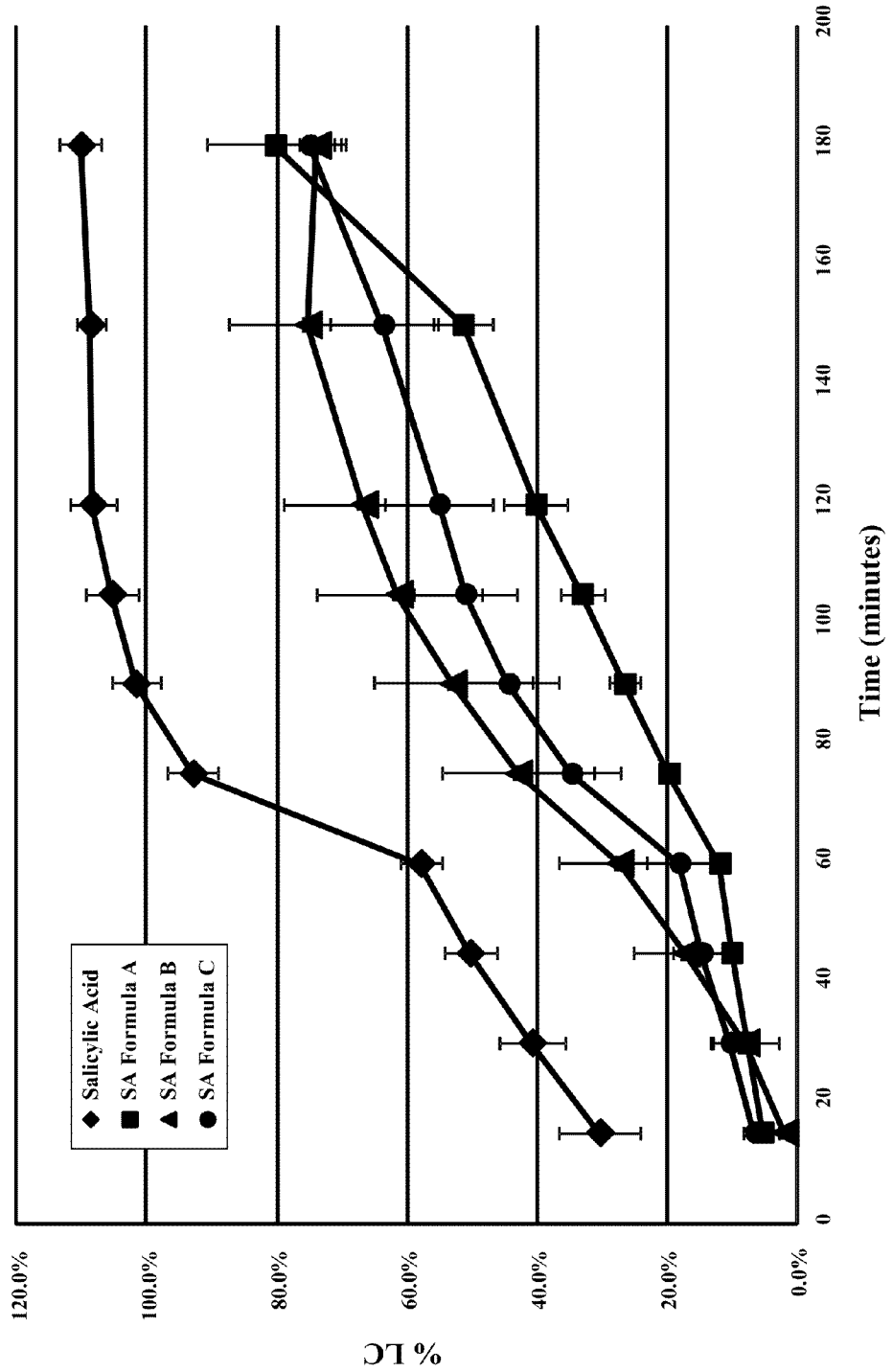

FIG. 17 depicts two stage dissolution profiles in pH 1 "simulated gastric fluid" then in pH 7.2 "simulated intestinal fluid" at 75 RPM for salicylic acid in various carriers.

Naproxen (NAP)

Figure 18:
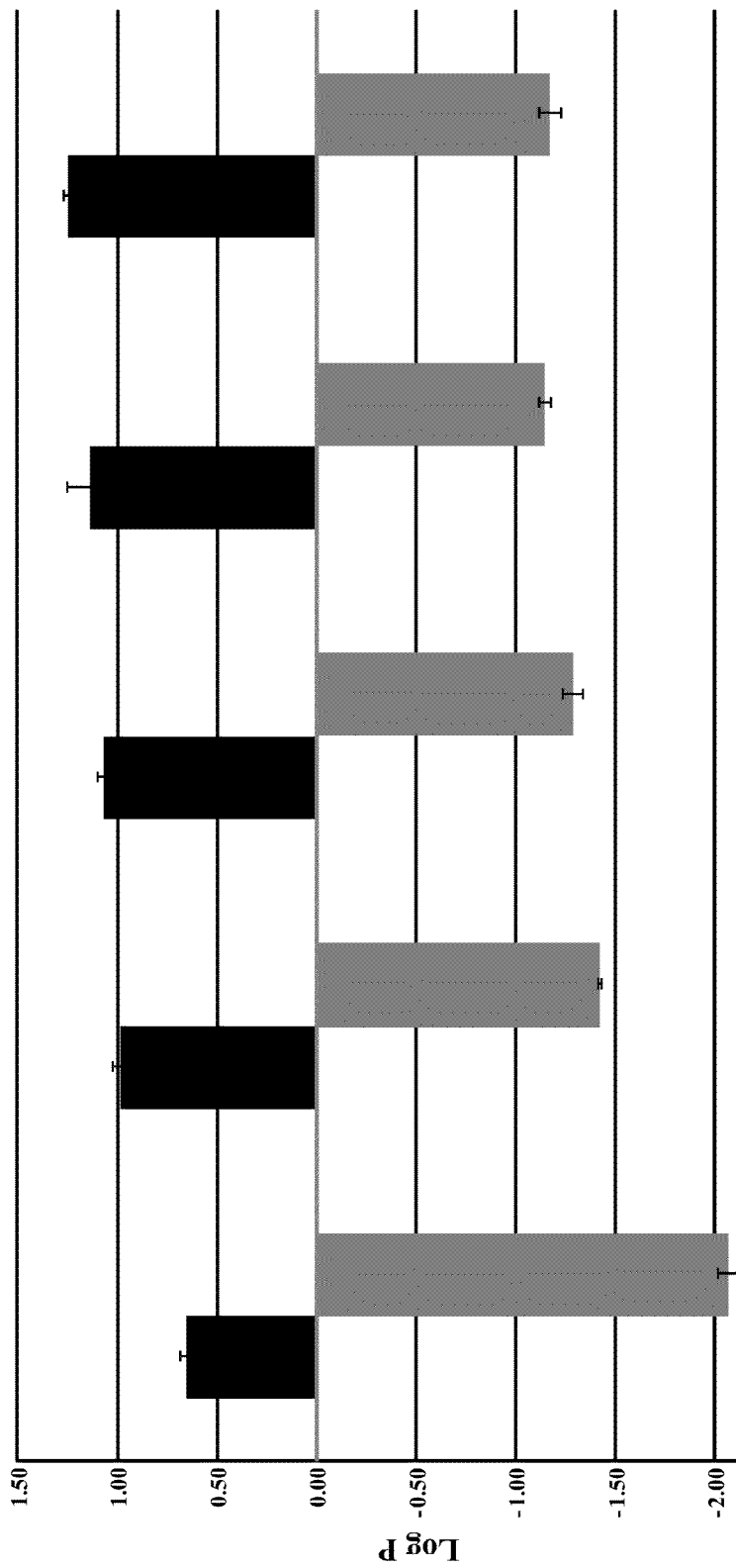

FIG. 18 depicts partitioning at pH 1 and at pH 7 for naproxen acid (NAP) unmodified and in NAP Formulas A, C, E, and G.

Indomethacin (INDO)

Figure 19:
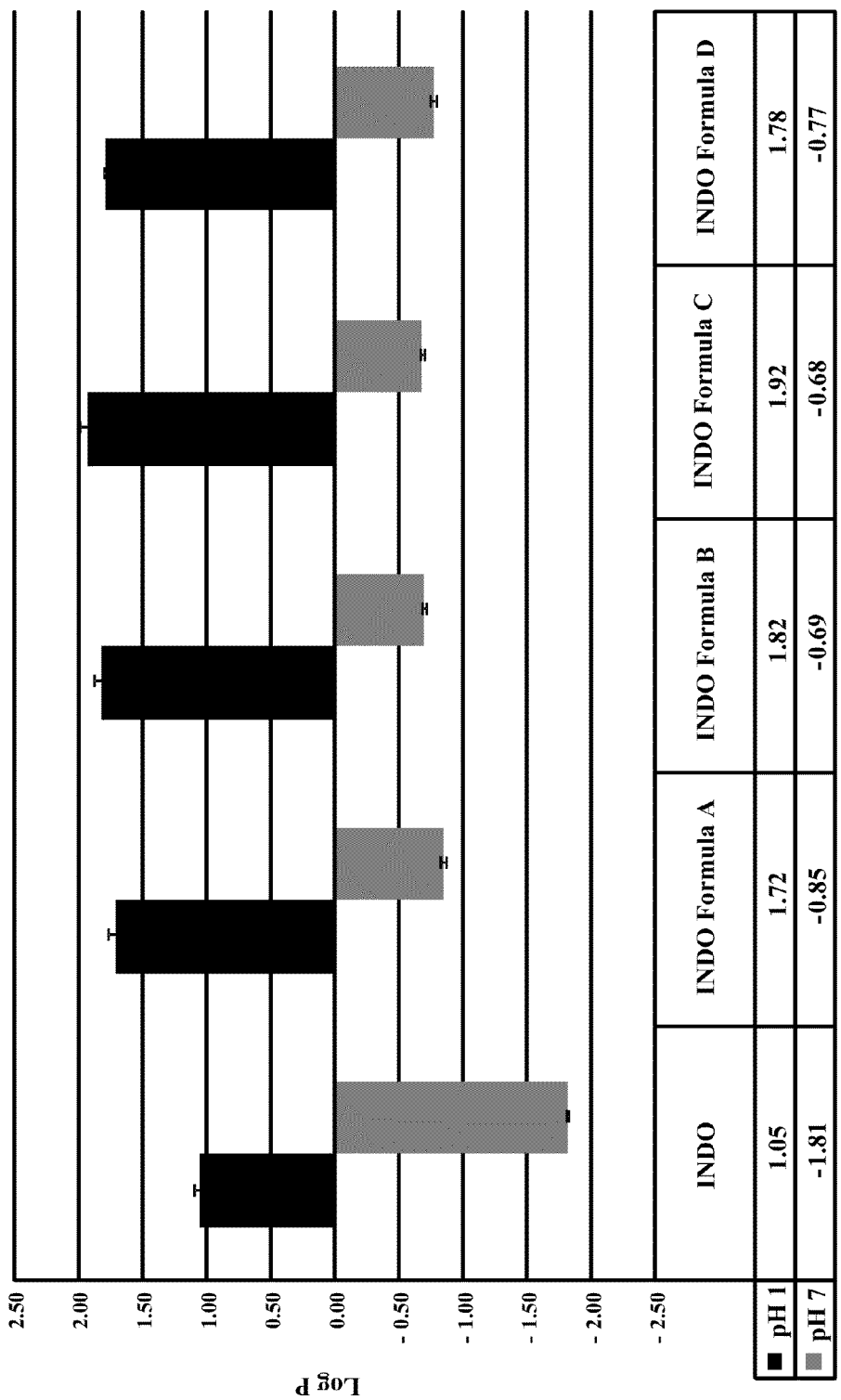

FIG. 19 depicts partitioning at pH 1 and at pH 7 for indomethacin (INDO) unmodified and in INDO Formulas A, C, E, and G.

Mefenamic Acid (MFA)

Figure 20:
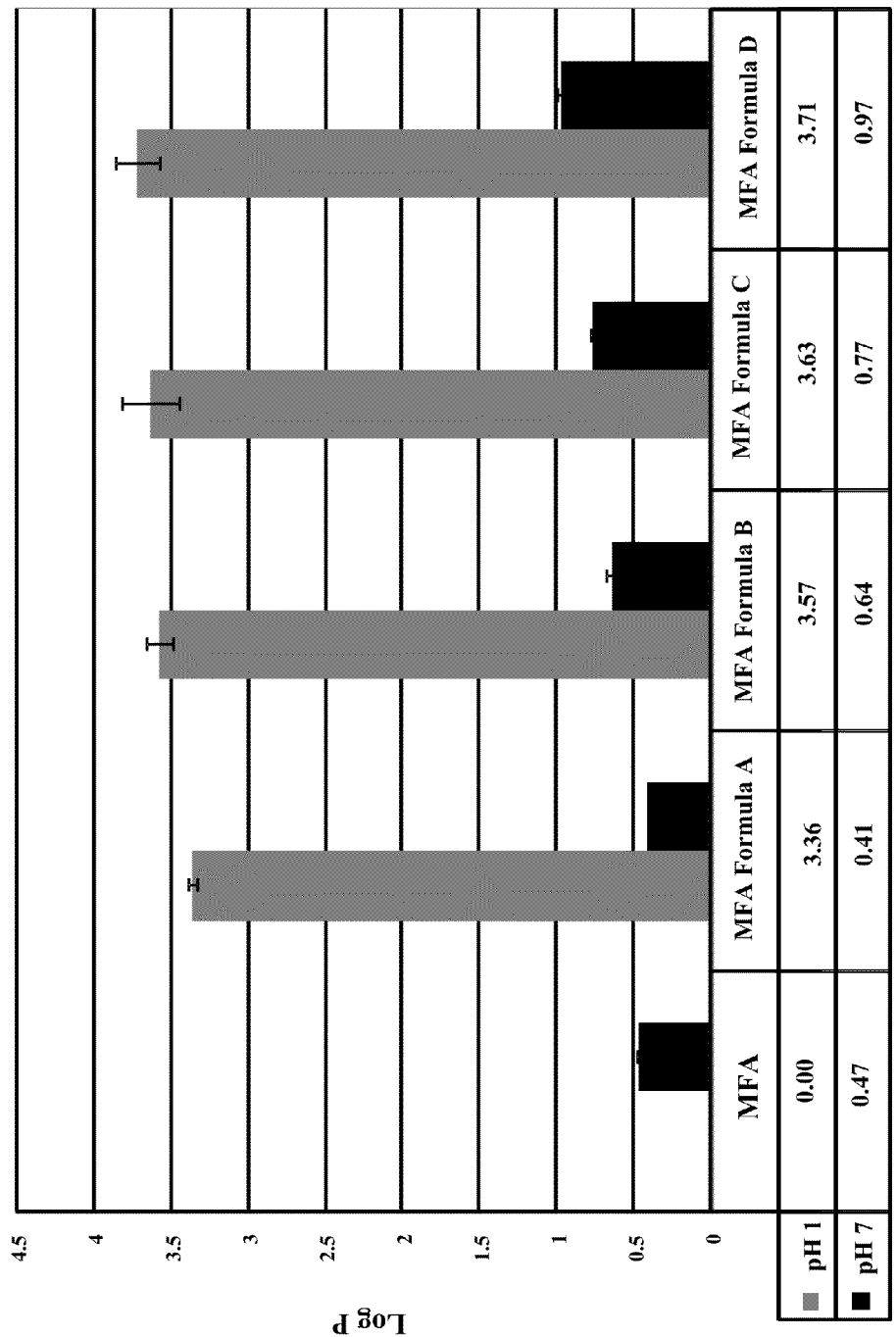

FIG. 20 depicts partitioning at pH 1 and at pH 7 for mefenamic acid (MFA) and in MFA Formulas A, C, E, and G.

DEFINITIONS OF TERMS

The following terms will have the meanings set forth below, which may or may not correspond to their generally accepted meaning:

General Terms

The term "mixture" means a blend of one or more ingredients, where the ingredients may interact at the molecular level, e.g., a homogeneous mixture is a mixture, where the ingredients are uniformly and homogeneously distributed, while an inhomogeneous mixture is a mixture, where the ingredients are not uniformly and homogeneously distributed.

The term "combination" means one or more ingredients that are combined, but not mixed.

The term "substantially" means that the attribute, condition or value is within about 10% of the indicated value. In other embodiments, the term is within about 5% of the indicated value. In other embodiments, the term is within about 2% of the indicated value. In other embodiments, the term is within about 1% of the indicated value.

The term "essentially free" or "substantially free" means compositions that include less than or equal to about 5 wt. % of a given ingredient. In certain embodiments, the terms means less than or equal to about 2 wt. %. In other embodiments, the terms means less than or equal to about 1 wt. %. In other embodiments, the terms means less than or equal to about 0.5 wt. %. In other embodiments, the terms means less than or equal to about 0.1 wt. %. In other embodiments, the terms means less than or equal to about 0.05 wt. %. In other embodiments, the terms means less than or equal to about 0.01 wt. %. In other embodiments, the terms means less than or equal to about 0.005 wt. %. In other embodiments, the terms means less than or equal to about 0.001 wt. %. In other embodiments, the terms means less than or equal to about 0.0005 wt. %. In other embodiments, the terms means less than or equal to about 0.0001 wt. %. Such ingredient may include, without limitation, water, solvents, or any other ingredient that is to be substantially excluded from the desired composition.

The term "relatively high concentration" means that the pharmaceutical or nutraceutical agents comprise greater than or equal to about 50 wt. % of the final composition. In certain embodiments, the term means that the pharmaceutical or nutraceutical agents comprise greater than or equal to about 55 wt. % of the final composition. In certain embodiments, the term means that the pharmaceutical or nutraceutical agents comprise greater than or equal to about 60 wt. % of the final composition. In certain embodiments, the term means that the pharmaceutical or nutraceutical agents comprise greater than or equal to about 65 wt. % of the final composition. In certain embodiments, the term means that the pharmaceutical or nutraceutical agents comprise greater than or equal to about 70 wt. % of the final composition. In certain embodiments, the term means that the pharmaceutical or nutraceutical agents comprise greater than or equal to about 75 wt. % of the final composition. In certain embodiments, the term means that the pharmaceutical or nutraceutical agents comprise greater than or equal to about 80 wt. % of the final composition. In certain embodiments, the term means that the pharmaceutical or nutraceutical agents comprise greater than or equal to about 85 wt. % of the final composition.

The term "major component" means a component present a composition in an amount of at least 33 wt. % based on 100 wt. % formulations.

The term "association complex" or "associated complex" means a non-covalent association between two or more compounds, where the compounds are held together by non-covalent chemical and/or physical interactions including hydrogen bonding, ionic bonding, dipolar interactions, hyperpolarizible interactions, van der Waals interaction, electrostatic interaction, apolar bonding or interaction, or any other chemical and/or physical attractive interaction. For example, NSAIDs and zwitterionic phospholipids form associated complexes.

The term "non-covalent interactions" means chemical and/or physical interactions including hydrogen bonding, ionic bonding, dipolar interactions, hyperpolarizible interactions, van der Waals interaction, electrostatic interaction, apolar bonding or interaction, or any other chemical and/or physical attractive interaction.

The term "hydrophilic" means a compound having a strong affinity for water; tending to dissolve in, mix with, or be wetted by water.

The term "hydrophobic" means a compound lacking affinity for water; tending to repel and not absorb water; tending not to dissolve in or mix with or be wetted by water.

The term "zwitterion" means a molecule that has a positively charged and a negatively charged functional group at biological pHs.

The term "anion" means a molecule that has an overall negative charge at biological pHs.

The term "cation" means a molecule that has an overall positive charge at biological pHs.

The term "relatively hydrophobic barriers" means any external, internal, cellular or sub-cellular barrier which has hydrophobic properties, which generally resists or reduces transport and/or partitioning of hydrophilic reagents across the barrier. Such barriers include, without limitation, a mucosal gel layer (e.g., gastric, duodenal, or colonic mucosal gel layers, vaginal mucosal gel layers, esophagus mucosal gel layers, nasal mucosal gel layers, lung mucosal gel layers, etc.), a plasma lemma (cellular membrane), the blood-brain barrier, placental barrier, testicular barrier, or any other barrier of a human, mammal or animal, through which partitioning and/or transporting of hydrophobic materials more easily occurs than hydrophilic materials.

The term "residual water" means water remaining in components used to make the compositions of this invention. Generally, the residual water comprise a small impurity in the components of the compositions of this invention.

The term "minimal residual water" means that the compositions of this invention include less than about 5 wt. % residual water. In certain embodiments, the compositions of this invention include less than about 4 wt. % residual water. In certain embodiments, the compositions of this invention include less than about 3 wt. % residual water. In certain embodiments, the compositions of this invention include less than about 2 wt. % residual water. In certain embodiments, the compositions of this invention include less than about 1 wt. % residual water.

The term "low moisture" means that the compositions only include residual water found in the components used to make the compositions of this invention.

The terms "modify, alter, and/or augment chemical and/or physical properties and/or behavior" means that the carriers of the present invention are designed to form hydrophobic matrices in which an active agent is mixed as a solid or liquid (depending on the nature of the active agent). These hydrophobic matrices operate to modify, alter or augment chemical and/or physical characteristics of the active agent by providing an immiscible/different environment compared to an aqueous biofluid such as blood, gastric fluids, duodenal fluids, small intestinal fluids, large intestinal fluids, vaginal fluids, rectal solids/fluids, or any other biofluid setting up a situation where the active agent is free to partition between the two immiscible environments. Additionally, properties of the carriers of this invention such as viscosity, lipophilicity, hydrophobicity, dispersibility, dispensibility, softening temperature, melting temperature, etc. also act to modify, alter or augment the rate of partitioning of the active agent by sequestering the active agent in the immiscible carrier until the carrier matrix is dispersed to small enough particles to facilitate mass transfer from the immiscible carrier to the biofluid. For solid active agents sequestered in a carrier matrix of this invention, an added reduction in partitioning rate ensues because the active agent must dissolve out of the matrix as the particle size of the matrix reduces in the biofluid due to mechanic actions of the tissue and/or organ and/or due to biochemical processes occurring in the tissue and/or organ.

The term "targeted manner" means that an active agent is targeted for release into a desired biological environment.

The term "pH dependent manner" means that pH affects how the carriers of the present invention operate to modify, alter or augment chemical and/or physical characteristics of the active agent by providing an immiscible/different environment compared to an aqueous biofluid such as blood, gastric fluids, duodenal fluids, small intestinal fluids, large intestinal fluids, vaginal fluids, rectal solids/fluids, or any other biofluid setting up a situation where the active agent is free to partition between the two immiscible environments. Additionally, properties of the carriers of this invention such as viscosity, lipophilicity, hydrophobicity, dispersibiliy, dispensibility, softening temperature, melting temperature, etc. also act to modify, alter or augment the rate of partitioning of the active agent by sequestering the active agent in the immiscible carrier until the carrier matrix is dispersed to small enough particles to facilitate mass transfer from the immiscible carrier to the biofluid. For solid active agents sequestered in a carrier matrix of this invention, an added reduction in partitioning rate ensues because the solid must dissolve out of the matrix as the particle size of the matrix reduces in the biofluid due to mechanic actions of the tissue and/or organ and/or due to biochemical processes occurring in the tissue and/or organ. Thus, the pH of the biofluid changes the rate at which the immiscible carrier matrix disperses in the biofluid and the mass transfer rates of the active agents out of the carrier matrix. For weak acid active agents and weak base active agents, the carrier may be designed to reduce release of the active agent until the pH of the biofluid is at or near (within about 1 pH unit or less) of the $pK_a$ or $pK_b$ of the active agent. For a weak acid active agent, the carrier reduces release of the active agent in low pH environments such as in gastric fluid, which showing increased release in pH environments at or near (within about 1 pH unit or less) of the $pK_a$ of the weak acid active agent.

The term "one or more", "at least one", "one . . . or a plurality of . . . " all mean a singular article or more than one articles.

Agents and Compounds

The term "active agent" or "biologically active agent" or "active ingredient" or "biologically active ingredient" means any pharmaceutical agent or any nutraceutical agent as defined by the United State Food and Drug Administration (FDA).

The term "pharmaceutical agent" means any compound or composition that has been or will be approved for human, mammal, and/or animal administration for treating some malady, disease, syndrome, dysfunction, etc.—generally drugs approved for example by the FDA.

The term "nutraceutical agent" means any compound or composition for human, mammal, and/or animal administration for nutritional supplementation or other uses.

The term "weak acid active agents" and "weak base active agents" are active agents that are only partially ionized in aqueous solutions and the extent of ionization depends on the pH of the aqueous solution.

The term "anti-inflammatory drugs" mean any of a variety of drugs that reduce or inhibit inflammation in tissue, organs, or the like. Anti-inflammatory drugs including non-steroidal, anti-inflammatory drugs (COX1 and/or COX2 inhibitors), drugs for treating irritable bowel disorder or disease (IBD) represents a family of ulcerative diseases including Ulcerative Colitis and Crohn's Disease that affect the colon and distal small bowel, and other drugs that have anti-inflammatory activity in humans, mammals and/or animals. The present targeted delivery systems may also find utility in treating conditions evidencing a pH imbalance in animal, mammals, and human GI, urinary, and reproductive tracts.

The term "NSAID" means any of a variety of drugs generally classified as non-steroidal, anti-inflammatory drugs, including, without limitation, ibuprofen, piroxicam, salicylate, aspirin, naproxen, indomethacin, diclofenac, COX2 inhibitors or any mixture thereof.

The term "oil" means any of numerous mineral, vegetable, and synthetic substances and animal and vegetable fats that are generally slippery, combustible, viscous, liquid, or liquefiable at room temperature, soluble in various organic solvents such as ether but not in water.

The term "lipid" means any of a group of organic compounds including fats, oils, waxes, sterols, mono-glycerides, di-glycerides, and triglycerides that are insoluble in water but soluble in nonpolar organic solvents and are oily to the touch.

The term "neutral lipid" (NL) means a non-charged, non-phosphoglyceride lipid including mono-glycerides, di-glycerides, triglycerides or mixture thereof. In some embodiments, the term neutral lipid refers exclusively to tri-glycerides (TGs).

The term "phospholipid" (PL) means any biocompatible phospholipid.

The term "zwitterionic phospholipid" means any phospholipid bearing a positive and an negative charge at biological pHs including, but not limited to, phosphatidylcholine, phosphatidylserine, phosphalidylethanolamine, sphingomyelin and other ceramides, as well as various other zwitterionic phospholipids.

The term "biocompatible" means being compatible with living cells, tissues, organs, or systems, and posing no, minimal, or acceptable risk of injury, toxicity, or rejection by the immune system of a human, mammal, or animal.

The term "biocompatible agent" means any compound that is compatible with living cells, tissues, organs, or systems, and posing no risk of injury, toxicity, or rejection by the immune system of a human, mammal, or animal. There are a number of classes of biocompatible agents suitable for use in the invention including hydrophobic biocompatible agents, biocompatible oils, pH dependent biocompatible release agents such as biocompatible fatty acids or biocompatible fatty polyacids, and lecithin oils.

The term "biocompatible oil" means any oil that is compatible with living cells, tissues, organs, or systems, and posing no risk of injury, toxicity, or rejection by the immune system of a human, mammal, or animal. In certain embodiments, biocompatible oils are any oil that has been approved for human consumption by the FDA or other governmental agents or approved for of a human, mammal, or animal consumption, where the compound may be a solid or liquid at room temperature or biological temperatures. In certain embodiments, the term means any oil that is a fluid at biological temperatures. In other embodiments, the term means any oil that is a fluid at room temperature.

The term "biocompatible fatty acid or biocompatible free fatty acid" means any fatty acid or free fatty acid (FFA) that is compatible with living cells, tissues, organs, or systems, and posing no risk of injury, toxicity, or rejection by the immune system of a human, mammal, or animal. In certain embodiments, biocompatible fatty acids are mono-carboxylic acids. In certain embodiments, the biocompatible fatty acids have at least 8 carbon atoms. In other embodiments, the biocompatible fatty acids have at least 10 carbon atoms. In other embodiments, the biocompatible fatty acids have at least 12 carbon atoms. In other embodiments, the biocompatible fatty acids have at least 14 carbon atoms. In other embodiments, the biocompatible fatty acids have at least 16 carbon atoms. In other embodiments, the biocompatible fatty acids have at least 18 carbon atoms. In certain embodiments, the biocompatible fatty acids may be unsaturated fatty acids. In certain embodiments, the biocompatible fatty acids may be saturated fatty acids. In certain embodiments, the biocompatible fatty acids may be a mixture of saturated and unsaturated fatty acids. The term "free fatty acid" is used sometimes as a term to fully distinguish between a fatty acid and a fatty acid ester of a mono-, di-, and tri-glyceride.

The term "biocompatible fatty acid ester" means any fatty acid ester that is compatible with living cells, tissues, organs, or systems, and posing no risk of injury, toxicity, or rejection by the immune system of a human, mammal, or animal. In certain embodiments, the biocompatible carboxylic acid esters are esters of mono-alcohols or polyols.

The term "biocompatible fatty acid salt" means any salt of a biocompatible carboxylic acid. In certain embodiments, the salts are salts of mono-carboxylic acids.

The term "biocompatible fatty poly acids" means any biocompatible compound having more than one carboxylic acid moiety per compound that is compatible with living cells, tissues, organs, or systems, and posing no risk of injury, toxicity, or rejection by the immune system of a human, mammal, or animal. In certain embodiments, the biocompatible poly acids have at least 8 carbon atoms. In other embodiments, the biocompatible poly acids have at least 10 carbon atoms. In other embodiments, the biocompatible poly acids have at least 12 carbon atoms. In other embodiments, the biocompatible poly acids have at least 14 carbon atoms. In other embodiments, the biocompatible poly acids have at least 16 carbon atoms. In other embodiments, the biocompatible fatty acids have at least 18 carbon atoms. In certain embodiments, the biocompatible fatty acids may be unsaturated fatty acids. In certain embodiments, the biocompatible fatty acids may be unsaturated fatty acids. In certain embodiments, the biocompatible fatty acids may be saturated fatty acids. In certain embodiments, the biocompatible fatty acids may be a mixture of saturated and unsaturated fatty acids.

The term "lecithin" means a yellow-brownish fatty substances derived from plant or animal and that is defined as complex mixture of acetone-insoluble phosphatides, which consist chiefly of phosphatidylcholine, phosphatidylethanolamine, phosphatidylserine, and phosphatidylinositol, combined with various amounts of other substances such as triglycerides, fatty acids, and carbohydrates, as separated from the crude vegetable oil source. It contains NLT 50.0% of acetone-insoluble matter. In certain embodiments, the lecithin may comprised of lipids esterified with unsaturated fatty acid side chains. In other embodiments, the lecithin may be comprised of lipids with saturated lipids. In other embodiments, the lecithin may be comprised of lipids with mixtures thereof.

The term "crude lecithin" means a lecithin containing having about 10-15 wt. % phosphatidylcholine.

The term "semi crude or triple strength lecithin" means a lecithin where the phosphatidylcholine content has been increased to 35 wt. % to about 50 wt %.

The term "lecithin oil" means a liquid lecithin where lecithin is solubilized in oil and/or a free fatty acid. In certain embodiments, this lecithin oil is a semi crude or triple strength lecithin solubilized in a triglyceride and/or a free fatty acid.

The term "a purified phospholipid" means a naturally extracted or synthetic phospholipid having a purity above at least 90 wt. % of phospholipids, a single compound, or a class of closely related phospholipids such as phosphatidylcholine, phosphatidylethanol amine, dipalmitoylphosphatidylcholine (DPPC), or other similar phospholipids. Purified phospholipids are not lecithin, but may be derived from lecithin through extraction and purification.

The term "targeted biocompatible release agent" or "targeted release agent" means an agent that controls the release of one or more active agents in a targeted manner, i.e., release the active agents into a particular tissue or organ depending on the tissue or organ's physiological environment.

The term "pH dependent biocompatible release agent" or "pH dependent release agent" means a targeted release agent that controls the release of one or more active agents in a pH dependent manner. For example, fatty acids having between about 8 and about 50 carbon atoms, or fatty polyacids having between about 12 and about 50 carbon atoms will release one or more active agents in a pH dependent manner, when a composition including a fatty acid or fatty polyacid is administered orally such that at a low pH, the active agent is retained in the carrier by the fatty acid or fatty polyacid, but is released as the composition exits the stomach and the pH raised to about pH 7 in the upper intestines. The pH dependent biocompatible release agents are a subclass of the general class of biocompatible agents and in particular, hydrophobic biocompatible agents.

The term "carrier" means a composition that is a base for active agents such as pharmaceutical and/or nutraceutical agents.

The term "hydrophobic carrier" means a composition that is a base for active agents such as pharmaceutical and/or nutraceutical agents, where the carrier including one or more or at least one hydrophobic biocompatible agents and where the carrier is immiscible in water.

The term "oil-based carrier" means an oil-based composition that is a base for active agents such as pharmaceutical and/or nutraceutical agents. The oil-based carriers comprises one or more biocompatible oils and/or biocompatible hydrophobic agents and is a water immiscible.

Methods of Administration

The term "internal administration", "internally administered" or "parenteral administration" means administration via any technique that administers a composition directly into the blood stream, a tissue site, an organ or the like without first passing through the digestive tract.

The term "oral administration" or "oral administered" means administration via mouth.

The term "topical administration" or "topically administered" means administration onto a surface such as the skin, a mucosal gel layer (e.g., vaginal, rectal, ophthalmical, etc.), a tissue and/or organ exposed during a surgical procedure, or any other exposed bodily tissue.

DETAILED DESCRIPTION OF THE INVENTION

The inventors have found that unique carriers may be prepared for biologically active agents such as pharmaceutical and/or nutraceutical agents, where the carriers include one or a plurality of biocompatible targeted release agents so that the carrier targets the release of the active agents to a specific portion or specific portion of a tract in an animal, mammal, or human such as the gastrointestinal (GI) tract, the urinary tract, the reproductive tract, or tissues such as ophthalmic tissue. The inventors have also found that the carriers may be designed to include a sufficient amount of at least one biocompatible pH sensitive or dependent release agent so that the carriers release the active agents such as pharmaceutical and/or nutraceutical agents in a pH dependent manner. The inventors have also found that pharmaceutical and/or nutraceutical compositions may be formulated including a carrier of this invention and an effective amount of at least one pharmaceutical agent and/or at least one nutraceutical agent, where the agents may be released in a targeted or tailored manner within a tract of the body such as the GI tract. The inventors have found that the carriers of this invention may include pH dependent release systems that release pharmaceutical and/or nutraceutical agents in a pH dependent manner targeting different portions of a tract of the body such as the GI tract and due to the hydrophobic nature of the carriers and/or the carrier components, improving the ability of the agents to partition across hydrophobic mucosal barriers or membranes in pH dependent manner. The compositions of this invention are also well suited for the delivery of biologically active ingredients in a pH dependent manner due to pH changes that occur in tissues, organs, or tracts in response to certain pre-disease or disease states.

As the population of the world and particularly the United States has increasing numbers of older citizens and citizens that are physically heavier than previous generations, the need for new delivery systems for biologically active agents that are known to have certain adverse effects such as adverse GI affects increases, especially for non-steroidal, anti-inflammatory drugs (NSAIDs). NSAIDs are ubiquitously used drugs for managing pain, for reducing or managing cardiovascular disease, for reducing platelet aggregation, for reducing fever, for reducing or preventing cancer, and for a number of other uses. However, NSAIDs have a major drawback, they all have, to some extent, the ability to cause irritation, erosion, and/or ulceration of the stomach and upper GI tract. In recent years, Lichtenberger and coworkers have demonstrated that associating NSAIDs with phospholipids are capable of greatly reducing the GI toxicity of certain NSAID such as aspirin and ibuprofen. However, compositions including high amount of NSAID and high amount of phospholipids are subject to breakdown over time due to hydrolysis, for aspirin, of the acetyl side chain and for phospholipids, of the fatty acid side chains. In an ongoing effort to construct improved delivery systems for NSAIDs and any other pharmaceutical and/or nutraceutical agents that requires targeted release or delivery of the NSAIDs or agents into desired portions of the GI tract, we have developed carrier systems that are immiscible with water and include at least one targeted release agent. We demonstrate herein that carrier including at least one targeted release agent may be used to delivery one or more active agents into different portions of the GI tract. For example, if a given active agent has a known adverse interaction with the stomach or other low pH biological environments, the carriers may be designed so that the active agent is not effectively released until the pH rises to a pH greater than about pH 3. In these carriers, the active agents release at pH values of less the pH 2 at a rate of less than about 20% in thirty minutes, while the active agents release at pH values above about pH 3 at a rate of greater than 80% in thirty minutes. These same targeted release carriers are also well-suited for acid sensitive active agents, where the release is designed for pH values greater the pH 5. We also demonstrate herein that carriers immiscible in water may be formulated for rapid release into low pH environments instead of releasing into higher pH environments. Thus, the carriers of this invention may be designed to release active agents to any pH environment and potentially to any given biological environment.

We have found that the targeted release agents are any compound that includes at least one ionizable group such as a carboxylic acid group, hydroxy group, amino group, amide groups, or other similarly ionizable groups, are immiscible in water or soluble in oils, and, for weak acids, have a pKa value greater than or equal to about pH 3.5. These targeted release agents are neutral and pH values below their pKa values, especially at pH values less than pH 2, and become ionized at pH values above their pKa values. Thus at low pH (<pH 2), the targeted release agents behave simply as oils remaining immiscible in aqueous fluids and evidence minimal release of active agent in low pH fluid environments. But as the pH rises, the release agents become ionized and now act as active surfactants causing a rapid dissolution of the carrier including the active agent in higher pH environments. Because the GI tract has a pH profile starting at the stomach and proceeding to the large intestines of increasing pH from a pH value in the stomach of about pH 1 and about pH 3 to a pH in the duodenum between about pH 3 and pH 5 to pH values as high as pH 8 in the large intestines, using release agents having different pKa values, we can design a carrier that will efficiently and rapidly release an active agent only when the pH of the environment is at or greater than the pKa value of the release agents. We have also found that carriers of this invention may include from just a sufficient amount of the release agents to 100% of release agents. We have also found that other components such as neutral lipids, zwitterionic surfactants, excipients, and/or adjuvants may be added to the carrier without significantly or adversely affecting the release properties of the carrier. Thus, carriers including 100% of the release agents evidence similar partitioning profiles, dissolution profiles, and in vivo efficacies compared to carriers with small amounts or large amount of other components including neutral lipids and phospholipids.

We have found that fatty acids represent one class of targeted release agents that are immiscible in water and have pKa values generally greater than about pH 3 and are converted to surfactants through ionization at pH values at or above their pKa values. We have also discovered that carriers may be tested to determine their potential use as targeted release carriers using partitioning studies of the carrier/active agent compositions in bi-phasic systems, where one of the phases represent a low pH or aqueous environment and the other phase represents a hydrophobic environment. The partitioning data provides predictive information about the ability for a given carrier to release a given active agent at a given pH. We have also discovered that compositions including a targeted release carrier of this invention and a given active agent may be tested for pH dependent release characteristic by studying the release properties of the composition is various dissolution media, especially dissolution media having different pH values so that the dissolution of the active agent may be determined from pH 1 to pH 7 or higher. The dissolution profiles provide in vitro data to predict the release characteristics a given system.

Embodiments of the present invention relates to compositions comprising: (1) a carrier including a sufficient amount of a pH dependent release system, and (2) at least one biologically active agent, where the carrier releases the biologically active agents in a pH sensitive manner characterized in that less than 20% of the biologically active agents are released into a gastric fluid and greater than 50% of the biologically active agents are released in an intestinal fluid having a pH value greater than pH 3.

Embodiments of the present invention relates to compositions comprising: (1) a carrier including a sufficient amount of a pH dependent release system, and (2) at least one biologically active agent, where the carrier releases the biologically active agents in a pH sensitive manner characterized in that the biologically active agents are released minimally into stomach and efficiently released into an intestinal region.

Embodiments of the present invention relates to compositions comprising: (1) a carrier including a sufficient amount of a pH dependent release system, and (2) at least one biologically active agent, where the carrier releases the biologically active agents in a pH sensitive manner characterized in that the biologically active agents are released minimally at a first pH and efficiently released at second pH.

Embodiments of the present invention relates to compositions comprising: (1) a carrier including a sufficient amount of a pH dependent release system, and (2) at least one biologically active agent, where the carrier releases the biologically active agents in a pH sensitive manner characterized in that the biologically active agents are released minimally into stomach and efficiently released into an intestinal region having different concentrations and/or types of bile acids and/or digestive enzymes.

In certain embodiments, the pH sensitive manner is characterized by differential release of the active agents into gastric fluid and intestinal fluid. In other embodiments, the biologically active agents are substantially non-ionized at gastric fluid pH and become ionized as the pH increases. In other embodiments, the pH dependent release system comprising a fatty acid or a plurality of fatty acids having at least 8 carbon atoms. In other embodiments, the biologically active agents are selected from the group consisting of weak acid biologically active agents, weak base biologically active agents, and mixtures or combinations thereof. In other embodiments, the weak acid biologically active agents are selected from the group consisting of a weak acid non-steroidal anti-inflammatory drugs (NSAID) and mixtures of NSAIDs.

Embodiments of the present invention relates to pharmaceutical compositions comprising a carrier including a sufficient amount of a pH dependent release system, and at least one weak acid non-steroidal anti-inflammatory drug (NSAID), where the carrier releases the NSAIDs in a pH sensitive manner characterized in that less than 20% of the biologically active agents are released into gastric fluid and greater than 50% of the biologically active agents are released in intestinal fluid having a pH value greater than pH 3, and where the biologically active agents are substantially non-ionized at gastric fluid pH and become ionized as the pH increases. In other embodiments, the pH dependent release system comprising of a fatty acid or a plurality of fatty acids having at least 8 carbon atoms.

Embodiments of the present invention relates to pharmaceutical compositions comprising a suspension of a weak acid non-steroidal anti-inflammatory drug (NSAID) agent or mixture of NSAIDs in a carrier comprising a sufficient amount of a pH dependent release system.

Embodiments of the present invention relates to pharmaceutical compositions comprising a suspension of a weak acid non-steroidal anti-inflammatory drug (NSAID) agent or mixture of NSAIDs in a carrier comprising a sufficient amount of at least one fatty acid having at least 8 carbon atoms.

Embodiments of the present invention relates to methods of targeting a biologically active agent along the gastrointestinal (GI) tract comprising the step of orally administering a composition comprising a carrier including a sufficient amount of a pH dependent release system, and at least one biologically active agent, where the carrier releases the biologically active agents in a pH sensitive manner characterized in that less than 20% of the biologically active agents are released into gastric fluid and greater than 50% of the biologically active agents are released in intestinal fluid having a pH value greater than pH 3, and where the biologically active agents are uncharged at gastric fluid pH and charged at pH values greater than pH 3 or are unstable in fluids having a pH less than pH 3.

Embodiments of the present invention relates to carrier compositions comprising a least one biocompatible targeted release agent, where the carrier composition and/or its components are capable of controllably releasing at least one active agent into certain portions of the gastro-intestinal (GI) tract. In other embodiments, the biocompatible targeted release agents comprise pH dependent release agents capable of controllably releasing the active agents in a pH dependent manner. In other embodiments, the biocompatible targeted release agents comprise pH dependent release agents capable of controllably releasing the active agents into certain portions of the GI tract based on a pH of the portions. In other embodiments, the pH dependent release agents include biocompatible fatty acid having at least 8 carbon atoms. In other embodiments, the carrier further comprising at least one neutral lipid, where the neutral lipid is water immiscible. In other embodiments, the neutral lipids comprise mono-glycerides, diglycerides, triglycerides, or mixtures and combinations thereof, where the ester side chains have at least 6 carbon atoms. In other embodiments, carrier further comprising less than 10 wt. % of a phospholipid or a plurality of phospholipids.

Embodiments of the present invention relates to carrier compositions comprising 100 wt. % of at least one biocompatible fatty acid having at least 8 carbon atoms, and 0 wt. % to 100 wt. % at least one neutral lipid, where the carrier composition and/or its components are capable of controllably releasing at least one active agent into certain portions of the gastro-intestinal (GI) tract and where the wt. % may add to a value greater than 100. In other embodiments, the carrier composition further comprising less than 10 wt. % of a phospholipid. In other embodiments, the carrier composition further comprising less than 5 wt. % of a phospholipid. In other embodiments, carrier composition further comprising less than 2.5 wt. % of a phospholipid.

Embodiments of the present invention relates to compositions comprising a carrier including a least one biocompatible targeted release agent, and an effective amount of at least one biologically active agent, where the carrier composition and/or its components are capable of controllably releasing at least one active agent into certain portions of the gastro-intestinal (GI) tract. In other embodiments, the carrier and/or its components modify and/or alter the chemical and/or physical properties and/or behavior of the at least one active agent in tissues and/or organs reducing and/or altering tissue and/or organ toxicity, improving and/or altering bioavailability, and/or improving and/or altering efficacy. In other embodiments, the carrier is capable of releasing the at least one active agent in a pH dependent manner. In other embodiments, the biocompatible targeted release agent comprise at least one biocompatible fatty acid having at least 8 carbon atoms.

Embodiments of the present invention relates to compositions comprising a carrier including 100 wt. % of at least one biocompatible fatty acid having at least 8 carbon atoms, and 0 wt. % to 100 wt. % at least one neutral lipid, where the neutral lipid is immiscible in water, where the wt. % may add to a value greater than 100, and an effective amount of at least one biologically active agent, where the carrier composition and/or its components are capable of controllably releasing at least one active agent into certain portions of the gastro-intestinal (GI) tract. In other embodiments, the carrier and/or its components modify and/or alter the chemical and/or physical properties and/or behavior of the at least one active agent in tissues and/or organs reducing and/or altering tissue and/or organ toxicity, improving and/or altering bioavailability, and/or improving and/or altering efficacy. In other embodiments, the carrier further including less than 10 wt. % of a phospholipid. In other embodiments, the carrier further including less than 5 wt. % of a phospholipid. In other embodiments, the carrier further including less than 2.5 wt. % of a phospholipid.

Embodiments of the present invention relates to compositions comprising a carrier including 100 wt. % of at least one biocompatible fatty acid having at least 8 carbon atoms, and 0 wt. % to 100 wt. % at least one neutral lipid, where the neutral lipid is immiscible in water, where the wt. % may add to a value greater than 100, and an effective amount of at least one biologically active agent, where the carrier composition and/or its components are capable of controllably releasing at least one active agent into certain portions of the gastro-intestinal (GI) tract. In other embodiments, the carrier and/or its components modify and/or alter the chemical and/or physical properties and/or behavior of the at least one active agent in tissues and/or organs reducing and/or altering tissue and/or organ toxicity, improving and/or altering bioavailability, and/or improving and/or altering efficacy. In other embodiments, the carrier further including less than 10 wt. % of a phospholipid. In other embodiments, the carrier further including less than 5 wt. % of a phospholipid. In other embodiments, the carrier further including less than 2.5 wt. % of a phospholipid.

Embodiments of the present invention relates to compositions comprising a carrier including less than 8 wt. % of at least one biocompatible fatty acid having at least 8 carbon atoms or greater than 14 wt. % of at least one biocompatible fatty acid having at least 8 carbon atoms, and from 0 wt. % to 100 wt. % at least one neutral lipid, where the neutral lipid is immiscible in water, and from 0 wt. % to 100 wt. % of a least one phospholipids, where the wt. % may add to a value greater than 100, and an effective amount of at least one biologically active agent, where the carrier composition and/or its components are capable of controllably releasing at least one active agent into certain portions of the gastrointestinal (GI) tract. In other embodiments, the carrier and/or its components modify and/or alter the chemical and/or physical properties and/or behavior of the at least one active agent in tissues and/or organs reducing and/or altering tissue and/or organ toxicity, improving and/or altering bioavailability, and/or improving and/or altering efficacy.

Carriers

Embodiments of the present invention relates broadly to carrier compositions including at least one biocompatible targeted release agent. The carriers and/or their components modify and/or alter the chemical and/or physical properties and/or behavior of at least one active agent in tissues and/or organs reducing and/or altering tissue and/or organ toxicity, improving and/or altering bioavailability, and/or improving and/or altering efficacy. In certain embodiments, the carriers and/or their components modify and/or alter the chemical and/or physical properties and/or behavior of at least one active agent in tissues and/or organs in a pH dependent manner to reduce and/or alter tissue and/or organ toxicity, improve and/or alter bioavailability, and/or improve and/or alter efficacy. In certain embodiments, the biocompatible agents are hydrophobic.

The present invention relates broadly to carriers for active agents including: (1) a biocompatible fatty acid or a plurality of biocompatible fatty acids, (2) optionally a biocompatible fatty acid ester or a plurality of biocompatible fatty acid esters, (3) optionally a biocompatible oil or a plurality of biocompatible oils, (4) optionally a biocompatible fatty acid salt or a plurality of biocompatible fatty acid salts, (5) optionally a secondary complexing agent, and (6) optionally a protective system including agents to reduce and/or eliminate toxicities, irritations or side-effects. The carriers are generally viscous fluids capable of being orally administered, directly administered, internally administered and/or topically administered.

In certain embodiments, the carriers of this invention may also include other components such as: (1) excipients, (2) adjuvants, (3) drying agents, (4) antioxidants, (5) preservatives, (6) chelating agents, (7) viscomodulators, (8) tonicifiers, (9) flavorants and taste masking agents, (10) colorants, (11) odorants, (12) opacifiers, (13) suspending agents, (14) binders, and (15) mixtures thereof.

The carries are generally viscous fluids and the composition made therefrom are generally solutions, pastes, semisolids, dispersions, suspensions, colloidal suspensions or mixtures thereof and are capable of being orally administered, parenterally administered or topically administered.

Fatty Acid Targeted Releases Agents

We also believe that the carriers and/or their components interact with certain types of active agents to affect particle size, morphology, other physical characteristics, physical/chemical properties and/or behavior and physical/chemical properties of the crystals of the active agent in the carrier. In certain embodiments, the active agents are added to the carrier at an elevated temperature, where the temperature may be up to the melting temperature of the active ingredient, but below a decomposition temperature of any of the carrier components or active ingredients. The inventors believe that the augmented properties result in increased bioavailability of the active agent once the pH of the environment is at or near the $pK_a$ or $pK_b$ of the pH dependent release agents and/or the active agents.

Secondary Complexing Agents

Embodiments of the carrier compositions may also include at least one secondary agent capable of interacting with the active agents added to the carrier. Embodiments of the carrier compositions may also include a secondary anti-toxicity system designed to reduce toxic side effects of the active agents. Embodiments of these carrier compositions are generally water free or essentially or substantially water free and/or solvent free or essentially or substantially solvent free. Being oils, the carriers are water immiscible. We have found that therapeutic compositions may be prepared by adding at least one therapeutically active agent to a carrier of this invention with tailored properties, where the therapeutically active agent includes pharmaceutical agents and/or nutraceutical agents. We have also found that pharmaceutical compositions may be prepared by adding at least one pharmaceutical agent to a carrier of this invention under conditions to form a pharmaceutical composition having tailored properties. The inventors have also found that nutraceutical compositions may be prepared by adding at least one nutraceutical agent to a carrier of this invention to form a nutraceutical composition having tailored properties. Embodiments of these compositions are water free or essentially water free and/or solvent free or essentially solvent free, i.e., the compositions are immiscible in biofluids in a pH dependent manner.

For pharmaceutical agents that have GI toxicity, the carriers of this invention may also include neutral lipids and/or phospholipids, e.g., non-steroidal, anti-inflammatory drugs (NSAIDs) as the pharmaceutical agents, where the neutral lipids and/or phospholipids are known to reduce the pathogenic effects of the NSAIDs, such as GI ulceration, bleeding, liver damage, kidney damage, and/or cardiovascular disease and/or side-effects such as; high blood pressure, atherosclerosis, thrombosis, angina pectoralis, strokes and myocardial infarction. In certain embodiments, the carriers of this invention include free fatty acid (FFA) carriers in the absence or present of phospholipids, where the phospholipids reduce and/or eliminate pharmaceutical and/or nutraceutical toxicities, irritations or side-effects of certain pharmaceutical and/or nutraceutical agents such as NSAIDs, while the phospholipid free carriers afford direct targeted release of the NSAID resulting in released GI toxic side effects.

Compositions

Embodiments of the present invention relates broadly to compositions including a carrier of this invention and an effective amount of at least one active agent in the presence or absence of at least one secondary agent for the active agents or protective agents for the active agents. In certain embodiments, the carriers of this invention are non-aqueous including only residual water and are immiscible in water or aqueous solutions, but are capable of being dispersed in aqueous solutions releasing the active agent in a pH dependent manner. In other embodiments, the carriers of this invention are oil-based including only residual water and are immiscible in water or aqueous solutions, but are capable of being dispersed in aqueous solutions releasing the active agent.

In certain embodiments, the carriers of this invention may be tailored to have good targeted active agent release characteristics, to have reduced active agent toxicity or irritation, to have increased active agent bioavailability, and to have increased active agent migration across relatively hydrophobic barriers in a human, mammal or animal.

In other embodiments, the carriers of this invention may be tailored to have good targeted active agent release characteristics, to have reduced active agent GI toxicity or irritation, to have increased active agent bioavailability, and to have increased active agent migration across relatively hydrophobic barriers in a human, mammal or animal.

Pharmaceutical and Nutraceutical Compositions

Embodiments of the present invention relates broadly to pharmaceutical compositions including a carrier of this invention and an effective amount of a pharmaceutical agent or a mixture of pharmaceutical agents to form a solution and/or a suspension of the pharmaceutical agent or the mixture of pharmaceutical agents in the carrier. In certain embodiments, the pharmaceutical compositions may be tailored to have good targeted pharmaceutical release characteristics, to have reduced pharmaceutical toxicity or irritation, to have increased pharmaceutical bioavailability, and to have increased pharmaceutical migration across relatively hydrophobic barriers in a human, mammal or animal. In other embodiments, the pharmaceutical compositions may be tailored to have good targeted pharmaceutical release characteristics, to have reduced pharmaceuticals GI toxicity or irritation, to have increased pharmaceutical bioavailability, and to have increased pharmaceutical migration across relatively hydrophobic barriers in a human, mammal or animal.

Embodiments of the present invention relates broadly to nutraceutical compositions including a carrier of this invention and an effective amount of a nutraceutical agent or a mixture of nutraceutical agents to form a solution and/or a suspension of the nutraceutical agent or a mixture of nutraceutical agents in the carrier. In certain embodiments, the nutraceutical compositions may be tailored to have good targeted nutraceutical release characteristics, to have reduced nutraceutical toxicity or irritation, to have increased nutraceutical bioavailability, and to have increased nutraceutical migration across relatively hydrophobic barriers in a human, mammal or animal. In other embodiments, the nutraceutical compositions may be tailored to have good targeted nutraceutical release characteristics, to have reduced nutraceutical GI toxicity or irritation, to have increased nutraceutical bioavailability, and to have increased nutraceutical migration across relatively hydrophobic barriers in a human, mammal or animal.

In other embodiments, the pharmaceutical agent is an NSAID. In other embodiments, the NSAID compositions of this invention may also include: (1) a pharmaceutically acceptable amount of antioxidant selected from the group consisting of Vitamin A, Vitamin C, Vitamin E or other antioxidants approved for a human, mammal or animal consumption by the FDA and mixtures or combinations thereof; (2) a pharmaceutically acceptable amount of a polyvalent cation selected from the group consisting of copper, zinc, gold, aluminum and calcium and mixtures or combinations thereof; (3) a pharmaceutically acceptable amount of an agent to promote fluidity, enhance viscosity, promote spreadability, promote dispersibility and/or promote permeability selected from the group consisting of dimethylsulfoxide (DMSO), propylene glycol (PPG), and medium chain triglyceride/ MCT and mixtures or combination thereof; (4) a pharmaceutically acceptable amount of a food coloration or non-toxic dye; (5) a pharmaceutically acceptable amount of a flavor enhancer; (6) an excipient; and/or (7) an adjuvant.

In other embodiments, the pharmaceutical and/or nutraceutical agent is acid labile. The carriers may be tailored to selectively minimize release of the acid labile active agents in the stomach and selectively target release of the acid labile active agent to the small intestines or the large intestines. This embodiment could be especially useful for patients at risk for cardiovascular (CV) disease and acid reflux disease, or an elevated risk of gastrointestinal bleeding that require the use of a proton pump inhibitor including but not limited to omeprazole or lansoprazole.

Compositions for Treating

Embodiments of the present invention relates broadly to methods including administering a composition of this invention to a human, mammal or animal. The carriers may be tailored so that the compositions have good pharmaceutical and/or nutraceutical release characteristics, have reduced pharmaceutical and/or nutraceutical toxicity or irritation, have increased pharmaceutical and/or nutraceutical bioavailability and have increased pharmaceutical or nutraceutical availability across relatively hydrophobic barriers in a human, mammal or animal. For example, pharmaceuticals and/or nutraceuticals that have GI toxicity and/or GI irritation, the carriers of this invention may be tailored to ameliorate, reduce or eliminate the GI toxicity and/or GI irritation of the pharmaceuticals and/or nutraceuticals. In certain embodiments, the pharmaceutical and/or nutraceutical agents reduce, ameliorate or treat inflammation. In other embodiments, the pharmaceutical and/or nutraceutical agents reduce, ameliorate or treat platelet aggregation. In other embodiments, the pharmaceutical and/or nutraceutical agents reduce, ameliorate or treat pyretic activity. In other embodiments, the pharmaceutical and/or nutraceutical agents reduce, ameliorate or treat ulcerated regions of the tissue. Of course, the pharmaceutical and/or nutraceutical agents reduce, ameliorate or treat combinations of these symptoms as well.

Methods for Making the Carriers and Compositions

Embodiments of the present invention relates broadly to methods for making the carriers of this invention by mixing (1) a biocompatible fatty acid or a plurality of biocompatible fatty acids, (2) optionally a biocompatible fatty acid ester or a plurality of biocompatible fatty acid esters, (3) optionally a biocompatible oil or a plurality of biocompatible oils, (4) optionally a biocompatible fatty acid salt or a plurality of biocompatible fatty acid salts, (5) optionally a secondary complexing agent, and (6) optionally a protective system including agents to reduce and/or eliminate toxicities, irritations or side-effects, under conditions of temperature, pressure and time sufficient to form a carrier having tailored properties. The advantage of the admixing methods is there is not solvent required in preparation and thereby solvent removal.

Embodiments of the present invention also relates broadly to methods for making the carriers of this invention by mixing, in the presence of a solvent system, (1) a biocompatible fatty acid or a plurality of biocompatible fatty acids, (2) optionally a biocompatible fatty acid ester or a plurality of biocompatible fatty acid esters, (3) optionally a biocompatible oil or a plurality of biocompatible oils, (4) optionally a biocompatible fatty acid salt or a plurality of biocompatible fatty acid salts, (5) optionally a secondary complexing agent, and (6) optionally a protective system including agents to reduce and/or eliminate toxicities, irritations or side-effects, under conditions of temperature, pressure and time sufficient to form a carrier having tailored properties, followed by removal of solvent system. We have demonstrated that the behavior of the compositions are unaffected by the preparation with or within solvent.

In certain embodiments, the carriers are generally prepared at room temperature, at atmospheric pressure with mixing for a time sufficient to render the carrier uniform and/or homogeneous or substantially uniform and/or substantially homogeneous. However, the carrier may be prepare and higher or lower pressures. In other embodiments, the mixing may be performed at an elevated temperature up to a melting point of the highest melting component, but below a decomposition temperature of any of the carrier components. In other embodiments, the temperature is elevated to a temperature up to about 130° C. In other embodiments, the temperature is elevated to a temperature up to about 80° C. In other embodiments, the temperature is elevated to a temperature up to about 60° C. In other embodiments, the temperature is elevated to a temperature up to about 40° C.

In certain embodiments, the pressure at or near atmospheric pressure. In other embodiments, the pressure is above atmospheric pressure. In other embodiments, the pressure is below atmospheric pressure.

In certain embodiments, the time is for a period between about 5 minutes and about 12 hours. In other embodiments, the time is for a period between about 10 minutes and about 8 hours. In other embodiments, the time is for a period between about 20 minutes and about 4 hours. In other embodiments, the time is for a period between about 30 minutes and about 2 hours. In other embodiments, the time is for a period between about 30 minutes and about 1 hour.

In certain embodiments, the mixing is performed by low shear mixing such as paddle mixers. In other embodiments, the mixing is performed by high shear mixing such as extruders, internal mixers, etc. In certain embodiments, the mixing is performed by a combination of low shear mixing and high shear mixing. In certain embodiments, the mixing is performed by sonication with or without low shear and/or high shear mixing. In certain embodiments, the mixing is performed by vortex mixing in the presence or absence of sonication.

Embodiments of the present invention relates broadly to methods for making the compositions of this invention by mixing a carrier of this invention and an effective amount of at least one active agent under conditions of temperature, pressure and time sufficient to form a composition having tailored properties. In certain embodiments, the compositions may also include a secondary complexing agent for the active agent under conditions of temperature, pressure and time sufficient to form a composition having tailored properties in the presence or absence of a solvent system. If solvent system is used, then the system is generally removed prior to use. In certain embodiments, the compositions may also include a protective agent for the active agents. In certain embodiments, the active agents include pharmaceutical agents, nutraceutical agent or mixtures and combinations thereof. In certain embodiments, the compositions are made at room temperature, at atmospheric pressure with mixing until the carrier is uniform and/or homogeneous. In other embodiments, the mixing may be performed at an elevated temperature up to a melting point of the highest melting component, but below a decomposition temperature of any of the carrier components. In other embodiments, the temperature is elevated to a temperature up to about 130° C. In other embodiments, the temperature is elevated to a temperature up to about 80° C. In other embodiments, the temperature is elevated to a temperature up to about 60° C. In other embodiments, the temperature is elevated to a temperature up to about 40° C. In certain embodiments, the pressure at or near atmospheric pressure. In other embodiments, the pressure is above atmospheric pressure. In other embodiments, the pressure is below atmospheric pressure. In certain embodiments, the time is for a period between about 5 minutes and about 12 hours. In other embodiments, the time is for a period between about 10 minutes and about 8 hours. In other embodiments, the time is for a period between about 20 minutes and about 4 hours. In other embodiments, the time is for a period between about 30 minutes and about 2 hours. In other embodiments, the time is for a period between about 30 minutes and about 1 hour. In certain embodiments, the mixing is performed by low shear mixing such as paddle mixers. In other embodiments, the mixing is performed by high shear mixing such as extruders, internal mixers, etc. In certain embodiments, the mixing is performed by a combination of low shear mixing and high shear mixing. In certain embodiments, the mixing is performed by sonication with or without low shear and/or high shear mixing. In certain embodiments, the mixing is performed by vortex mixing in the presence or absence of sonication. Of course, the compositions may be prepared by mixing the active agents and the carrier components in any order, thus, the carrier does not have to be pre-made prior to adding the active agents. Additionally, the order of addition is not critical and may vary depending on components, mixers, desired final properties, or operator choice.

Methods for Using the Carriers and Compositions

Embodiments of the present invention relates broadly to methods for using the compositions of this invention by administering a composition of this invention to a human, a mammal or an animal at a dose sufficient to illicit at least one therapeutic effect such as treatment and/or prevention of pain, fever, inflammation, cancer, inflammatory bowel syndrome, crones disease, cardiovascular disease, infections, brain and spinal cord injury, Alzheimer's disease, other neurologic diseases diabetes, and/or any other disease or malady treatable via the administration of an active agent such as a pharmaceutical and/or nutraceutical agents. In other embodiments, the compositions treat, prevent and/or ameliorate symptoms of diseases and/or maladies.

Embodiments of the present invention relates broadly to methods including orally or internally administering a composition including a carrier of this invention and a therapeutically effective amount of a composition of this invention to increase transport of the pharmaceutical or nutraceutical agent across the blood-brain barrier or into the central nervous system (CNS) or peripheral nervous system (PNS) allowing more pharmaceutical or nutraceutical agent to get to the trauma site and reduce inflammation, platelet aggregation, pain (nociceptive) sensation, cell death and/or apoptosis due to inflammation and/or inducing competitive cell death of cancer cells in preventing or treating cancers.

Embodiments of the present invention relates broadly to methods including orally or internally administering a composition including a carrier of this invention and a therapeutically effective amount of a composition of this invention to prevent, treat and/or ameliorate symptoms associated with Alzheimer's disease.

Compositional Ranges Used in the Invention

Carriers

General Carriers

The carriers of this invention may include:
(1) 100 wt. % of at least one biocompatible agent,
(2) from about 0 wt. % to 100 wt. % of a secondary complexing agent or a mixture of secondary complexing agents, where the secondary complexing agents depends on the nature of the active agent to be carried by the carrier,
(3) from about 0 wt. % to about 50 wt. % of a secondary anti-toxicity agent or a mixture of secondary anti-toxicity agents, where the secondary anti-toxicity agents depends on the nature of the active agent to be carried by the carrier, and
(4) from about 0 wt. % to about 50 wt. % of (a) an excipient or a mixture of excipients, (b) an adjuvant or a mixture of adjuvants, (c) a drying or a mixture of drying agents, (d) a antioxidant or a mixture of antioxidants, (e) a preservative or a mixture of preservatives, (f) or a mixture of chelating agents, (g) a viscomodulator or a mixture of viscomodulators, (h) a tonicifier or a mixture of tonicifiers, (I) a flavorant or a mixture of flavorants, (j) a colorant or a mixture of colorants, (k) a odorant or a mixture of odorants, (l) a opacifier or a mixture of opacifiers, (m) a suspending agent or a mixture of suspending agents, and (n) mixtures thereof.

The carriers of this invention may include:
(1) 100 wt. % of at least two biocompatible agents,
(2) from about 0 wt. % to 100 wt. % of a secondary complexing agent or a mixture of secondary complexing agents, where the secondary complexing agents depends on the nature of the active agent to be carried by the carrier,
(3) from about 0 wt. % to about 50 wt. % of a secondary anti-toxicity agent or a mixture of secondary anti-toxicity agents, where the secondary anti-toxicity agents depends on the nature of the active agent to be carried by the carrier, and
(4) from about 0 wt. % to about 50 wt. % of (a) an excipient or a mixture of excipients, (b) an adjuvant or a mixture of adjuvants, (c) a drying or a mixture of drying agents, (d) a antioxidant or a mixture of antioxidants, (e) a preservative or a mixture of preservatives, (f) or a mixture of chelating agents, (g) a viscomodulator or a mixture of viscomodulators, (h) a tonicifier or a mixture of tonicifiers, (I) a flavorant or a mixture of flavorants, (j) a colorant or a mixture of colorants, (k) a odorant or a mixture of odorants, (l) a opacifier or a mixture of opacifiers, (m) a suspending agent or a mixture of suspending agents, and (n) mixtures thereof.

The above compositions are not formulated to have a total of 100 wt. % of the mixture of the indicated components.

pH Dependent Carriers

The carriers of this invention may include:
(1) 100 wt. % of at least one pH dependent biocompatible release agent,
(2) from about 0 wt. % to 100 wt. % of a secondary complexing agent or a mixture of secondary complexing agents, where the secondary complexing agents depends on the nature of the active agent to be carried by the carrier,
(3) from about 0 wt. % to about 50 wt. % of a secondary anti-toxicity agent or a mixture of secondary anti-toxicity agents, where the secondary anti-toxicity agents depends on the nature of the active agent to be carried by the carrier, and
(4) from about 0 wt. % to about 50 wt. % of (a) an excipient or a mixture of excipients, (b) an adjuvant or a mixture of adjuvants, (c) a drying or a mixture of drying agents, (d) a antioxidant or a mixture of antioxidants, (e) a preservative or a mixture of preservatives, (f) or a mixture of chelating agents, (g) a viscomodulator or a mixture of viscomodulators, (h) a tonicifier or a mixture of tonicifiers, (I) a flavorant or a mixture of flavorants, (j) a colorant or a mixture of colorants, (k) a odorant or a mixture of odorants, (l) a opacifier or a mixture of opacifiers, (m) a suspending agent or a mixture of suspending agents, and (n) mixtures thereof.

The carriers of this invention may include:
(1) 100 wt. % of at least one pH dependent biocompatible release agent,
(2) from about 0 wt. % to 100 wt. % of at least one other biocompatible agent,
(3) from about 0 wt. % to 100 wt. % of a secondary complexing agent or a mixture of secondary complexing agents, where the secondary complexing agents depends on the nature of the active agent to be carried by the carrier,
(4) from about 0 wt. % to about 50 wt. % of a secondary anti-toxicity agent or a mixture of secondary anti-toxicity agents, where the secondary anti-toxicity agents depends on the nature of the active agent to be carried by the carrier, and
(5) from about 0 wt. % to about 50 wt. % of (a) an excipient or a mixture of excipients, (b) an adjuvant or a mixture of adjuvants, (c) a drying or a mixture of drying agents, (d) a antioxidant or a mixture of antioxidants, (e) a preservative or a mixture of preservatives, (f) or a mixture of chelating agents, (g) a viscomodulator or a mixture of viscomodulators, (h) a tonicifier or a mixture of tonicifiers, (I) a flavorant or a mixture of flavorants, (j) a colorant or a mixture of colorants, (k) a odorant or a mixture of odorants, (l) a opacifier or a mixture of opacifiers, (m) a suspending agent or a mixture of suspending agents, and (n) mixtures thereof.

The above compositions are not formulated to have a total of 100 wt. % of the mixture of the indicated components.

Fatty Acid pH Dependent Carriers

The carriers of this invention may include:
(1) from about 0 wt. % to 100 wt. % of a biocompatible fatty acid or a mixture of biocompatible fatty acids, sometimes referred to herein as free fatty acids,
(2) from about 0 wt. % to 100 wt. % of a biocompatible fatty acid ester or a mixture of biocompatible fatty acid esters,
(3) from about 0 wt. % to 100 wt. % of a biocompatible fatty acid salt or a mixture of biocompatible fatty acid salts,
(4) from about 0 wt. % to 100 wt. % of a biocompatible oil or a mixture of biocompatible oil,
(5) from about 0 wt. % to 100 wt. % of a secondary complexing agent or a mixture of secondary complexing agents, where the secondary complexing agents depends on the nature of the active agent to be carried by the carrier,
(6) from about 0 wt. % to about 50 wt. % of a secondary anti-toxicity agent or a mixture of secondary anti-toxicity agents, where the secondary anti-toxicity agents depends on the nature of the active agent to be carried by the carrier, and (7) from about 0 wt. % to about 50 wt. % of (a) an excipient or a mixture of excipients, (b) an adjuvant or a mixture of adjuvants, (c) a drying or a mixture of drying agents, (d) a antioxidant or a mixture of antioxidants, (e) a preservative or a mixture of preservatives, (f) or a mixture of chelating agents, (g) a viscomodulator or a mixture of viscomodulators, (h) a tonicifier or a mixture of tonicifiers, (I) a flavorant or a mixture of flavorants, (j) a colorant or a mixture of colorants, (k) a odorant or a mixture of odorants, (1) a opacifier or a mixture of opacifiers, (m) a suspending agent or a mixture of suspending agents, and (n) mixtures thereof.

In other embodiments, the carriers include:
(1) from about 5 wt. % to 100 wt. % of a biocompatible fatty acid or a mixture of biocompatible fatty acids, sometimes referred to herein as free fatty acids,
(2) from about 5 wt. % to 100 wt. % of a biocompatible fatty acid ester or a mixture of biocompatible fatty acid esters,
(3) from about 5 wt. % to 100 wt. % of a biocompatible fatty acid salt or a mixture of biocompatible fatty acid salts,
(4) from about 0 wt. % to 100 wt. % of a biocompatible oil or a mixture of biocompatible oil,
(5) from about 0 wt. % to 100 wt. % of a secondary complexing agent or a mixture of secondary complexing agents, where the secondary complexing agents depends on the nature of the active agent to be carried by the carrier,
(6) from about 0 wt. % to about 25 wt. % of a secondary anti-toxicity agent or a mixture of secondary anti-toxicity agents, where the secondary anti-toxicity agents depends on the nature of the active agent to be carried by the carrier, and
(7) from about 0 wt. % to about 25 wt. % of (a) an excipient or a mixture of excipients, (b) an adjuvant or a mixture of adjuvants, (c) a drying or a mixture of drying agents, (d) a antioxidant or a mixture of antioxidants, (e) a preservative or a mixture of preservatives, (f) or a mixture of chelating agents, (g) a viscomodulator or a mixture of viscomodulators, (h) a tonicifier or a mixture of tonicifiers, (I) a flavorant or a mixture of flavorants, (j) a colorant or a mixture of colorants, (k) a odorant or a mixture of odorants, (1) a opacifier or a mixture of opacifiers, (m) a suspending agent or a mixture of suspending agents, and (n) mixtures thereof.

In other embodiments, the carriers include:
(1) from about 10 wt. % to 100 wt. % of a biocompatible fatty acid or a mixture of biocompatible fatty acids, sometimes referred to herein as free fatty acids,
(2) from about 10 wt. % to 100 wt. % of a biocompatible fatty acid ester or a mixture of biocompatible fatty acid esters,
(3) from about 10 wt. % to 100 wt. % of a biocompatible fatty acid salt or a mixture of biocompatible fatty acid salts,
(4) from about 0 wt. % to 100 wt. % of a biocompatible oil or a mixture of biocompatible oil,
(5) from about 0 wt. % to 100 wt. % of a secondary complexing agent or a mixture of secondary complexing agents, where the secondary complexing agents depends on the nature of the active agent to be carried by the carrier,
(6) from about 0 wt. % to about 25 wt. % of a secondary anti-toxicity agent or a mixture of secondary anti-toxicity agents, where the secondary anti-toxicity agents depends on the nature of the active agent to be carried by the carrier, and
(7) from about 0 wt. % to about 25 wt. % of (a) an excipient or a mixture of excipients, (b) an adjuvant or a mixture of adjuvants, (c) a drying or a mixture of drying agents, (d) a antioxidant or a mixture of antioxidants, (e) a preservative or a mixture of preservatives, (f) or a mixture of chelating agents, (g) a viscomodulator or a mixture of viscomodulators, (h) a tonicifier or a mixture of tonicifiers, (I) a flavorant or a mixture of flavorants, (j) a colorant or a mixture of colorants, (k) a odorant or a mixture of odorants, (l) a opacifier or a mixture of opacifiers, (m) a suspending agent or a mixture of suspending agents, and (n) mixtures thereof.

The above compositions are formulated to have a total of 100 wt. % of a mixtures of the indicated components.

Another way to present the carriers is in weight ratios of components. In certain embodiments, the ratio of ingredient classes is 1-3:4:5:6:7 is from 1:0:0:0:0 to 0:1:0:0:0 to 1:0:1:1:1 to 0:1:1:1:1. In other embodiments, the ratio of ingredient classes is 1-3:4:5:6:7 is from 10:1:0:0:0 to 1:10:0:0:0 to 10:1:1:1:1:1 to 1:10:1:1:1. In other embodiments, the ratio of ingredient classes is 1-3:4:5:6:7 is from 5:1:0:0:0 to 1:5:0:0:0 to 5:1:1:1:1:1 to 1:5:1:1:1. In other embodiments, the ratio of ingredient classes is 1-3:4:5:6:7 is from 4:1:0:0:0 to 1:4:0:0:0 to 4:1:1:1:1:1 to 1:4:1:1:1. In other embodiments, the ratio of ingredient classes is 1-3:4:5:6:7 is from 3:1:0:0:0 to 1:3:0:0:0 to 3:1:1:1:1:1 to 1:3:1:1:1. In other embodiments, the ratio of ingredient classes is 1-3:4:5:6:7 is from 2:1:0:0:0 to 1:2:0:0:0 to 2:1:1:1:1:1 to 1:2:1:1:1. In other embodiments, the ratio of ingredient classes is 1-3:4:5:6:7 is from 1:1:0:0:0 to 1:1:1:1:1:1. Of course, the actual value of each level may range through the entire range within the individual ranges.

The carrier and/or the carrier components are designed to modify and/or alter the chemical and/or physical properties and/or behavior of at least one active agent in tissues and/or organs reducing and/or altering tissue and/or organ toxicity, improving and/or altering bioavailability, and/or improving and/or altering efficacy. In certain embodiments, the carriers and/or the biocompatible, hydrophobic agents modify and/or alter the chemical and/or physical properties and/or behavior of at least one active agent in tissues and/or organs in a pH dependent manner to reduce and/or alter tissue and/or organ toxicity, improve and/or alter bioavailability, and/or improve and/or alter efficacy.

In certain embodiments, the carrier comprises between about 100 wt. % and 50 wt. % biocompatible oils and between about 0 wt. % and 50 wt. % biocompatible fatty acids. In other embodiments, between about 0 wt. % and 50 wt. % biocompatible oils and between about 100 wt. % and 50 wt. % biocompatible fatty acids.

Low Phospholipid Carriers

In certain embodiments, the carrier comprises between about 100 wt. % and 99 wt. % biocompatible oils and between about 0 wt. % and 1 wt. % phospholipids. In other embodiments, between about 100 wt. % and 98 wt. % biocompatible oils and between about 0 wt. % and 2 wt. % phospholipids. In other embodiments, between about 100 wt. % and 95 wt. % biocompatible oils and between about 0 wt. % and 5 wt. % phospholipids. In other embodiments, between about 100 wt. % and 90 wt. % biocompatible oils and between about 0 wt. % and 10 wt. % phospholipids.

In other embodiments, the carrier comprises between about 100 wt. % and 80 wt. % biocompatible oils, between about 0 wt. % and about and between about 10 wt. % biocompatible fatty acids, and between about 0 wt. % and 10 wt.

% phospholipids. In other embodiments, the carrier comprises between about 100 wt. % and 40 wt. % biocompatible oils, between about 0 wt. % and about and between about 40 wt. % biocompatible fatty acids, and between about 0 wt. % and 10 wt. % phospholipids.

In certain embodiments, the carrier comprises between about 100 wt. % and 80 wt. % biocompatible fatty acids, between about 0 wt. % and about and between about 10 wt. % biocompatible oils, and between about 0 wt. % and 10 wt. % phospholipids. In other embodiments, between about 100 wt. % and 40 wt. % biocompatible fatty acids, between about 0 wt. % and about and between about 40 wt. % biocompatible oils, and between about 0 wt. % and 10 wt. % phospholipids.

In certain embodiments, the carrier may also include between about 0.5 wt. % and about 2 wt. % sterols, between about 5 wt. % and about 10 wt. % glycolipids, and between about 0.5 wt. % and 2 wt. %, less than 2 wt. % water. The phospholipids comprise between about 75 wt. % and about 100 wt. % phosphatidylcholine, between about 0 wt. % and about 10 wt. % phophatidylethanolmine, between about lyso-phosphatidylcholine 0 wt. % and about 10 wt. %, and between about 0 wt. % and about 2 wt. % monophosphotidylinositol. The biocompatible oils comprises between about 50 wt. % and 80 wt. % triglycerides, between about 0 wt. % and 5 wt. % mono & diglycerides, between about 5 wt. % and about 20 wt. % free fatty acids.

High Phospholipid Carriers

In certain embodiments, the carrier comprises between about 30 wt. % and 50 wt. % phospholipids, between about 30 wt. % and 50 wt. % biocompatible oils, between about 0.5 wt. % and about 2 wt. % sterols, between about 5 wt. % and about 10 wt. % glycolipids, and between about 0.5 wt. % and 2 wt. %, less than 2 wt. % water. The phospholipids comprise between about 75 wt. % and about 100 wt. % phosphatidylcholine, between about 0 wt. % and about 10 wt. % phophatidylethanolmine, between about lyso-phosphatidylcholine 0 wt. % and about 10 wt. %, and between about 0 wt. % and about 2 wt. % monophosphotidylinositol. The biocompatible oils comprises between about 50 wt. % and 80 wt. % triglycerides, between about 0 wt. % and 5 wt. % mono & diglycerides, between about 5 wt. % and about 20 wt. % free fatty acids.

In certain embodiments, the carrier comprises between about 30 wt. % and 50 wt. % phospholipids, between about 30 wt. % and 50 wt. % biocompatible oils, between about 0.5 wt. % and about 2 wt. % sterols, between about 5 wt. % and about 10 wt. % glycolipids, and between about 0.5 wt. % and 2 wt. %, less than 2 wt. % water. The phospholipids comprise between about 75 wt. % and about 100 wt. % phosphatidylcholine, between about 0.1 wt. % and about 10 wt. % phophatidylethanolmine, between about lyso-phosphatidylcholine 0.1 wt. % and about 10 wt. %, and between about 0.5 wt. % and about 2 wt. % monophosphotidylinositol. The biocompatible oils comprises between about 50 wt. % and 80 wt. % triglycerides, between about 0.5 wt. % and 5 wt. % mono & diglycerides, between about 5 wt. % and about 20 wt. % free fatty acids.

Free Fatty Acid, Biocompatible Oil, and Phospholipid Compositions

In certain embodiments, the carriers comprise free fatty acids (FFAs), biocompatible oils (BCGs), and phospholipids (PLs) in a weight ratio of a:b:c (FFAs:BCOs:PLs), where a ranges from 1 to 10, b ranges from 0 to 10, and c ranges from 0 to 10. In certain embodiments, a ranges from 0 to 10, b ranges from 1 to 10, and c ranges from 0 to 10. In certain embodiments, a ranges from 1 to 10, b ranges from 1 to 10, and c ranges from 0 to 10. The FFAs in the carriers may be a single free fatty acid or a mixture of free fatty acids as defined herein. The BCOs in the carriers may be a single biocompatible oil or a mixture of biocompatible oils. The PLs in the carriers may be a single phospholipid or a mixture of phospholipids.

In certain embodiments, the carriers comprise free fatty acids (FFAs), neutral lipids (NLs), and phospholipids (PLs) in weight ratios a:b:c (FFAs:NLs:PLs), where a ranges from 1 to 10, b ranges from 0 to 10, and c ranges from 0 to 10. In certain embodiments, a ranges from 0 to 10, b ranges from 1 to 10, and c ranges from 0 to 10. In certain embodiments, a ranges from 1 to 10, b ranges from 1 to 10, and c ranges from 0 to 10. The FFAs in the carriers may be a single free fatty acid or a mixture of free fatty acids as defined herein. The NLs in the carriers may be a single neutral lipid or a mixture of neutral lipids, where the neutral lipids comprise mono-, di- and/or tri-glycerides. The Pls in the carriers may be a single phospholipid or a mixture of phospholipids.

Secondary Complexing Agent and/or Anti-Toxicity Agents NSAIDs

In certain NSAID compositions, the secondary anti-toxicity agents include less than or equal to about 10 wt. % of at least one zwitterionic agent such as a zwitterionic surfactant. In other NSAID compositions, the secondary anti-toxicity agents include less than or equal to about 7.5 wt. % of at least one zwitterionic agent such as a zwitterionic surfactant. In other NSAID compositions, the secondary anti-toxicity agents include less than or equal to about 5 wt. % of at least one zwitterionic agent such as zwitterionic surfactants. In other NSAID compositions, the secondary anti-toxicity agents include less than or equal to about 2.5 wt. % of at least one zwitterionic agent such as zwitterionic surfactants. In other NSAID compositions, the secondary anti-toxicity agents include from about 0.1 wt. % to about 10 wt. % of at least one zwitterionic agent such as zwitterionic surfactants. In other NSAID compositions, the secondary anti-toxicity agents include from about 0.5 wt. % to about 10 wt. % of at least one zwitterionic agent such as zwitterionic surfactants. In other NSAID compositions, the secondary anti-toxicity agents include from about 1 wt. % to about 10 wt. % of at least one zwitterionic agent such as zwitterionic surfactants. In other NSAID compositions, the secondary anti-toxicity agents include from about 2 wt. % to about 10 wt. % of at least one zwitterionic agent such as zwitterionic surfactants.

In certain NSAID compositions, the secondary anti-toxicity agents include from about 0 wt. % to about 50 wt. % of at least one triglyceride neutral lipid. In other NSAID compositions, the secondary anti-toxicity agents include from about 0.1 wt. % to about 10 wt. % of at least one proton pump inhibitor (PPI).

In certain NSAID compositions, the secondary anti-toxicity agents include less than or equal to about 10 wt. % of at least one zwitterionic agent and from about 0 wt. % to about 50 wt. % of at least one neutral lipid. In other NSAID compositions, the secondary anti-toxicity agents include less than or equal to about 10 wt. % of at least one zwitterionic agent and from about 1 wt. % to about 50 wt. % of at least one neutral lipid.

In certain NSAID compositions, the secondary anti-toxicity agents include less than or equal to about 10 wt. % of at least one zwitterionic agent and from about 0 wt. % to about 10 wt. % of at least one PPI. In other NSAID compositions, the secondary anti-toxicity agents include less than or equal to about 10 wt. % of at least one zwitterionic agent and from about 0.5 wt. % to about 10 wt. % of at least one PPI. In other NSAID compositions, the secondary anti-toxicity agents include less than or equal to about 10 wt. % of at least one zwitterionic agent, from about 0.5 wt. % to about 50 wt. % of at least one neutral lipid, and from about 0.5 wt. % to about 10 wt. % of at least one PPI.

Compositions

The compositions of this invention may generally be formulated with at least one biologically active agent as a major component.

The compositions of this invention may have weight ratios of active agents to carrier, where the carrier is present in an amount of form at least a monolayer coating on the active agents. In certain embodiment, the weight ratios of active agents to carrier is from about 100:1 to about 1:100. In other embodiment, the ratio is between about 100:1 and about 1:10. In other embodiment, the ratio is between about 50:1 and about 1:5. In other embodiment, the ratio is between about 25:1 and about 1:5. In other embodiment, the ratio is between about 10:1 and about 1:1. In other embodiments, the ratio is between about 5:1 and about 1:1. In other embodiments, the ratio is from about 5:1 to about 1:1. The term about means±5%.

Pharmaceutical or Nutraceutical Dosages

In pharmaceutical compositions, the compositions will generally contain from about 1 mg to about 5000 mg per dose depending on the pharmaceutical agent(s). In other pharmaceutical compositions, the compositions will contain from about 10 mg to about 2500 mg per dose depending on the pharmaceutical agent(s). In other pharmaceutical compositions, the compositions will contain from about 250 mg to about 2500 mg per dose depending on the pharmaceutical agent(s). In other pharmaceutical compositions, the compositions will contain from about 500 mg to about 2500 mg per dose depending on the pharmaceutical agent(s). In other pharmaceutical compositions, the compositions will contain from about 500 mg to about 2000 mg per dose depending on the pharmaceutical agent(s). In other pharmaceutical compositions, the compositions will contain from about 1 mg to about 2000 mg per dose depending on the pharmaceutical agent(s). In other pharmaceutical compositions, the compositions will contain from about 1 mg to about 1000 mg per dose depending on the pharmaceutical agent(s). Of course, the exact dosage for each compositions will depend on the pharmaceutical agent(s) used and the potency of the pharmaceutical agent(s).

In nutraceutical compositions, the compositions will generally contain from about 1 mg to about 5000 mg per dose depending on the nutraceutical agent(s). In other nutraceutical compositions, the compositions will contain from about 10 mg to about 2500 mg per dose depending on the nutraceutical agent(s). In other nutraceutical compositions, the compositions will contain from about 250 mg to about 2500 mg per dose depending on the nutraceutical agent(s). In other nutraceutical compositions, the compositions will contain from about 500 mg to about 2500 mg per dose depending on the nutraceutical agent(s). In other nutraceutical compositions, the compositions will contain from about 500 mg to about 2000 mg per dose depending on the nutraceutical agent(s). In other nutraceutical compositions, the compositions will contain from about 1 mg to about 2000 mg per dose depending on the nutraceutical agent(s). In other nutraceutical compositions, the compositions will contain from about 1 mg to about 1000 mg per dose depending on the nutraceutical agent(s). Of course, the exact dosage for each compositions will depend on the pharmaceutical agent(s) used and the potency of the pharmaceutical agent(s).

Reagents Suitable for Use in the Invention pH Dependent Release Agents

Fatty Acids

Suitable biocompatible fatty acids for use in this invention include, without limitation, any saturated fatty acid or unsaturated fatty acids or mixtures or combinations thereof suitable for a human, mammal or animal consumption. Exemplary fatty acids include short chain free fatty acids (SCFFA), medium chain free fatty acids (MCFFA), long chain free fatty acids (LCFFA), very-long-chain free fatty acids (VLCFFA) and mixtures or combinations thereof. SCFFA include free fatty acids having a carbyl tail group having less than between 4 and less than 8 carbon atoms ($C_4$ to $C_8$). MCFFA include free fatty acids having a carbyl group having between 8 and less than 14 carbon atoms ($C_8$ to $C_{14}$). LCFFA include free fatty acids having a carbyl group having between 14 and 24 carbon atoms ($C_{14}$-$C_{24}$). VLCFFA include free fatty acids having a carbyl group having greater than 24 carbon atoms ($>C_{24}$). Exemplary unsaturated fatty acids include, without limitation, myristoleic acid [$CH_3(CH_2)_3CH=CH(CH_2)_7COOH$, cis-$\Delta^9$, C:D 14:1, n-5], palmitoleic acid [$CH_3(CH_2)_5CH=CH(CH_2)_7COOH$, cis-$\Delta^9$, C:D 16:1, n-7], sapienic acid [$CH_3(CH_2)_8CH=CH(CH_2)_4COOH$, cis-$\Delta^6$, C:D 16:1, n-10], oleic acid [$CH_3(CH_2)_7CH=CH(CH_2)_7COOH$, cis-$\Delta^9$, C:D 18:1, n-9], linoleic acid [$CH_3(CH_2)_4CH=CHCH_2CH=CH(CH_2)_7COOH$, cis,cis-$\Delta^9,\Delta^{12}$, C:D 18:2, n-6], α-Linolenic acid [$CH_3CH_2CH=CHCH_2CH=CHCH_2CH=CH(CH_2)_7COOH$, cis,cis,cis-$\Delta^9,\Delta^{12},\Delta^{15}$, C:D 18:3, n-3], arachidonic acid [$CH_3(CH_2)_4CH=CHCH_2CH=CHCH_2CH=CHCH_2CH=CH(CH_2)_3COOH$, cis,cis,cis,cis-$\Delta^5\Delta^8,\Delta^{11},\Delta^{14}$, C:D 20:4, n-6], eicosapentaenoic acid [$CH_3CH_2CH=CHCH_2CH=CHCH_2CH=CHCH_2CH=CHCH_2CH=CH(CH_2)_3COOH$], cis,cis,cis,cis,cis-$\Delta^5,\Delta^8,\Delta^{11},\Delta^{14},\Delta^{17}$, 20:5, n-3], erucic acid [$CH_3(CH_2)_7CH=CH(CH_2)_{11}COOH$, cis-$\Delta^{13}$, C:D 22:1, n-9], docosahexaenoic acid [$CH_3CH_2CH=CHCH_2CH=CHCH_2CH=CHCH_2CH=CH CH_2CH=CHCH_2CH=CH(CH_2)_2COOH$, cis,cis,cis,cis,cis,cis-$\Delta^4,\Delta^7,\Delta^{10},\Delta^{13},\Delta^{16},\Delta^{19}$, C:D 22:6, n-3], or mixtures and combinations thereof.

Exemplary saturated fatty acids include, without limitation, lauric acid [$CH_3(CH_2)_{10}COOH$, C:D 12:0], myristic acid [$CH_3(CH_2)_{12}COOH$, C:D 14:0], palmitic acid [$CH_3(CH_2)_{14}COOH$, C:D 16:0], stearic acid [$CH_3(CH_2)_{16}COOH$, C:D 18:0], arachidic acid [$CH_3(CH_2)_{18}COOH$, C:D 20:0], behenic acid [$CH_3(CH_2)_{20}COOH$, C:D 22:0], lignoceric acid [$H_3(CH_2)_{22}COOH$, C:D 24:0], cerotic acid [$CH_3(CH_2)_{24}COOH$, C:D 26:0], or mixture or combinations thereof.

Exemplary saturated fatty acids include, without limitation, butyric ($C_4$), valeric ($C_5$), caproic ($C_6$), enanthic ($C_7$), caprylic ($C_8$), pelargonic ($C_9$), capric ($C_{10}$), undecylic ($C_{11}$), lauric ($C_{12}$), tridecylic ($C_{13}$), myristic ($C_{14}$), pentadecylic ($C_{15}$), palmitic ($C_{16}$), margaric ($C_{17}$), stearic ($C_{18}$), nonadecylic ($C_{19}$), arachidic ($C_{20}$), heneicosylic ($C_{21}$), behenic ($C_{22}$), tricosylic ($C_{23}$), lignoceric ($C_{24}$), pentacosylic ($C_{25}$), cerotic ($C_{26}$), heptacosylic ($C_{27}$), montanic ($C_{28}$), nonacosylic ($C_{29}$), melissic ($C_{30}$), hentriacontylic ($C_{31}$), lacceroic ($C_{32}$), psyllic ($C_{33}$), geddic ($C_{34}$), ceroplastic ($C_{35}$), hexatriacontylic ($C_{36}$) and mixtures or combinations thereof. Unsaturated fatty acids include, without limitation, n-3 unsaturated fatty acids such as α-linolenic acid, stearidonic acid, eicosapentaenoic acid, and docosahexaenoic acid, n-6 unsaturated fatty acids such as linoleic acid, γ-linolenic acid, dihomo-γ-linolenic acid, and arachidonic acid, n-9 unsaturated fatty acids oleic acid, elaidic acid, eicosenoic acid, erucic acid, nervonic acid, mead acid and mixtures or combinations thereof.

Poly Acids

Suitable poly carboxylic acid compounds for use a pH depending release agents include, without limitation, any poly carboxylic acid compound. Exemplary examples of water immiscible poly acids include, without limitation, dicarboxylic acids having carbyl or carbenzyl groups having between 8 and 50 carbon atoms and mixtures or combinations thereof. Polymer carboxylic acids or polymers including carboxylic acid groups, where the polymers are oil soluble or are oils, not miscible with water. Exemplary example of hydrophilic poly acids include, without limitation, polyacrylic acid, polymethacrylic acid, polylactic acid, polyglycol acid, mixtures and combinations thereof, copolymers thereof, CARBOPOL® reagents available from Lubrizol Corporation (a registered trademark of the Lubrizol Corporation), other carboxylic acid containing polymers, or mixtures or combinations thereof.

Fatty Acid Esters

Fatty acid esters comprise esters of any of the fatty acids listed above including, without limitation, mono-alcohol esters, where the mono-alcohol or polyols including 1 carbon atom to 20 carbon atoms, where one or more of the carbon atoms may be replace by O, NR(R is a carbyl group having between 1 and 5 carbon atoms), or S. Exemplary mono-alcohols used to from the free fatty acid esters include methanol, ethanol, propanol, butanol, pentanol or mixtures thereof.

Fatty Acid Salts

Suitable biocompatible fatty acid salts for use in this invention include, without limitation, alkali metal salts of any of the above listed fatty acids, alkaline earth metals salts of any of the above listed fatty acids, transition metal salts of any of the above listed fatty acids or mixture or combinations thereof. In certain embodiments, the metal salts include lithium, sodium, potassium, cesium, magnesium, calcium, barium, copper, zinc, cobalt, iron, or mixture or combinations thereof.

Secondary Complexing Agents and/or Anti-Toxicity Agents

Suitable secondary complexing agents and/or secondary anti-toxicity agents for use in the compositions of this invention include, without limitation, phospholipids, amphoteric agents and/or zwitterionic agents or mixtures or combinations thereof. Phospholipids include any phospholipid or mixtures and combinations thereof such as (1) diacylglyceride phospholipids or glycerophospholipids include, without limitation, phosphatidic acid (phosphatidate) (PA), phosphatidylethanolamine (cephalin) (PE), phosphatidylcholine (lecithin) (PC), phosphatidylserine (PS), phosphoinositides such as phosphatidylinositol (PI), phosphatidylinositol phosphate (PIP), phosphatidylinositol bisphosphate (PIP2) and phosphatidylinositol triphosphate (PIP3), and (2) phosphosphingolipids such as ceramide phosphorylcholine (Sphingomyelin) (SPH), ceramide phosphorylethanolamine (Sphingomyelin) (Cer-PE), and ceramide phosphorylglycerol. Amphoteric agents include acetates, betaines, glycinates, imidazolines, propionates, other amphoteric agents or mixtures thereof. Zwitterionic agents include, without limitation, biocompatible, zwitterionic phospholipids, biocompatible, zwitterionic betaines, biocompatible, biocompatible amphoteric/zwitterionic surfactants, biocompatible quaternary salts, biocompatible amino acids, other biocompatible compounds capable of forming or in the form of a zwitterion, or mixtures or combinations thereof.

Suitable biocompatible, zwitterionic phospholipids for use in this invention include, without limitation, a phospholipid of general formula:

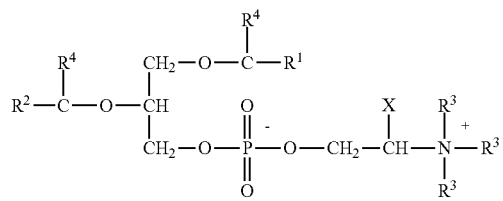

where $R^1$ and $R^2$ are saturated or unsaturated substitutions ranging from 8 to 32 carbon atoms; $R^3$ is H or $CH_3$, and X is H or COOH; and $R^4$ is =O or $H_2$. Mixtures and combinations of the zwitterionic phospholipids of the general formula and mixtures and combinations of NSAIDs can be used as well.

Exemplary examples of zwitterionic phospholipid of the above formula include, without limitation, phosphatidylcholines such as phosphatidyl choline (PC), dipalmitoylphosphatidylcholine (DPPC), other disaturated phosphatidylcholines, phosphatidylethanolamines, phosphatidylinositol, phosphatidylserines sphingomyelin or other ceramides, or various other zwitterionic phospholipids, phospholipid containing oils such as lecithin oils derived from soy beans, dimyristoylphosphatidylcholine, distearoylphosphatidylcholine, dilinoleoylphosphatidylcholine (DLL-PC), dipalmitoylphosphatidylcholine (DPPC), soy phophatidylchloine (Soy-PC or $PC_S$) and egg phosphatidycholine (Egg-PC or $PC_E$). In DPPC, a saturated phospholipid, the saturated aliphatic substitution $R_1$ and $R_2$ are $CH_3-(CH_2)_{14}$, $R_3$ is $CH_3$ and X is H. In DLL-PC, an unsaturated phospholipid, $R_1$ and $R_2$ are $CH_3-(CH_2)_4-CH=CH-CH_2-CH=CH-(CH_2)_7$, $R_3$ is $CH_3$ and X is H. In Egg PC, which is a mixture of unsaturated phospholipids, $R_1$ primarily contains a saturated aliphatic substitution (e.g., palmitic or stearic acid), and $R_2$ is primarily an unsaturated aliphatic substitution (e.g., oleic or arachidonic acid). In Soy-PC, which in addition to the saturated phospholipids (palmitic acid and stearic acid) is a mixture of unsaturated phospholipids (oleic acid, linoleic acid and linolenic acid). In certain embodiments, the phospholipids are zwitterionic phospholipid include, without limitation, dipalmitoyl phosphatidylcholine, phosphatidyl choline, or a mixture thereof.

Exemplary acetates include, without limitation, lauroarnphoacetate, alkyl amphoacetate, cocoampho(di)acetate, cocoarnphoacetate, cocoamphodiacetate, disodium cocoamphodiacetate, sodium cocoamphoacetate, sodium lauroamphoacetate, disodium cocoamphodiacetate, disodium capryloamphodiacetate, disodium lauroamphoacetate, disodium wheatgermamphodiacetate, cocoarnphoacetate, cocoamphoace tate, cocoamphoacetate, cocoamphoacetate and cocoamphodiacetate, disodium cocoamphodiacetate, and mixtures or combinations thereof.

Exemplary betaines include, without limitation, cocamidopropyl betaine, sodium lauroamphoace, cocoamidopropyl hydroxy sulfo baden (CHSB), dodecyl dimethyl betaine, cetyl betaine, lauroarnphoacetate, alkyl amphoacetate, cocoampho(di)acetate, cocoarnphoacetate, cocoamphodiacetate, disodium cocoamphodiacetate, sodium cocoamphoacetate, sodium lauroamphoacetate, disodium cocoamphodiacetate, disodium capryloamphodiacetate, disodium lauroamphoacetate, disodium wheatgermamphodiacetate, cocoarnphoacetate, alkylamido baden; alkyldimethyl betaine, cocoamidopropylbetaine, tallow bis(hydroxyethyl)baden, hexadecyldimethylbetaine, alkyl amido propyl sulfo baden, alkyl dimethyl amine baden, coco amido propyl dimethyl baden, alkyl amido propyl dimethyl amine baden, cocamidopropyl baden, lauryl betaine, laurylamidopropyl betaine, coco amido baden, lauryl amido baden, dimethicone propyl PG-betaine, N-alkyldimethyl betaine, coco biguanide derivative, cetyl baden, oleamidopropyl betaine, isostearamidopropyl betaine, oleyl betaine, wheatgermamidopropyl betaine, cocamidopropyl betaine, lauramidopropyl betaine, 2-alkyl-N-carboxymethyl-N-hydroxyethyl imidazolinium baden; cocamidopropyl betaine, isostearamidopropyl betaine, myristamidopropyl betaine, palmitamidopropyl betaine, cocamidopropyl hydroxy sultaine, ammonium chloride cocamidopropyl hydroxy sultaine and potassium chloride, cocamidopropyl hydroxy sultaine, undecylenamidopropyl baden, wheatgermamidopropyl betaine, or mixture and combinations thereof.

Exemplary glycinates including, without limitation, Ampholak 7CX, Ampholak X07, cocoamphocarboxyglycinate, tallowamphocarboxyglycinate, oleoamphocarboxyglycinate, cocoiminodiglycinate, capryloamphocarboxyglycinate, bis-2-hydroxyethyl tallow glycinate, lauryl amphoglycinate, oleic polyamphoglycinate, —$C_{10/12}$-fatty acid amidoethyl-N-(2-hydroxyethyl)-glycinate, —$C_{12/18}$-fatty acid amidoethyl-N-(2-hydroxyethyl)-glycinate, dihydroxyethyl tallow glycinate, and mixtures or combinations thereof.

Exemplary imidazo lines including, without limitation, 2-alkyl-1-(ethyl-beta-oxipropanoianoic)imidazoline sodium salt based on caprylic acid, 1-hydrox yethyl-2-alkylimidazoline, coco imidazoline, tall oil imidazoline, lauryl imidazoline, coco imidazoline dicarboxymethylated, sodium copra dicarboxylic imidazoline, oleyl imidazoline and mixtures or combinations thereof.

Exemplary propionates including, without limitation, cocoiminodipropionate, octyliminodipropionate, cocoalkylaminopropionic acid, cocoamphodipropionate, lauraminopropionic acid, disodium tallow-P-iminodipropionate, monosodium-N-lauryl P-iminodipropionic acid, disodium lauriminodipropionate, sodium lauriminopropionic acid, 2-ethylhexylamino dipropionate, coco amino dipropionate, cocaminopropionic acid, lauraminopropionic acid, sodium lauriminodipropionate, disodium cocoamphodipropionate, disodium capryloamphodipropionate, disodium lauroamphodipropionate, sodium cocoamphopropionate, sodium lauriminodipropionate, sodium alkyliminopropionate and mixtures or combinations thereof.

Exemplary other amphoteric agents including, without limitation, N-coco-3-aminobutyric acid, sodium salt, N-coco-3-aminobutyric acid, ethoxylated fatty alcohol carboxym, cocamidopropyl hydroxy sultaine, sodium cocoamphohydroxypropyl sulfonate, sodium capryloarnphohydroxypropyl sulfonate and mixtures or combinations thereof.

Pharmaceutical Agents

Suitable pharmaceutical agents for use in the compositions of this invention include, without limitation, any pharmaceutical agent capable of being dispersed in a carrier of this invention. In certain embodiments, the pharmaceutical agents are solids. In other embodiments, the pharmaceutical agents are liquids. In other embodiments, the pharmaceutical agents are weak acid pharmaceutical agents. In other embodiments, the pharmaceutical agents are weak base pharmaceutical agents.

Hydrophobic Pharmaceutical and/or Nutraceutical Agents

Hydrophobic therapeutic agents suitable for use in the pharmaceutical compositions of the present invention are not particularly limited, as the carrier is surprisingly capable of solubilizing and delivering a wide variety of hydrophobic therapeutic agents. Hydrophobic therapeutic agents are compounds with little or no water solubility. Intrinsic water solubilities (i.e., water solubility of the unionized form) for hydrophobic therapeutic agents usable in the present invention are less than about 1% by weight, and typically less than about 0.1% or 0.01% by weight. Such therapeutic agents can be any agents having therapeutic or other value when administered to an animal, particularly to a mammal, such as drugs, nutrients, and cosmetics (cosmeceuticals). It should be understood that while the invention is described with particular reference to its value in the form of aqueous dispersions, the invention is not so limited. Thus, hydrophobic drugs, nutrients or cosmetics which derive their therapeutic or other value from, for example, topical or transdermal administration, are still considered to be suitable for use in the present invention.

Specific non-limiting examples of hydrophobic therapeutic agents that can be used in the pharmaceutical compositions of the present invention include the following representative compounds, as well as their pharmaceutically acceptable salts, isomers, esters, ethers and other derivatives: analgesics and anti-inflammatory agents, such as aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenamic acid, mefenamic acid, nabumetone, naproxen, oxaprozin, oxyphenbutazone, phenylbutazone, piroxicam, refocoxib, sulindac, tetrahydrocannabinol, tramadol and tromethamine; antihelminthics, such as alb endaz ole, bephenium hydroxynaphthoate, cambendazole, dichlorophen, ivermectin, mebendazole, oxamniquine, oxfendazole, oxantel embonate, praziquantel, pyrantel embonate and thiabendazole; anti-arrhythmic agents, such as amiodarone HCl, disopyramide, flecamide acetate and quinidine sulfate; anti-asthma agents, such as zileuton, zafirlukast, terbutaline sulfate, montelukast, and albuterol; anti-bacterial agents such as alatrofloxacin, azithromycin, baclofen, benzathine penicillin, cinoxacin, ciprofloxacin HCl, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin HCl, nalidixic acid, nitrofurantoin, norfloxacin, ofloxacin, rifampicin, rifabutine, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim, trovafloxacin, and vancomycin; anti-viral agents, such as abacavir, amprenavir, delavirdine, efavirenz, indinavir, lamivudine, nelfinavir, nevirapine, ritonavir, saquinavir, and stavudine; anti-coagulants, such as cilostazol, clopidogrel, dicumarol, dipyridamole, nicoumalone, oprelvekin, phenindione, ticlopidine, and tirofiban; anti-depressants, such as amoxapine, bupropion, citalopram, clomipramine, fluoxetine HCl, maprotiline HCl, mianserin HCl, nortriptyline HCl, paroxetine HCl, sertraline HCl, trazodone HCl, trimipramine maleate, and venlafaxine HCl; anti-diabetics, such as acetohexamide, chlorpropamide, glibenclamide, gliclazide, glipizide, glimepiride, miglitol, pioglitazone, repaglinide, rosiglitazone, tolazamide, tolbutamide and troglitazone; anti-epileptics, such as beclamide, carbamazepine, clonazepam, ethotoin, felbamate, fosphenyloin sodium, lamotrigine, methoin, methsuximide, methylphenobarbitone, oxcarbazepine, paramethadione, phenacemide, phenobarbitone, phenyloin, phensuximide, primidone, sulthiame, tiagabine HCl, topiramate, valproic acid, and vigabatrin; anti-fungal agents, such as amphotericin, butenafine HCl, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine HCl, terconazole, tioconazole and undecenoic acid; anti-gout agents, such as allopurinol, probenecid and sulphin-pyrazone; anti-hypertensive agents, such as amlodipine, benidipine, benezepril, candesartan, captopril, darodipine, diltazem HCl, diazoxide, doxazosin HCl, elanapril, eposartan, losartan mesylate, felodipine, fenoldopam, fosenopril, guanabenz acetate, irbesartan, isradipine, lisinopril, minoxidil, nicardipine HCl, nifedipine, nimodipine, nisoldipine, phenoxybenzamine HCl, prazosin HCl, quinapril, reserpine, terazosin HCl, telmisartan, and valsartan; anti-malarials, such as amodiaquine, chloroquine, chlorproguanil HCl, halofantrine HCl, mefloquine HCl, proguanil HCl, pyrimethamine and quinine sulfate; anti-migraine agents, such as dihydroergotamine mesylate, ergotamine tartrate, frovatriptan, methysergide maleate, naratriptan HCl, pizotyline malate, rizatriptan benzoate, sumatriptan succinate, and zolmitriptan; anti-muscarinic agents, such as atropine, benzhexyl HCl, biperiden, ethopropazine HCl, hyoscyamine, mepenzolate bromide, oxyphencyclimine HCl and tropicamide; anti-neoplastic agents and immunosuppressants, such as aminoglutethimide, amsacrine, azathioprine, bicalutamide, bisantrene, busulfan, camptothecin, cytarabine, chlorambucil, cyclosporin, dacarbazine, ellipticine, estramustine, etoposide, irinotecan, lomustine, melphalan, mercaptopurine, methotrexate, mitomycin, mitotane, mitoxantrone, mofetil mycophenolate, nilutamide, paclitaxel, procarbazine HCl, sirolimus, tacrolimus, tamoxifen citrate, teniposide, testolactone, topotecan HCl, and toremifene citrate; anti-protozoal agents, such as atovaquone, benznidazole, clioquinol, decoquinate, diiodohydroxyquinoline, diloxanide furoate, dinitolmide, furazolidone, metronidazole, nimorazole, nitrofurazone, ornidazole and tinidazole; anti-thyroid agents, such as carbimazole, paracalcitol, and propylthiouracil; anti-tussives, such as benzonatate; anxiolytics, sedatives, hypnotics and neuroleptics, such as alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, diazepam, droperidol, ethinamate, flunanisone, flunitrazepam, triflupromazine, fluphenthixol decanoate, fluphenazine decanoate, flurazepam, gabapentin, haloperidol, lorazepam, lormetazepam, medazepam, meprobamate, mesoridazine, methaqualone, methylphenidate, midazolam, molindone, nitrazepam, olanzapine, oxazepam, pentobarbitone, perphenazine pimozide, prochlorperazine, pseudoephedrine, quetiapine, rispiridone, sertindole, sulpiride, temazepam, thioridazine, triazolam, zolpidem, and zopiclone; .beta.-Blockers, such as acebutolol, alprenolol, atenolol, labetalol, metoprolol, nadolol, oxprenolol, pindolol and propranolol; cardiac inotropic agents, such as aminone, digitoxin, digoxin, enoximone, lanatoside C and medigoxin; corticosteroids, such as beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone and triamcinolone; diuretics, such as acetazolamide, amiloride, bendroflumethiazide, bumetanide, chlorothiazide, chlorthalidone, ethacrynic acid, frusemide, metolazone, spironolactone and triamterene. anti-parkinsonian agents, such as bromocriptine mesylate, lysuride maleate, pramipexole, ropinirole HCl, and tolcapone; gastrointestinal agents, such as bisacodyl, cimetidine, cisapride, diphenoxylate HCl, domperidone, famotidine, lansoprazole, loperamide, mesalazine, nizatidine, omeprazole, ondansetron HCl, rabeprazole sodium, ranitidine HCl and sulphasalazine; histamine H, and H,-receptor antagonists, such as acrivastine, astemizole, chlorpheniramine, cinnarizine, cetrizine, clemastine fumarate, cyclizine, cyproheptadine HCl, dexchlorpheniramine, dimenhydrinate, fexofenadine, flunarizine HCl, loratadine, meclizine HCl, oxatomide, and terfenadine; keratolytics, such as such as acetretin, calcipotriene, calcifediol, calcitriol, cholecalciferol, ergocalciferol, etretinate, retinoids, targretin, and tazarotene; lipid regulating agents, such as atorvastatin, bezafibrate, cerivastatin, ciprofibrate, clofibrate, fenofibrate, fluvastatin, gemfibrozil, pravastatin, probucol, and simvastatin; muscle relaxants, such as dantrolene sodium and tizanidine HCl; nitrates and other anti-anginal agents, such as amyl nitrate, glyceryl trinitrate, isosorbide dinitrate, isosorbide mononitrate and pentaerythritol tetranitrate; nutritional agents, such as calcitriol, carotenes, dihydrotachysterol, essential fatty acids, non-essential fatty acids, phytonadiol, vitamin A, vitamin B2, vitamin D, vitamin E and vitamin K. opioid analgesics, such as codeine, codeine, dextropropoxyphene, diamorphine, dihydrocodeine, fentanyl, meptazinol, methadone, morphine, nalbuphine and pentazocine; sex hormones, such as clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, norethisterone, norgestrel, oestradiol, conjugated estrogens, progesterone, rimexolone, stanozolol, stilbestrol, testosterone and tibolone; stimulants, such as amphetamine, dexamphetamine, dexfenfluramine, fenfluramine and mazindol; and others, such as becaplermin, donepezil HCl, L-thryroxine, methoxsalen, verteporfrin, physostigmine, pyridostigmine, raloxifene HCl, sibutramine HCl, sildenafil citrate, tacrine, tamsulosin HCl, and tolterodine.

Preferred hydrophobic therapeutic agents include sildenafil citrate, amlodipine, tramadol, celecoxib, rofecoxib, oxaprozin, nabumetone, ibuprofen, terbenafine, itraconazole, zileuton, zafirlukast, cisapride, fenofibrate, tizanidine, nizatidine, fexofenadine, loratadine, famotidine, paricalcitol, atovaquone, nabumetone, tetrahydrocannabinol, megestrol acetate, repaglinide, progesterone, rimexolone, cyclosporin, tacrolimus, sirolimus, teniposide, paclitaxel, pseudoephedrine, troglitazone, rosiglitazone, finasteride, vitamin A, vitamin D, vitamin E, and pharmaceutically acceptable salts, isomers and derivatives thereof. Particularly preferred hydrophobic therapeutic agents are progesterone and cyclosporin.

Suitable proton pump inhibitors for use in the present invention include, without limitation, omeprazole, lansoprazole, rabeprazole, pantoprazole, esomeprazole, and mixtures thereof.

It should be appreciated that this listing of hydrophobic therapeutic agents and their therapeutic classes is merely illustrative. Indeed, a particular feature, and surprising advantage, of the compositions of the present invention is the ability of the present compositions to solubilize and deliver a broad range of hydrophobic therapeutic agents, regardless of functional class. Of course, mixtures of hydrophobic therapeutic agents may also be used where desired. These carrier attributes will also be equally effective as a delivery vehicle for yet to be developed hydrophobic therapeutic agents.

In certain embodiments, the suitable pharmaceutical agents for use in the compositions of this invention include, without limitation, weak acid pharmaceuticals, weak acid pharmaceuticals or mixtures and combinations thereof. Exemplary weak acid pharmaceuticals include, without limitation, anti-inflammatory pharmaceuticals, steroids, sterols, NSAID, COX-2 inhibitors, or mixture thereof. Exemplary weak base pharmaceuticals include, without limitation, weak base antibiotics, caffeine, codiene, ephedrine, chlordiazepoxide, morphine, pilocarpine, quinine, tolbutamine, other weak base pharmaceutical agents and mixtures or combinations thereof. Exemplary anti-inflammatory pharmaceuticals include steroidal anti-inflammatory drugs, non-steroidal anti-inflammatory drugs, acetaminophen and COX-2 inhibitors or mixtures and combinations thereof.

Suitable NSAIDS include, without limitation: (a) propionic acid drugs including fenoprofen calcium, flurbiprofen, suprofen, benoxaprofen, ibuprofen, ketoprofen, naproxen, and/or oxaprozin; (b) acetic acid drug including diclofenac sodium, diclofenac potassium, aceclofenac, etodolac, indomethacin, ketorolac tromethamine, and/or ketorolac; (c) ketone drugs including nabumetone, sulindac, and/or tolmetin sodium; (d) fenamate drugs including meclofenamate sodium, and/or mefenamic acid; (e) oxicam drugs piroxicam, lornoxicam and meloxicam; (f) salicylic acid drugs including diflunisal, aspirin, magnesium salicylate, bismuth subsalicylate, and/or other salicylate pharmaceutical agents; (g) pyrazolin acid drugs including oxyphenbutazone, and/or phenylbutazone; and (h) mixtures or combinations thereof.

Suitable COX-2 inhibitors include, without limitation, celecoxib, rofecoxib, or mixtures and combinations thereof.

Acid Labile Pharmaceuticals

Suitable acid labile pharmaceutical active agents include, without limitation, peptides, proteins, nucleosides, nucleotides, DNA, RNA, glycosaminoglyacan, any other acid labile pharmaceuticals, or mixtures or combinations thereof. Examples of acid-labile drugs which may used in the carrier systems disclosed herein are e.g. (+)—N{3-[3-(4-fluorophenoxy)phenyl]-2-cyclopenten-1-yl}-Nhydroxyurea, amylase, aureomycin, bacitracin, beta carotene, cephalosporins, chloromycetin, cimetidine, cisapride, cladribine, clorazepate, deramciclane, didanosine, digitalis glycosides, dihydrostreptomycin, erythromycin, etoposide, famotidine, hormones (in particular estrogens, insulin, adrenalin and heparin), lipase, milameline, novobiocin, pancreatin, penicillin salts, polymyxin, pravastatin, progabide, protease, quinapril, quinoxaline-2-carboxylic acid, [4-(R)carbamoyl-1-(S-3-fluorobenzyl-2-(S),7-dihydroxy-7-methyloctyl]amide, quinoxaline-2-carboxylic acid[1-benzyl-4-(4,4-difluoro-1-hydroxycyclohexy 1)-2-hydroxy-4-hydroxycarbamoyl-butyl]-amide, ranitidine, streptomycin, subtilin, sulphanilamide and acid-labile proton pump inhibitors like esomeprazole, lansoprazole, minoprazole, omeprazole, pantoprazole or rabeprazole. Digestive proteins such as amylase, lipase and protease may be included in disclosed carrier systems. Amylases, lipases and proteases which are suitable as digestive enzyme supplement or digestive enzyme substitute in mammals, particularly humans, are preferred. Amylase, lipase and/or protease may be derived from microbial or animal, in particular mammalian, sources. Pancreatin is a acid-labile drug. Other therapeutic proteins or peptides may be used with the disclosed carriers to increase bioavailability. Other therapeutic proteins may include, without limitation, insulin, erythropoietin, or fragments or derivatives thereof. Example of glycosaminoglycan include, without limitation, heparin, or fragments thereof. The foregoing list of acid-labile drugs is not meant to be exhaustive, but merely illustrative as a person of ordinary skill in the art would understand that many other acid-labile drugs or combination of acid-labile drugs could also be used.

Nutraceutical Agents

Suitable nutraceuticals for use in the compositions of this invention include, without limitation, any nutraceutical agent that is capable with the carriers of this invention. In certain embodiments, the nutraceutical agents are solid. In other embodiments, the nutraceutical agents are oil soluble liquids or oil miscible liquids.

Biocompatible Oils

Suitable biocompatible oils include, without limitation, any oil approved for a human, mammal or animal consumption by the FDA or other governmental agency. Exemplary biocompatible oils include, without limitation, plant derived oils or animal derived oils or their derivatives or synthetic oils. In certain embodiments, the natural oils are oils rich in phospholipids such as lecithin oils from soy beans. Exemplary examples of plant derived oils or animal derived oils or their derivatives or synthetic oils include, without limitation, essential oils, vegetable oils an hydrogenated vegetable oils such as peanut oil, canola oil, avocado oil, safflower oil, olive oil, corn oil, soy bean oil, sesame oil, vitamin A, vitamin D, vitamin E, or the like, animal oils, fish oils, krill oil, or the like or mixture thereof.

In certain embodiments, the biocompatible oil is a neutral lipid. Suitable neutral lipid include, without limitation, any neutral lipid such as the triglyceride. For a partial listing of representative neutral lipids, such as the triglycerides, reference is specifically made to U.S. Pat. Nos. 4,950,656 and 5,043,329. Both saturated and unsaturated triglycerides may be employed in the present compositions, and include such triglycerides as tripalmitin (saturated), triolein and trilinolein (unsaturated). However, these particular triglycerides are listed here for convenience only, and are merely representative of a variety of useful triglycerides, and is further not intended to be inclusive.

Animal fats include, without limitation, lard, duck fat, butter, or mixture or combination thereof.

Vegetable fats include, without limitation, coconut oil, palm oil, cottonseed oil, wheat germ oil, soya oil, olive oil, corn oil, sunflower oil, safflower oil, hemp oil, canola/rapeseed oil, or mixture and combinations thereof.

Other Additives, Excipients or Adjuvants

The formulation or compositions of this invention can also include other chemicals, such as anti-oxidants (e.g., Vitamin A, C, D, E, etc.), trace metals and/or polyvalent cations (aluminum, gold, copper, zinc, calcium, etc.), surface-active agents and/or solvents (e.g., propylene glycol/PPG, dimethy sulfoxide/DMSO, medium chain triglycerides/MCT, etc.), non-toxic dyes and flavor enhancers may be added to the formulation as they are being prepared to improve stability, fluidity/spreadability, permeability, effectiveness and consumer acceptance. These additives, excipients, and/or adjuvants may also function as active agents.

Experiments of the Invention

The carriers of this invention and compositions including the carriers of this invention possess the capability of targeted release of an active agent into the selected regions of gastrointestinal (GI) tract. Carrier-mediated targeted release is particularly useful for active ingredients that are: (a) injurious to the upper GI tract (esophagus, stomach, and duodenum), (b) acid labile, (c) impermeable/insoluble compounds GI fluids, (d) susceptible to first pass metabolism, and (e) cause stomach irritation, upset, or dyspepsia. In certain embodiments, the targeted release is a pH dependent release so that the active agent(s) is (are) released minimally at low pH of the stomach (e.g., a pH less about 3-<pH 3) and are efficiently released at higher pH of the upper duodenum (e.g., at pH greater than to or equal to 4 to 5). In certain embodiments, the targeted release is a pH dependent release so that the active agent(s) is (are) released minimally at low pH of the stomach (e.g., a pH less about 3-<pH 3) and upper duodenum (e.g., at pH greater than to or equal to 4 to 5), and are efficiently released at the higher pH of the small intestine in presence of high concentration of bile. In certain embodiments, the pH dependent release of the active agent(s) is due to the inclusion in the carrier of pH dependent release agents such as oils including at least one carboxylic acid group or at least one oil soluble or miscible compound including at least one carboxylic acid group. In other embodiments, the oils including at least one carboxylic acid group or at least one oil soluble or miscible compound including at least one carboxylic acid group are free fatty acids. Fatty acids are particularly useful for tailored release along the GI tract because most fatty acid are nonionized or neutral form at gastric pH, but are ionized at intestinal pH which enables them to selectively the active ingredient payload. The studies summarized in this section provide evidence for use of carriers for 1) pH dependent release, 2) targeted dissolution along the GI tract, 3) targeted release enable reduction of GI toxicity of active agents, 4) targeted release of a variety of active agents, and 5) use of pH dependent release carriers for improving the bioavailability of active agents such as acid labile actives, insoluble compounds GI fluids and susceptible to first pass metabolism.

pH Dependent Release of Actives

Our prior studies have suggested that purified phosphatidylcholine (PC) (e.g., Phospholipon 90G) and a lecithin oil (e.g., Phosal 35SB (PS35SB)) increase the partition of aspirin (Log $P_{cyclohexane/0.1N\ HCl}$) in a pH dependent manner. The partitioning (Log P) value was maximal at 0.1 N HCl, with little or no modification in partitioning at neutral pH. These data suggest a pH dependent partitioning of aspirin (ASA) when ASA is dispersed in a lecithin oil carrier (i.e., having attributes of Lecithin NF). The pH dependent partitioning was thought to be due to either the carrier or particular carrier components due to interactions between the carrier and/or its components and the pharmaceutical agent (e.g., NSAID). As lecithin is predominately a complex mixture of phospholipids, triglycerides, and free fatty acids, it was unclear if the free fatty acids inherently in the lecithin or the lecithin carrier conferred the pH sensitivity of the partitioning of aspirin. Therefore, the pH dependent changes in hydrophobicity afforded by a free fatty acid were tested by two methods; partitioning (Log P) and in vitro dissolution.

Preparation of ASA-FFA and FFA/PC Carrier Composition

In this study, ASA-FFA and FFA/PC carrier compositions having differing weight ratios of aspirin and FFA were prepared. The compositions were prepared by admixing powdered ASA into each carrier and heating the mixtures to a temperature of 35° C. for about 30 minutes. The composition formulas are given in Table I.

TABLE I

Make Up of ASA-FFA and ASA-FFA/PC Compositions

| Name | Carrier Components | Carrier Weight Ratio | ASA to Carrier Weight Ratio |
|---|---|---|---|
| ASA | None | N/A | 0 |
| 10:1 ASA:SFFA | Oleic Acid | N/A | 10:1 |
| 1:1 ASA:SFFA | Oleic Acid | N/A | 1:1 |
| 1:10 ASA:SFFA | Oleic Acid | N/A | 1:10 |
| 1% PC* 1:1 ASA:SFFA** | Oleic Acid/PC* | 99:1 | 1:1 |
| 5% PC* 1:1 ASA:SFFA** | Oleic Acid/PC* | 95:5 | 1:1 |
| 10% PC* 1:1 ASA:SFFA** | Oleic Acid/PC* | 90:10 | 1:1 |
| ASA:PS35SB** | PS35SB*** (PL/TG/FFA) | 45:30:11 | 1:1 |

*phosphatidylcholine added as the purified phosphatidylcholine 90G (Lipoid LLC).
**SFFA is soy free fatty acids (Peter Cremer Company).
**an engineered lecithin oil (Lipoid LLC) containing about 45 wt. % phospholipids.

Free Fatty Acids Increases Partitioning of Aspirin (ASA) in a pH Dependent Manner The compositions of Table I were tested in a two phase partitioning system. In this system, the Log P value of aspirin (ASA) was measured in two immiscible solvents: cyclohexane and 0.1N HCl. Cyclohexane was used to mimic a purely hydrophobic surface such extracellular gastric mucosa. HCl (0.1N) was used to simulate gastric fluid. In U.S. Pat. Nos. 4,950,656, 5,043,329, 5,763,422, and 5,955,451, triglycerides in combination with zwitterionic phospholipids were used to reduce toxicity, to increase the cyclohexane solubility of NSAIDs at pH's above their pKa's, and to improve NSAID efficacy. U.S. Pat. Nos. 5,763,422, and 5,955,451 specifically demonstrated that DPPC increased the solubility of ASA in cyclohexane at pH's above their pKa's and that the addition of triglycerides such as trioleate and tripalmitin enhanced this increased solubility. These prior art teachings showed that phospholipids and mixture of phospholipids and triglycerides increases ASA solubility at pH's near the pKa of ASA in cyclohexane, similar to the operation of a phase transfer agent. However, these patents included no teaching that free fatty acids would function as acceptable carriers for pharmaceutical agents such as ASA or that they would be carriers capable of pH dependent release of ASA.

We show here that Log P values of ASA-SFFA formulations may be tailored to have Log P values comparable to 1:1 weight ratio formulations of ASA and Phosal 35SB (PS35SB), an engineered lecithin oil. We have also shown that (1) ASA carriers composed of FFA alone had Log P values comparable to the ASA-PS35SB formulations, (2) ASA carriers with low levels of phospholipids (e.g., 10 wt. %) had Log P values comparable to ASA-PS35SB formulations; and (3) ASA carriers without FFA had release characteristics similar to immediate release aspirin. Thus, the carriers may be tailored to release active agents into different pH environments and/or the level of release may be modulated within given regions of the GI tract based on: (1) the ratio of the FFA and the secondary complexing agents or other carrier components (e.g., FIG. 3 and FIG. 14) and/or (2) the ratio of the carrier to the active agents (e.g., FIG. 1). We believe that the Log P values are predictive of improved NSAID GI safety or reduced NSAID GI toxicity as is shown in the animal study described herein (e.g., FIGS. 12 and 13).

Figure 1:
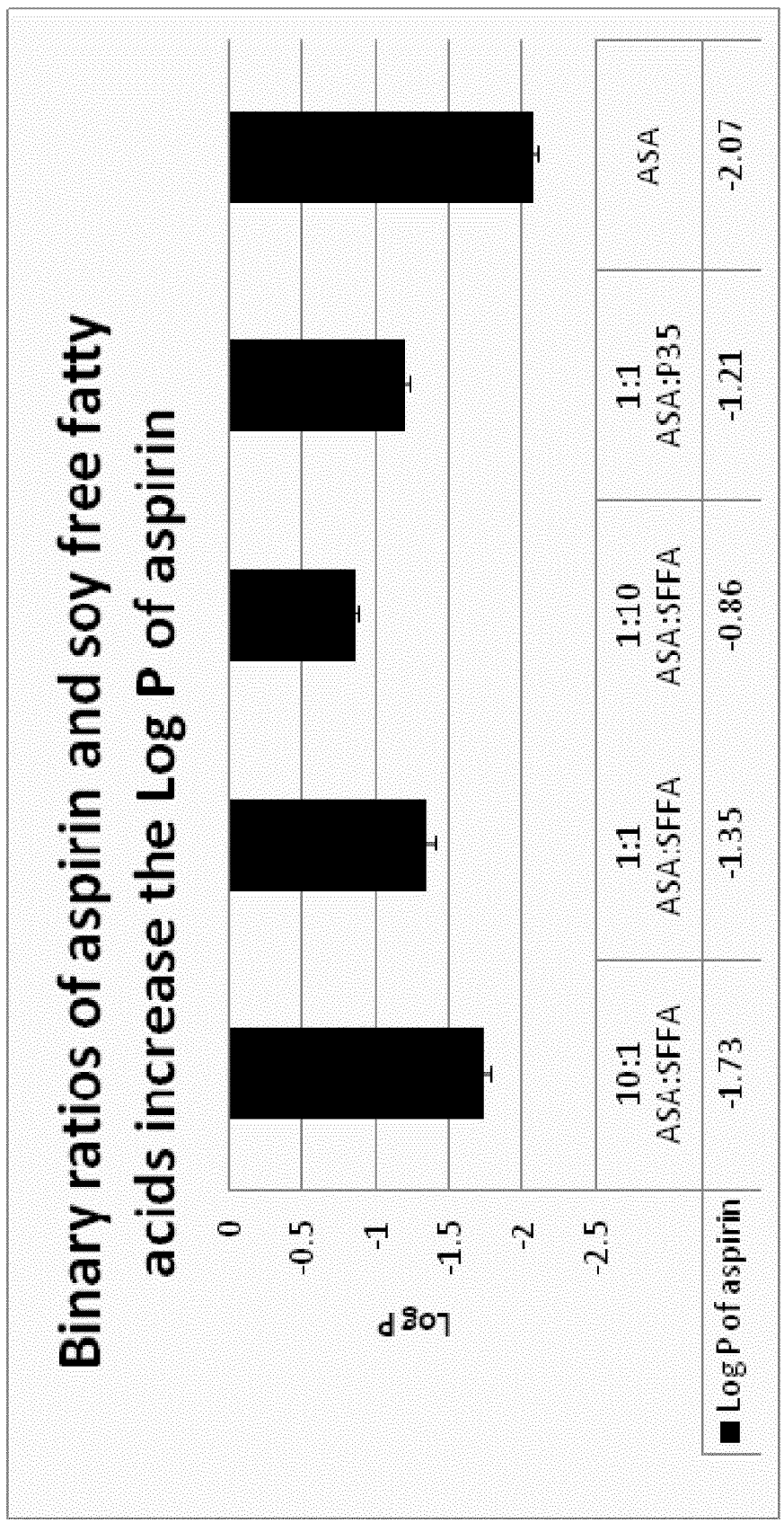
FIG. 1 depicts partitioning (Log P) data for acetylsalicylic acid (ASA) and soy derived free fatty acid (FFA) compositions at 10:1, 1:1 and 1:10 weight ratios, prepared simply by admixing and heating at 35° C. for 30 minutes, to an ASA triple strength lecithin product (ASA:Phosal 35 SB) in a 1:1 weight ratio and 100% ASA. The triple strength lecithin product (P35) is Phosal 35SB. Equivalent amounts of aspirin were used in each formulation tested for Log $P_{cyclohexane/0.1N\ HCl}$. ASA concentration was measured in the respective solvents by HPLC. Data are mean±SD of three replicate determinations.

Referring now to FIG. 1, soy pure FFA (SFFA) alone increases the partitioning of aspirin in a concentration dependent manner into an water immiscible phase; thus, the ratio of active agents to carrier modulates the partitioning characteristics of the composition. A composition including 1:1 weight ratio of aspirin and a 100% FFA carrier had similar Log P values as a 1:1 weight ratio of aspirin and a high phospholipid lecithin oil carrier, PS35 SB (e.g., ~45% phospholipid), suggesting that the 100% FFA carrier may facilitate increased lipid solubility of aspirin similar to that of a high phospholipid lecithin carrier. We also show that the FFA in the carrier interacts with the aspirin at the molecular level as shown by FTIR data herein. Such interactions may be in the form of non-covalent association complexes between the aspirin and the FFA. We also demonstrate below that 100% FFA or oil based carriers including a sufficient amount of FFA are capable of pH dependent release of pharmaceutical agents such as NSAIDs. This data and the other data set forth herein show that carriers with sufficient pH dependent release agents such as FFAs are capable of releasing NSAIDs in a pH specific fashion (i.e., the compositions have minimal release at low pH and efficient release at higher pH) should be generalizable to pharmaceutical and/or nutraceutical agents that are neutral in their solid form, are weak acids, and potentially weak bases.

Figure 2:
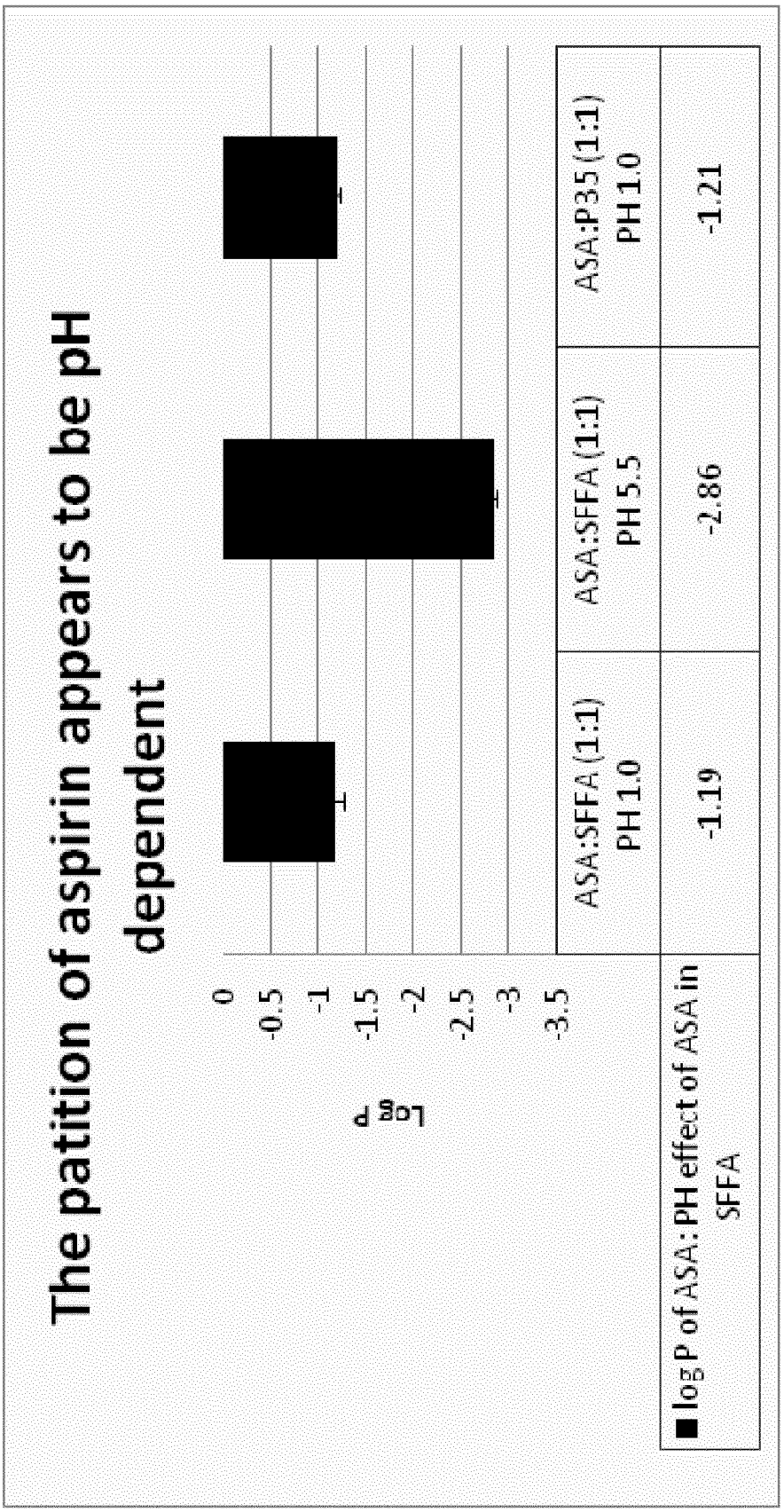
FIG. 2 depicts partitioning (Log P) data for binary ratio of ASA and FFA at 1:1 weight ratios were prepared simple admixture and heating 35° C. for 30 min in creating aspirin suspension of ASA in soy FFA at two pH values comparted to ASA:Phosal 35 SB is a 1:1 weight ratio of aspirin and triple strength lecithin product (Phosal 35 SB). Equivalent amount of aspirin in the form of various formulations were tested for Log $P_{cyclohexane/0.1N\,HCl}$. ASA concentration was measured in the respective solvents by HPLC at the indicated pHs. Data are mean±SD of three replicate determinations.

Referring now to FIG. 2, increased FFA-induced partition of aspirin into a water immiscible solvent such as cyclohexane is pH dependent. The increased partitioning of aspirin across a pseudo-hydrophobic membrane by FFA suggests that FFA alone may modify the physicochemical and/or release behavior of aspirin. This observation further suggests that a binary ratio of aspirin and FFA may improve the gastrointestinal safety of aspirin in a similar manner as found in high phospholipid lecithin oil carriers such as PS35SB. Although not meaning to be tied to any particular theory, the interaction of FFA and ASA may involve the interaction between the carboxylic acid group of aspirin and the carboxylic acid group of the FAA. Carriers having high concentrations of FFA and no or low concentrations of phospholipids appear to have similar characteristics to high phospholipid lecithin oil carriers. These carriers contain approximately 46 wt. % phospholipids and are derived from crude soy bean lecithin. They are engineered lecithin oil in that the original triglycerides have been removed and replaced by sunflower oil and approximately 11 wt % of a mixture of oleic acid and linoleic acid. Two such lecithin oil products are Phosal 35 SB (PS35 SB) and Epikuron (135F). This FFA-aspirin behavior supports compositions that would include no or unusually low levels of phospholipids, levels of zero to less the 10 wt % phospholipid and no or unusually low levels of triglycerides, levels of zero to less the 10 wt % neutral lipids. Alternatively, we believe that FFA may act as a pH dependent release agent due primarily to the nature of FFA. At low pH, FFAs are uncharged and act essentially as a biocompatible oil. However, as the pH is raised, FFAs ionize forming FFA salts, which are known surfactants. Surfactants are known to increase the release of pharmaceutical agents such as NSAID from oil based carriers as we use a surfactant rich buffer system to perform NSAID dissolution such of pre-commercial N SAID-PS35 S B formulations.

In U.S. patent application Ser. No. 12/883,873, improved NSAID GI safety was mediated by oil based carriers including greater than 10 wt. % phospholipid; in fact, the compositions used in the examples included about 46 wt. % phospholipid as that is the approximate phospholipid content of PS35SB, a high phospholipid lecithin oil carrier. Moreover, the use of a carrier containing any amount of phospholipid to augment the bioavailability and toxicity of an NSAID in a tailored matter was not contemplated. As FFA-ASA compositions have similar Log P values compared to PS35SB-ASA compositions, we determined that a new class of carriers for pharmaceutical and/or nutraceutical agents such as NSAIDs may be developed using FFA as a key constituent for a pH controlled release of the active agents. In the data that follows, we demonstrate that carriers including FFAs efficiently release the pharmaceutical agents and/or nutraceutical agents at a pH greater than about pH 3, while non-FFA containing oil based carriers efficiently release the active agents at a pH less than about 3.

Figure 3:
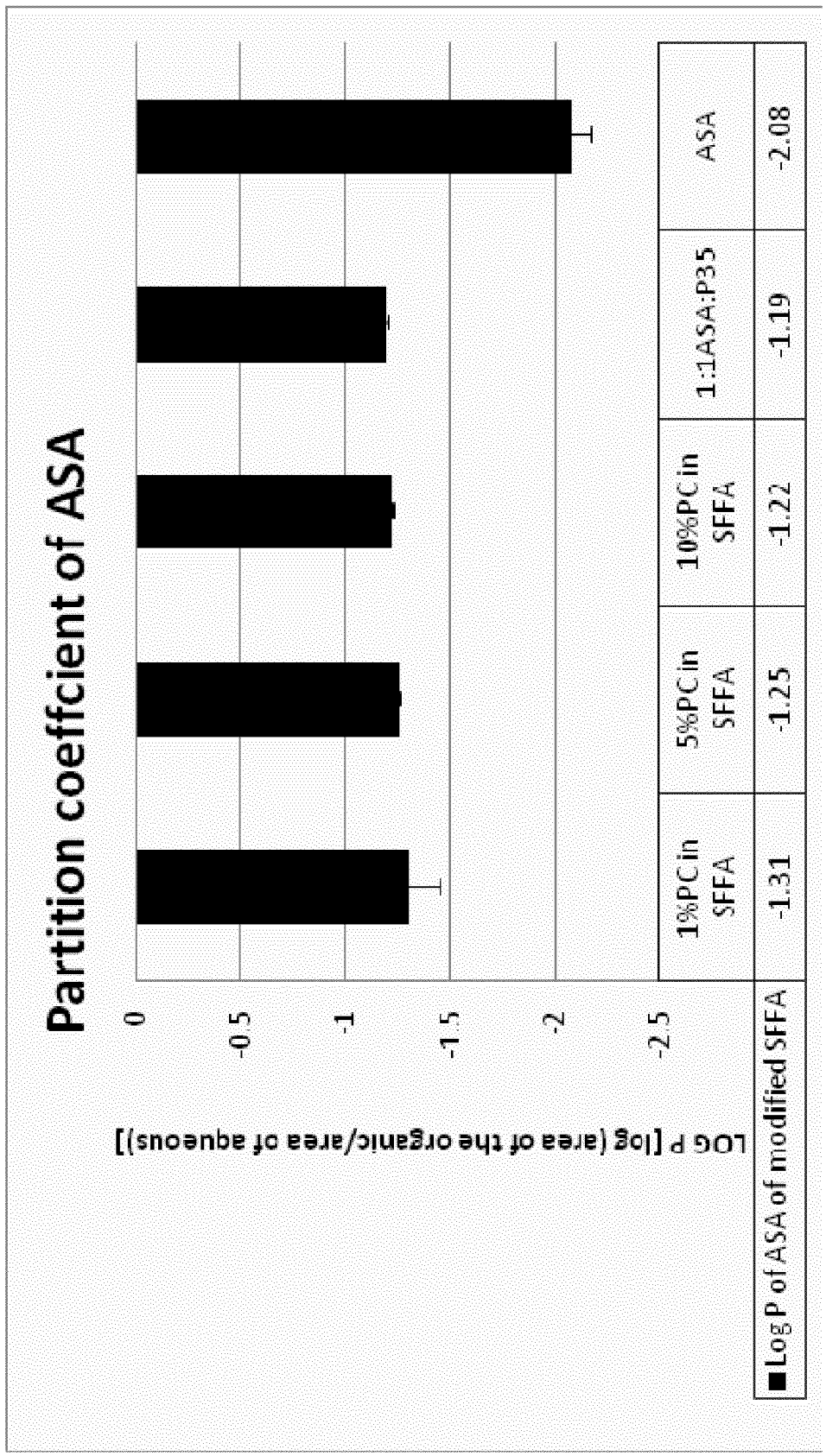
FIG. 3 depicts partitioning (Log P) data for ASA:FFA carriers including 1 wt. %, 5 wt. %, and 10% w/w PC compared to ASA:P35 is a 1:1 weight ratio of Aspirin alone, where P35 (Phosal 35 SB). Equivalent amounts of each preparation was tested for Log $P_{cyclohexane/0.1N\,HCl}$. Data are mean and SD of triplicate determinations. The formulation were prepared by admixing with aspirin on 1:1 weight basis in to the carrier.

We have also determined that FFA carriers may be modified by the addition of low levels of phospholipid giving rise to similar Log P values when aspirin is the NSAID. The fact that these FFA carriers have similar Log P values for ASA is unexpected in light of the teaching in the prior art, where the phospholipid content was assumed to be the operative constituent in lowering GI toxicity of NSAIDs. As shown in FIG. 3, high FFA carriers were effective carriers of PC and provided similar partition values for aspirin with phospholipid (PC here) contents between 5 wt. % and 10 wt. % compared to a PS35SB carrier containing about 45 wt. % PC; and thus, the carrier are tailorable by the ratio of FFA to secondary complexing agents in the carrier. These data suggest that phospholipid levels required to mediate GI safety could be markedly reduced from approximately 45 wt. % phospholipid to ≤10 wt. %. The data also suggests that FFA carriers may be effective NSAID carriers in the absence of any phospholipid. FFA carriers having low phospholipid amounts would also have added stability and cost benefits over existing by phospholipid carriers, which have been shown to undergo considerable phospholipid degradation-loss of the ester side chains.

The fact that carriers including low levels of or no phospholipid behave in a similar manner to Phosal 35 SB (PS35SB), a carrier including approximately 45 wt. % phospholipid, is wholly unexpected. Even more unexpected is that ASA partitioning in a pure FFA carrier shows definite pH dependencies similar to PS35SB. We believe that we now have alternative carriers for use with pharmaceutical and/or nutraceutical agents that avoid the complications of relatively expensive, hydrolytically, and thermally unstable phospholipids.

We illustrate some of the properties of the carries of this invention by reference to aspirin (ASA) carrier compositions, where the carriers include neutral lipids, free fatty acids, and phospholipids. One type of high phospholipid carrier is a triple strength lecithin product sold as Phosal 35 SB. Up to now it had been assumed that the NSAID complexing agents in carriers containing phospholipids were phospholipids, of which phosphatidylcholine is present in the greatest concentration. However, we believe that the free fatty acids may comprise a second group of components that may form reversible complexes with ASA. We also believe that neutral lipids may also form a third group of components that may form reversible complexes with ASA. Besides providing components for non-covalent complexation of ASA, the other carrier components may play a role in the activity of the ASA complexes including ASA-PC complexes and in the dispersal of the compositions in water. The present study is directed to dissolution procedures pertaining to a triple strength lecithin-ASA composition to assess pH dependent release to simulate API release across the GI tract.

pH Dependent Increased Hydrophobicity Results in pH Dependent Dissolution

In this analysis, the release of ASA from the triple strength lecithin oil PS35SB carrier-ASA composition (PS35 SB-ASA) was compared to that of immediate release aspirin. PS35 SB-ASA was filled into hard shelled capsules and immediate release aspirin tablets were tested. Dissolution rates were measured in a United States Pharmacopia (USP) Type II apparatus using the various media preparations.

In this analysis, the release of ASA from PS35SB-ASA was compared to that of plain aspirin tablets. The PS35SB-ASA composition filled into hard shelled capsules and plain aspirin tablets were tested. The release of aspirin from the two dose forms were evaluated per USP <711> using a Type II dissolution apparatus, at 37° C. in a vessel containing 900 mL of various citrate phosphate buffers at 3.5, 4.5, 5.5, 6.9, 7.4, at 150 rpm paddle speed.

The rate of release was monitored by sampling the dissolution vessels at 5, 10, 15, 30, 45, 60, 75, and 90 minutes, and infinity samples. The fraction of aspirin released and dissolved from the two dose forms was monitored by HPLC.

The HPLC method used to measure the release of acetylsalicylic acid and salicylic acid is isocratic elution at 1.2 mL per minute, with a 60/40/0.2 water/acetonitrile/phosphoric acid mobile phase. The column used was an ODS3 "Inertsil", 5 µm, 250×4.6 mm by ES Sciences. Standards were prepared by dissolving and diluting aspirin, manufactured by Rhodia, into mobile phase.

Figure 4:
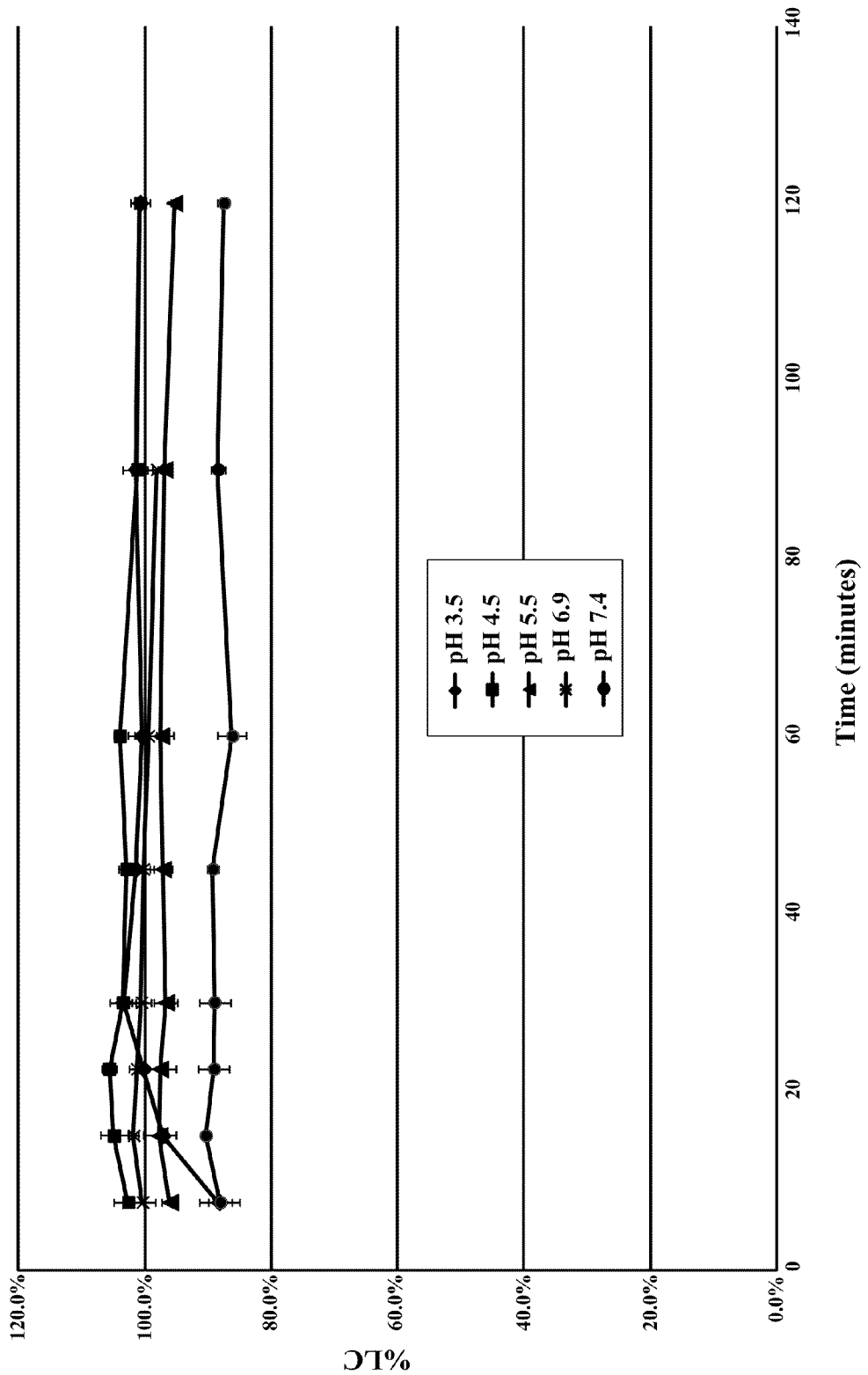
FIG. 4 depicts dissolution profiles of immediate release aspirin tablets at various pH levels. The data are mean±standard deviation (SD) of replicate determinations.
Figure 5:
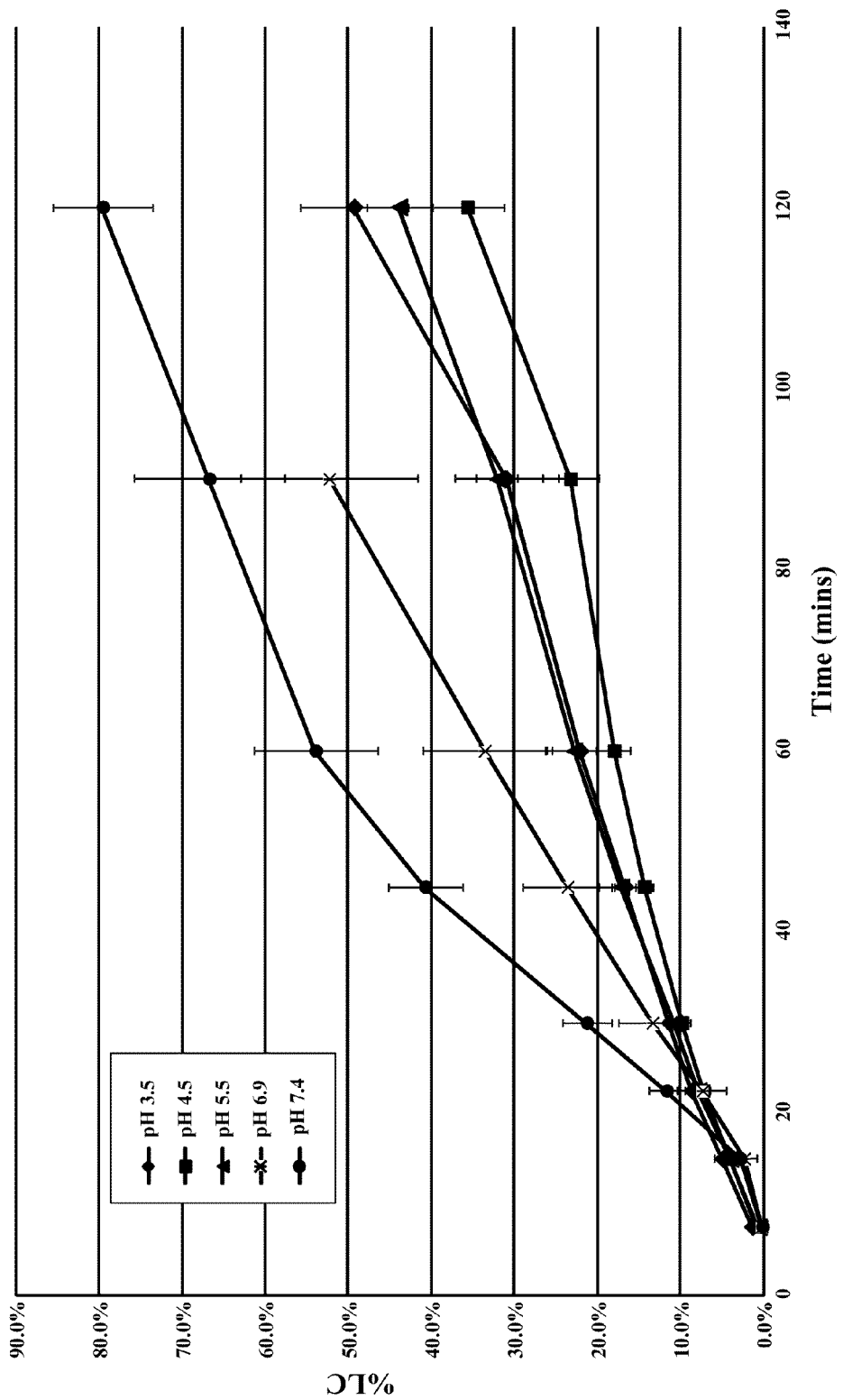
FIG. 5 depicts dissolution profiles of the triple strength lecithin carrier-ASA composition filled capsules at various pH levels. The data are mean±standard deviation (SD) of replicate determinations.

Referring to FIG. 4, dissolution profiles of immediate release ASA tablets at different pH values is shown, while FIG. 5 shows the dissolution profiles of a PS35SB-ASA composition at different pH values.

The immediate release aspirin tablets began to disintegrate immediately when introduced to the dissolution and were completely dissolved in the first five minutes for all pH levels.

In contrast, the PS35SB-ASA filled capsules showed shell disintegration starting after approximately ten minutes. Upon rupture of the capsule, fill material was released, dispersed and dissolved in a pH dependent manner as show in FIG. 5.

The aspirin released from PS35SB-ASA composition (see FIG. 5) clearly showed an increase with increasing pH, suggesting that the release of aspirin from the lecithin oil matrix is pH dependent. While not intending to be bound by any theory, it is thought that the increased rate of release at higher pH is due to the ionization of carboxylic acid group of aspirin. Thus, the aspirin release from the PS35SB carrier or matrix increases with pH, as demonstrated above in FIG. 5. However, it has become clear that the pH dependent properties of PS35SB may be solely due to the presence of a sufficient amount of fatty acids in the PS35SB carrier as carriers including only triglycerides and phospholipids showed reduced to no pH dependent characteristics for ASA illustrated in FIG. 6.

To determine if the free fatty acids in the lecithin oil PS35SB mediated the pH dependent release, the release of aspirin from four preparations containing 325 mg of aspirin in tablet or capsule form as summarized in Table II were measured in simulated gastric fluid (0.1HCl) per USP <711>.

TABLE II

Capsule Fill Formulas

| Component | | A | B | C |
|---|---|---|---|---|
| Aspirin | | 49 | 49 | 49 |
| PS35SB* | | | | 49 |
| Carrier | PC | 19.6** | 19.6 | 20.58** |
| Composition | TG | 29.4*** | 14.7 | 13.72*** |
| | FFA | | 5.4 | 14.7**** |
| | Other† | | 9.3 | |
| Silicon Dioxide | | 2 | 2 | 2 |
| Total | | 100 | 100 | 100 |

Figure 6:
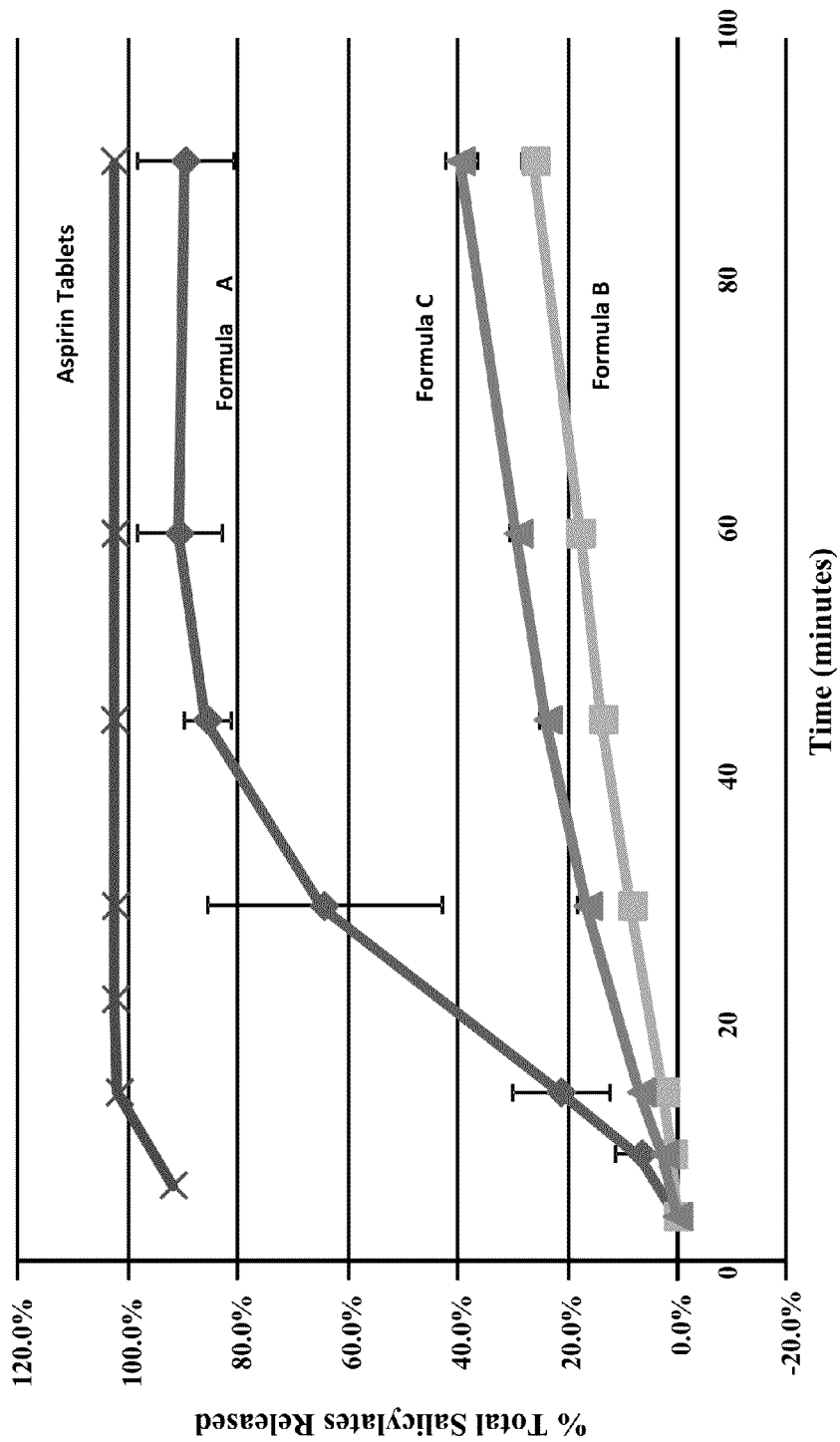
FIG. 6 depicts dissolution of aspirin (ASA) compared to carries with and without free fatty acids (FFAs). The data are mean±standard deviation (SD) of replicate determinations.

*Phosal 35SB an engineered lecithin oil - component break down shown in grey based on 49 wt. % Phosal 35SB.
**Purified soy phosphatidylcholine (S100, Lipoid LLC)
***Triglycerides derived from Soy bean oil.
****FFA used was oleic acid (Croda)
†other ingredients found in Phosal 35SB Formulas A-C were prepared by admixing ASA into the carrier at 40° C. with mixing as described herein. The lecithin oil contains approximately 40 wt. % phosphatidylcholine, 40 wt. % triglycerides, 13 wt. % free fatty acids. As shown in FIG. 6, release of aspirin from the lecithin oil was minimal. As the release from the TG/PC only carrier was rapid and is highly attenuated by the addition of a FFA; thus, the pH sensitive release afforded by the lecithin oil as described in FIG. 5 is due primarily to the presence of the FFA.

Targeted Release of Aspirin Along the GI Tract

As previously shown, the pH sensitive hydrophobicity results in pH sensitive release and dissolution. As the physiological milieu is dramatically different between stomach, upper duodenum and the intestine, the targeted release as assessed by in vitro dissolution of three carriers described in Table III were evaluated in simulated gastric, duodenal and intestinal fluids dissolution characteristics of formulations including an oleic acid carrier, an oleic acid/2.5 wt. % PC carrier, and PS35SB carrier. The formulations were prepared by adding the ingredients listed in Table III and stirring the mixtures as 35° C. for 30 minutes, except for the ASA formulation that is a tablet, while the other formulations are filled into hypermellose capsules.

TABLE III

Ingredients Used in the Formulations

| Formulation | Component | Weight (g) | wt. % |
|---|---|---|---|
| ASA | Aspirin | 19.6000 | 100 |
| P1 | Oleic Acid | 19.6113 | 49.00 |
| | S100* | 0.0000 | 0.00 |
| | Aspirin | 19.6142 | 49.00 |
| | Silicon Dioxide | 0.8002 | 2.00 |
| P2 | Oleic Acid | 18.7541 | 46.51 |
| | S100* | 1.0072 | 2.50 |
| | Aspirin | 19.7604 | 49.00 |
| | Silicon Dioxide | 0.8046 | 2.00 |
| AC2 | P5355B** | 25.7060 | 49.00 |
| | Aspirin | 25.7077 | 49.00 |
| | Silicon Dioxide | 1.0494 | 2.00 |

*purified soy phosphatidylcholine (Lipoid LLC)
**an engineered lecithin oil carrier Referring now to FIG. 7, the dissolution profiles in of ASA, P1, P2 and AC2 were tested in simulated gastric fluid consisting of 0.1 N HCl having a pH 1 in a USP Type II apparatus at 37° C. at 150 rpm paddle speed.

Referring now to FIG. 8, dissolution profiles in "simulated upper duodenal fluid" pH 4.5 at 150 rpm.

Referring now to FIG. 9, dissolution profiles in "simulated intestinal fluid" pH 7 dissolution buffer (bicarbonate buffer with 20 mM cholic acid and 1% pancreatin) at 150 rpm. This media is a fed variant of USP intestinal fluid (pH 7.2 phosphate buffer, 1% pancreatin).

Referring now to FIGS. 10A&B, a side by side comparison of average dissolution profiles of 0 wt. % PC and 2.5 wt. % PC formulations in different media: 0.1 N HCl, a dissolution buffer (bicarbonate buffer with bile acids and enzymes), an acetate buffer, and a phosphate buffer.

The above dissolution data provides compelling support for the use of fatty acid based carriers (i.e., carriers that include a sufficient amount of a fatty acid to render the carrier capable of pH dependent release) as carrier for active agents that are known to have GI toxicity such as NSAID, active agents that are degraded in low pH environments such as in gastric fluids, active agents that are better absorbed in the upper part of the small intestines, and/or active agents that are targeted for release after passing through the stomach, but that do not require release at high pH found in the lower GI tract.

Referring now to FIG. 11, a picture of the upper GI track stomach to small intestines (duodenum, jejunum and ileum) is provided to show the marked differences in physicochemical properties of the various sections of the GI tract. The differences in pH and bile acids concentration and composition, digestive enzymes could be exploited to enable targeted release of actives using the various lipid carriers. The present ASA Formulas including FFA clearly show pH dependent ASA release in accordance with the pH change from the stomach through the various parts of the small intestine. Thus, the carriers including an amount of FFA sufficient to reduce or minimize ASA release in the stomach or at low pH, while increasing or maximizing ASA release in the small intestine as the pH increases along the distal part of the small intestine. The carriers of this invention including an amount of FFA are, therefore, well suited for tailored release of active agents such as pharmaceutical and/or nutraceutical agents in the duodenum with reduced or minimized release of the active agents in the stomach. As will be shown herein, the pH characteristics of the carriers of this invention including this sufficient amount of FFA are generalizable to NSAID and based on the fact that solid materials are dispersed in the carriers, the carriers' pH characteristics should be generalizable to all solid active agents dispersed in these carriers.

Targeted Release of Aspirin Along the GI Tract May Decrease Gastric Damage

As the FFA alone, FFA in combination with low PC, lecithin provide selective release and dissolution of aspirin in simulated intestinal fluids and aspirin release in the stomach is known to induced erosive damage, the ability of selective carrier mediated release on gastric and intestinal damage was evaluated in the rat. Rats were administered by oral gavage mini-capsules containing aspirin at 40 mg/kg in carrier formulations in Table VIII, along with a methylcellulose negative control, and pulverized immediate release aspirin.

The experimental controls used in this study include: (1) a control composition (NAC) comprising Methyl Cellulose from Sigma Chemical Company, Product No. M-0512, Lot No: 74F-0466, which was stored in controlled ambient temperature; (2) 325 mg OTC Aspirin (AC1) from Walgreen Co, Product No. P53405, and (3) 325 mg Aspirin in Phosal 35SB carrier (AC2).

Two compositions P1 and P2 of this invention were prepared along with AC2. AC2, P1 and P2 had the ingredient formulations shown in Table IV and were stored during the study under controlled ambient temperature and protected from light.

TABLE IV

Ingredient Formulations

| Formula | Component | Weight (g) | Ingredient |
|---|---|---|---|
| P1 | Lipid Carrier | 19.6113 | Oleic Acid |
|  | Active Ingredient | 19.6142 | Aspirin |
|  | Viscosity Modifier | 0.8002 | Cab-o-Sil M5P |
| P2 | Lipid Carrier | 1.0072 | S100 (Purified Soy PC) |
|  |  | 18.7541 | Oleic Acid |
|  | Active Ingredient | 19.6142 | Aspirin |
|  | Viscosity Modifier | 0.8002 | Cab-o-Sil M5P |
| AC2 | Lipid Carrier | 25.7060 | Phosal 35SB |
|  | Active Ingredient | 15.7077 | Aspirin |
|  | Viscosity Modifier | 1.0494 | Cab-o-Sil M5P |

The formulations P1, P2, and AC2 were prepared by: 1) lipid components were mixed and incubated at 40° C. for one hour with occasional mixing to insure lipid carrier homogeneity; 2) aspirin was mixed into the lipid carrier; 3) a viscosity modifier was added to the lipid carrier/aspirin mixtures; 4) the formulations were mixed until homogeneous and incubated at 40° C. for 60 minutes; and 5) the formulations were stored at ambient conditions and mixed well before use.

Forty (40) male Sprague-Dawley rats, approximately 10 weeks of age, were used in this study. Animals were randomly distributed among 5 treatment groups, 8 rats per group.

TABLE V

Animals Randomized to Each Treatment Group

| Group | Aspirin Dose (mg/kg/day) | Aspirin (mg/mini-cap) | # Rats Dosed |
|---|---|---|---|
| NAC[a] | 0 | 0 | 8 |
| AC1 | 40 | 10.14 and 10.79 | 8 |
| P1 | 40 | 19.83 and 19.80 | 8 |
| P2 | 40 | 19.75 and 19.67 | 8 |
| AC2 | 40 | 20.32 and 19.75 | 8 |

Test articles were packed into mini-capsules such that one mini-capsule would provide an intragastric dose of aspirin of 40 mg/kg/day per animal. For preparation of OTC Aspirin, tablets were pulverized using a mortar and pestle and packed into mini-capsules. For P1, P2, and AC2, an appropriate amount of fill material (based on the aspirin content of the fill) was added to the mini-capsules. Dosing formulations were prepared for a 3-day treatment based on the assumption that each animal would gain an average of 3.0 g in body weight during the 3-day experimental period. For example, the mini-cap containing the initial dose of aspirin was assembled for a rat of average Day 1 body weight+3.0 g.

Animals were fasted (with ad libitum access to water) from 8 am to 3 pm prior to dosing; wire-bottom cages were required to prevent animals from eating any bedding or fecal pellets. Doses of aspirin and P1, P2, and AC2 were administered by oral gavage for 3 consecutive days (Study Days 1, 2, and 3) between 2 pm and 3 pm to maximize the potential effects of the study drugs on the stomach, at 40 mg NSAID per kg body weight per day.

Animals were maintained in the fasting state for 1 hour after dosing; food was then available ad libitum until the next morning.

After 3 day of treatment, the rats were sacrificed and the following tissues were collected for analyses stomach, small intestine (jejunum and ileum). The extent of erosive damage in the stomach was evaluated microscopically and level of gastric or intestinal bleeding was evaluated by measuring luminal fluid hemoglobin.

Gastric examination was performed under a dissecting microscope for evidence of erosions and ulcers and dosing-related injury. Specifically, following the wash with distilled water for Hb assay, the stomach was opened by an incision along the lesser curvature, rinsed with normal saline, and blotted dry with #2 filter paper. Gastric lesions observable under the dissecting microscope that could not be removed by rinsing the luminal surface of the dissected stomach with saline were counted and measured. Gastric lesion scoring by animal was recorded.

Two types of gastric lesions were observed: linear and small dot (pinpoint): (1) Pinpoint lesions (0.1 to 1.0 mm in the longest dimension) were each assigned a score of 1 $mm^2$; and (2) Linear lesions (more than 1 mm in length) were measured in length and width. The lesion was assigned a score equal to the area of the lesion in $mm^2$ [length (mm)×width (mm)].

The gastric lesion score of an animal was determined to be the sum of the scores of the pinpoint and linear lesions, an estimate of the total area of gastric lesions. The gastric lesion score of a treatment group was determined to be the average of the gastric lesion scores of the animals in that group.

Hemoglobin (Hb) concentrations in gastric and small intestinal washes and in sonicated solutions of fecal pellets were determined by the benzidine method and measuring optical density (OD) at 515 nm.

Targeted Release of Aspirin Reduces Gastric Damage

Gastric lesions, defined as pinpoint or larger (linear) lesions on gastric mucosa observable under a dissecting microscope, were measured and scored as described below. Gastric lesion scores for each treatment group are presented in FIG. 12. The gastric lesion score (FIG. 12) was lower in all groups treated with P1, P2, and AC2 than in those treated with AC1.

A significant difference between the gastric lesion scores was noted between groups [$F(4, 35)=10.42$, $p<0.0001$, Tukey's HSD]. The gastric lesion score in animals treated with AC1 (15.5±3.7) was significantly higher than in groups treated with P1 (3.6±1.2; $p<0.01$), P2 (5.3±1.5; $p<0.01$), AC2

(1.8±0.7; p<0.01), or in the Control group (0; p<0.01). The gastric lesion score in the control NAC was not different from groups treated with P1, P2, and AC2. No significant differences were noted in gastric lesion scores among the groups treated with P1, P2, and AC2. This reductions in gastric erosive damage by P1, P2, and AC2 was not accompanies by any obvious significant changes in bleeding as luminal hemoglobin levels, except that P1 treated rats had significantly lower Hb concentration than AC1 as shown in FIG. 13. These data suggest targeted release of aspirin to the intestine by either lecithin oil, a free fatty acid alone, or a free fatty acid with a low amount of phospholipid results in reduced gastric damage.

P1, P2, and AC2 have been show to provide pH dependent and as such selective release in small intestinal fluid with minimal release of aspirin in gastric fluid (FIG. 7-9). With all three formulations providing similar improvement in erosive damage to stomach, these data indicate that a carrier comprising of a FFA provides targeted release along GI tract and such targeted release can minimize GI Damage. This observation is particularly unexpected because FFA alone have the propensity to induce upper GI injury.

Use of Carriers to Increase Bioavailability of Poorly Permeable Biologically Active Agents and Other Applications Aspirin is poorly soluble at gastric pH but highly permeable pharmaceutical active agent. In contrast, in the intestine aspirin is highly soluble but poorly permeable across epithelial cells. The octanol/0.1 N HCl system has been used to assess the relative solubility and partitioning of aspirin across intestinal epithelial cells for poorly permeable compounds using aspirin a model compound.

In this study, the partitioning behavior of carrier compositions having different ratio of oleic acid, a free fatty acid (FFA) to a purified triglyceride (TG) in an octanol/0.1 N HCl partitioning system was investigated. The carriers were admixed with aspirin (ASA) to form 1:1 weight ratio of ASA to carrier compositions. The admixing preparation procedure was substantially similar to the admixing methods set forth above. The carriers included: (1) 100 wt. % FFA designated ASA FFA, (2) 80 wt. % FFA and 20 wt. % TG designated ASA 80 FAA:20 TG, (3) 60 wt. % FFA and 40 wt. % TG designated ASA 60 FAA:40 TG, (4) 40 wt. % FFA and 60 wt. % TG designated ASA 40 FAA:60 TG, (5) 20 wt. % FFA and 80 wt. % TG designated ASA 20 FAA:80 TG, and (6) 100 wt. % TG designated ASA TG. The formulations were prepared using two different triglyceride types: a long chained triglyceride (LCT) derived from soybean oil having $C_{16}C_{20}$ side chains and a middle chain triglyceride (MCT) having $C_6$-$C_{12}$ side chains such MIGLYOL® 812 (a registered trademark of Sasol North America).

Referring now to FIG. 14, the partitioning data clearly shows that modifying the ratio of FFA to components of the carrier (e.g., TG) modulates the partitioning across a simulated gastrointestinal membrane. Moreover, the partitioning is further controlled by chemical characteristics or selection of the other components of the carrier. For example, the chain length of glycerides (e.g., TG) is also an important factor in modulating partitioning. These findings indicate two important potential applications of a FFA containing carrier: 1) to increase bioavailability of poorly permeable compounds across gastrointestinal membranes, and 2) enable targeting absorption of actives to via lymphatic circulation and avoid first pass loss. As the Log $P_{octanol}$ increases in the presence of a FFA, and higher Log $P_{octanol}$ is known to be associated with improved bioavailability of poorly permeable actives, a carrier comprising free fatty acids may be used to improve the bioavailability of poorly permeable compounds.

As the chain length of a TG is a known factor for lymphatic partitioning of active agents, the combined use of long chain ($C_{16}$ or greater) FFA and a long chain ($C_{16}$ or greater) TG could enable targeted release along GI tract coupled with improved lymphatic partitioning. With increased lymphatic absorption of an active, the extent of first pass loss could be decreased by decreasing fraction of orally administered biologically active agents from absorption into the mesenteric circulation and the consequent first pass metabolism in the liver.

FTIR Study of Various ASA Formulations

Referring now to FIG. 15, FTIR spectrum of pure aspirin (ASA), 1:1 weight ratio formulation of ASA and PS35SB, 1:1 weight ratio formulation of ASA and linoleic acid, and 1:1 weight ratio of ASA and trioleate are shown in collective plot so that interaction behaviors between ASA and the different carriers may be compared. First, it is apparent that ASA interacts with all three carriers. Put another way, the three carriers cause shifts and spectral feature changes of the ASA ester and carboxylic acid peaks, with the greatest shifts seen for the acid peak, where all carriers shift the acid absorption peak to a higher reciprocal centimeter value. We believe that these interactions between ASA and the carrier components may have some influence on carriers properties such as partitioning properties, dissolution properties, pH dependent release properties, and/or other properties. As the carrier properties are mediated by modification the inonizable free carboxylic acid group aspirin, it may be possible to generalize the carrier mediated-targeted release to all weak acids. Therefore, the pH dependent change in hydrophobicities for several structurally diverse weak acid NSAIDs were evaluated.

Generalizability of Carrier-Targeted Release to all Weak Acid Biologically Active Agents Salicylic Acid Solvation/Evaporation Method Vs. Admix Method Study In this set of experiments, we found that the method of preparing the compositions is not critical to the behavior of the resulting compositions. Prior art suggested that the method of preparation would result in significant changes in the behavior of the carriers. These examples show that for carrier including a sufficient amount of FFA to render the carriers pH dependent, the compositions may be prepared by a simple admixing of ingredients together in the absence of a solvent or solvent system or may be prepared by dissolving the components in a solvent or solvent system followed by solvent removal. Of course, these method all are performed in the absence of added water, i.e., the ingredients and solvent are generally water free or include only minimal or residual amount of water. Said another way, the methods used to prepare the compositions of this invention are non-aqueous, even though some of the solvent may be water miscible such as ethanol. Thus, the compositions formed by admixing or solvent dissolution followed by solvent removal are oil based compositions including only minimal water or residual water concentrations and are generally oil dispersions of active agents in an oil based carrier.

SA Formula A

This example illustrates the preparation by admixing of a composition including a 1:1 weight ratio of salicylic acid (SA) and a carrier comprising about 40 wt. % of a purified phosphatidylcholine (PC) and a pure triglyceride (TG) designed SA Formula A.

SA Formula A was prepared by admixing 50 wt. % SA into a carrier comprising 30 wt. % triglycerides derived from Soy bean oil and 20 wt. % of purified phosphatidylcholine at a temperature of about 40° C. for about 30 minutes as described above.

SA Formula B

This example illustrates the preparation by admixing of a composition including a 1:1 weight ratio of salicylic acid (SA) and a carrier comprising the lecithin oil Phosal 35SB (PS35SB) designed SA Formula B.

SA Formula B was prepared by admixing 50 wt. % SA into a carrier comprising PS35SB at a temperature of about 40° C. for about 30 minutes as described above.

SA Formula C

This example illustrates the preparation by admixing of a compositions including a 1:1 weight ratio of salicylic acid (SA) and a carrier comprising 42 wt. % of a purified phospholipid, LIPOID® S100 (a registered trademark of Lipoid LLC), 28 wt. % of a purified triglyceride (TG) (Spectrum Chemical Manufacturing Corporation), and 30 wt. % of oleic acid (Spectrum Chemical Manufacturing Corporation) designed SA Formula C.

SA Formula C was prepared by admixing 50 wt. % SA into a carrier comprising 14 wt. % triglycerides derived from Soy bean oil, 15 wt. % oleic acid and 21 wt. % of purified phosphatidylcholine at a temperature of about 40° C. for about 30 minutes as described above.

SA Formula D

This example illustrates the preparation by admixing of a compositions including a 1:1 weight ratio of salicylic acid (SA) and a carrier comprising 5 wt. % of a purified phospholipid, 46.5 wt. % of a purified triglyceride (TG) and 48.5 wt. % of oleic acid designed SA Formula D.

SA Formula D was prepared by admixing 50 wt. % SA into a carrier comprising 23.25 wt. % triglycerides derived from Soy bean oil, 24.25 wt. % oleic acid and 2.5 wt. % of purified phosphatidylcholine at a temperature of about 40° C. for about 30 minutes as described above.

Table VI tabulations the SA Formulas compositions in weight percentages.

TABLE VI

Formula Composition for Salicylic Acid (SA) Study

| Component | SA Formula A | SA Formula B | SA Formula C | SA Formula D |
|---|---|---|---|---|
| SA | 50.0 wt. % | 50.0 wt. % | 50.0 wt. % | 50.0 wt. % |
| PS35SB* | | 50.0 wt. % | | |
| PC** | 20.0 wt. % | 20.0 wt. % | 21.0 wt. % | 2.5 wt. % |
| TG*** | 30.0 wt. % | 15.0 wt. % | 14.0 wt. % | 23.25 wt. % |
| Oleic Acid | | 5.5 wt. % | 15.0 wt. % | 24.25 wt. % |
| Other† | | 9.5 wt. % | | |

*Phosal 35SB an engineered lecithin oil - component break down shown in grey based on 50 wt. % Phosal 35SB
**Purified phosphatidylcholine
***Triglycerides derived from Soy bean oil
†other ingredients found in Phosal 35SB Partitioning Study of SA vs. SA Formulas A-D In this study, pure salicylic acid (SA) partitioning between cyclohexane and water versus salicylic acid partitioning between cyclohexane and water in SA Formulas A-D was investigated at pH 1 and at pH 7 simulating gastric fluids and duodenum fluids. The study was conducted by adding either SA, SA Formulas A-D into a cyclohexane/water partitioning system and measuring the differential partitioning of SA between the two phase as the value Log P.

Referring now to FIG. 16, it is clear that SA partitions differently at pH 1 versus pH7. SA has a Log P of −1.11 at pH 1 and a Log P of 0.00 at pH 7. The partitioning of SA in SA Formulas A-D between cyclohexane and water at pH 1 gives rise to Log P values that are less negative than the Log P value for SA at pH 1. The partitioning of SA in SA Formulas A-D between cyclohexane and water at pH 7 gives rise to Log P values that are much more negative than the Log P value for SA at pH 7.

Dissolution Study of SA Vs. SA Formulas A-C in a Two Stage Dissolution System

In this study, pure salicylic acid (SA) dissolution versus salicylic acid dissolution in SA Formulas A-C was investigated using a two stage dissolution procedure. The procedure related to measuring SA dissolution in a pH 1 dissolution medium comprising 0.1 N HCl to simulate gastric fluids with mechanical stirring at 75 rpm stirring speed. After 60 minutes, the pH of the medium was adjusted from pH 1 to pH 7.2 by the addition of phosphate buffer to a final concentration of 0.05 M while maintaining the same stirring rate. The dissolution was represented as % LC, which is the percentage of SA that dissolves into the media. Measurement were made at 10 minutes, 20 minutes, 30 minutes, 50 minutes, 60 minutes, 70 minutes, 90 minutes, 110 minutes, 120 minutes, 150 minutes, and 180 minutes.

Naproxen

Preparation of NAP Formula A-D

NAP Formulas A

This example illustrates the preparation by admixing of a composition including a 1:1 weight ratio of naproxen (NAP) and a carrier comprising about 40 wt. % of a purified phosphatidylcholine (PC) and a pure triglyceride (TG) designed NAP Formula A.

NAP Formula A was prepared by admixing 50 wt. % NAP into a carrier including 30 wt. % triglycerides derived from Soy bean oil (Spectrum Chemical Manufacturing Corporation) and 20 wt. % of purified phosphatidylcholine from LIPOID® S100 (a registered trademark of Lipoid LLC) at a temperature of about 40° C. for about 30 minutes as descried above.

NAP Formula B

This example illustrates the preparation by admixing of a composition including a 1:1 weight ratio of naproxen (NAP) and a carrier comprising the lecithin oil PHOSAL® 35SB (PS35SB) (a registered trademark of Lipoid LLC) designed NAP Formula B.

NAP Formula B was prepared by admixing 50 wt. % NAP into a carrier comprising 50 wt. % PS35SB at a temperature of about 40° C. for about 30 minutes as described above.

NAP Formula C

This example illustrates the preparation by admixing of a compositions including a 1:1 weight ratio of naproxen (NAP) and a carrier comprising 42 wt. % of a purified phospholipid (Lipoid LLC), 28 wt. % of a purified triglyceride (TG)(Spectrum Chemical Manufacturing Corporation) and 30 wt. % of oleic acid (Spectrum Chemical Manufacturing Corporation) designed NAP Formula C.

NAP Formula C was prepared by admixing 50 wt. % NAP into a carrier comprising 14 wt. % triglycerides derived from Soy bean oil (Spectrum Chemical Manufacturing Corporation), 15 wt. % oleic acid (Spectrum Chemical Manufacturing Corporation) and 21 wt. % of purified phosphatidylcholine (Lipoid LLC) at a temperature of about 40° C. for about 30 minutes as described above.

NAP Formula D

This example illustrates the preparation by admixing of a compositions including a 1:1 weight ratio of naproxen (NAP) and a carrier comprising 5 wt. % of a purified phospholipid (Lipoid LLC), 46.5 wt. % of a purified triglyceride (TG) (Spectrum Chemical Manufacturing Corporation) and 48.5 wt. % of oleic acid (Spectrum Chemical Manufacturing Corporation) designed NAP Formula D.

NAP Formula D was prepared by admixing 50 wt. % NAPprofen (NAP) into a carrier comprising 23.25 wt. % triglycerides derived from Soy bean oil, 24.25 wt. % oleic acid and 2.5 wt. % of purified phosphatidylcholine at a temperature of about 40° C. for about 30 minutes as described above.

Partitioning Study of NAP vs. NAP Formulas A-D

In this study, pure naproxen (NAP) partitioning between cyclohexane and water versus NAP partitioning between cyclohexane and water in NAP Formulas A-D was investigated at pH 1 and at pH 7 simulating gastric fluids and duodenum fluids. The study was conducted by adding either NAP, NAP Formulas A-D into a cyclohexane/water partitioning system and measuring the differential partitioning of NAP between the two phase as the value Log P.

Referring now to FIG. 17, it is clear that NAP partitions differently at pH 1 versus pH7. NAP has a Log P of 0.65 at pH 1 and a Log P of −2.06 at pH 7. The partitioning of NAP in NAP Formulas A-D between cyclohexane and water at pH 1 as measured by Log P is higher than the Log P value of NAP at pH 1. The partitioning of NAP in NAP Formulas A-D between cyclohexane and water at pH 7 as measured by Log P is also higher than the Log P value for NAP at pH 7. Thus, while NAP shows a substantial pH dependent release, the NAP Formulas A-D also showed the pH dependent release behavior.

Indomethacin

Preparation of INDO Formulas A-D

INDO Formula A

This example illustrates the preparation by admixing of a composition including a 1:1 weight ratio of indomethacin (INDO) and a carrier comprising about 40 wt. % of a purified phosphatidylcholine (PC) and a pure triglyceride (TG) designed INDO Formula A.

INDO Formula A was prepared by admixing 50 wt. % INDO into a carrier including 30 wt. % triglycerides derived from Soy bean oil from Spectrum OL103, lot 1AI0411 and 20 wt. % of purified phosphatidylcholine from Lipoid S 100, Charge 790569-10/0 at a temperature of about 40° C. for about 30 minutes as descried above.

INDO Formula B

This example illustrates the preparation by admixing of a composition including a 1:1 weight ratio of indomethacin (INDO) and a carrier comprising the lecithin oil Phosal 35SB (PS35SB) designed INDO Formula B.

INDO Formula B was prepared by admixing 50 wt. % INDO into a carrier comprising 50 wt. % PS35SB at a temperature of about 40° C. for about 30 minutes as described above.

INDO Formula C

This example illustrates the preparation by admixing of a compositions including a 1:1 weight ratio of indomethacin (INDO) and a carrier comprising 42 wt. % of a purified phospholipid, 28 wt. % of a purified triglyceride (TG) from Spectrum OL103, lot 1AI0411 and 30 wt. % of oleic acid designed INDO Formula C.

INDO Formula C was prepared by admixing 50 wt. % INDO into a carrier comprising 14 wt. % triglycerides derived from Soy bean oil, 15 wt. % oleic acid and 21 wt. % of purified phosphatidylcholine at a temperature of about 40° C. for about 30 minutes as described above.

INDO Formula D

This example illustrates the preparation by admixing of a compositions including a 1:1 weight ratio of indomethacin (INDO) and a carrier comprising 5 wt. % of a purified phospholipid, 46.5 wt. % of a purified triglyceride (TG) and 48.5 wt. % of oleic acid designed INDO Formula D.

INDO Formula D was prepared by admixing 50 wt. % INDO into a carrier comprising 23.25 wt. % triglycerides derived from Soy bean oil, 24.25 wt. % oleic acid and 2.5 wt. % of purified phosphatidylcholine at a temperature of about 40° C. for about 30 minutes as described above.

Partitioning Study of INDO vs. INDO Formulas A-D

In this study, pure indomethacin (INDO) partitioning between cyclohexane and water versus INDO partitioning between cyclohexane and water in INDO Formulas A-D was investigated at pH 1 and at pH 7 simulating gastric fluids and duodenum fluids. The study was conducted by adding either INDO, INDO Formulas A-D into a cyclohexane/water partitioning system and measuring the differential partitioning of INDO between the two phase as the value Log P.

Referring now to FIG. 18, it is clear that INDO partitions differently at pH 1 versus pH7. INDO has a Log P of 1.05 at pH 1 and a Log P of −1.81 at pH 7. The partitioning of INDO in INDO Formulas A-D between cyclohexane and water at pH 1 as measured by Log P is higher than the Log P value of NAP at pH 1. The partitioning of INDO in INDO Formulas A-D between cyclohexane and water at pH 7 as measured by Log P is also higher than the Log P value for INDO at pH 7. Thus, while INDO shows a substantial pH dependent release, the INDO Formulas A-D also showed the pH dependent release behavior.

Mefenamic Acid

Preparation of MFA Formulas A-D

MFA Formula A

This example illustrates the preparation by admixing of a composition including a 1:1 weight ratio of mefenamic acid (MFA) and a carrier comprising about 40 wt. % of a purified phosphatidylcholine (PC) and a pure triglyceride (TG) designed MFA Formula A.

MFA Formula A was prepared by admixing 50 wt. % MFA into a carrier including 30 wt. % triglycerides derived from Soy bean oil from Spectrum OL103, lot 1AI0411 and 20 wt. % of purified phosphatidylcholine from Lipoid S100, Charge 790569-10/019 at a temperature of about 40° C. for about 30 minutes as descried above.

MFA Formula B

This example illustrates the preparation by admixing of a composition including a 1:1 weight ratio of mefenamic acid (MFA) and a carrier comprising the lecithin oil Phosal 35SB (PS35SB) designed MFA Formula B.

MFA Formula B was prepared by admixing 50 wt. % MFA into a carrier comprising 50 wt. % PS35SB at a temperature of about 40° C. for about 30 minutes as described above.

MFA Formula C

This example illustrates the preparation by admixing of a compositions including a 1:1 weight ratio of mefenamic acid (MFA) and a carrier comprising 42 wt. % of a purified phospholipid, 28 wt. % of a purified triglyceride (TG) and 30 wt. % of oleic acid designed MFA Formula C.

MFA Formula C was prepared by admixing 50 wt. % MFA into a carrier comprising 14 wt. % triglycerides derived from Soy bean oil from Spectrum OL103, lot 1AI0411, 15 wt. % oleic acid and 21 wt. % of purified phosphatidylcholine at a temperature of about 40° C. for about 30 minutes as described above.

MFA Formula D

This example illustrates the preparation by admixing of a compositions including a 1:1 weight ratio of mefenamic acid (MFA) and a carrier comprising 5 wt. % of a purified phospholipid, 46.5 wt. % of a purified triglyceride (TG) and 48.5 wt. % of oleic acid designed MFA Formula D.

MFA Formula D was prepared by admixing 50 wt. % MFA into a carrier comprising 23.25 wt. % triglycerides derived from Soy bean oil, 24.25 wt. % oleic acid and 5 wt. % of purified phosphatidylcholine at a temperature of about 40° C. for about 30 minutes as described above.

Partitioning Study of MFA vs. MFA Formulas A-D

In this study, pure mefenamic acid (MFA) partitioning between cyclohexane and water versus MFA partitioning between cyclohexane and water in MFA Formulas A-D was investigated at pH 1 and at pH 7 simulating gastric fluids and duodenum fluids. The study was conducted by adding either MFA, MFA Formulas A-D into a cyclohexane/water partitioning system and measuring the differential partitioning of MFA between the two phase as the value Log P.

Referring now to FIG. 19, it is clear that MFA partitions differently at pH 1 versus pH7. MFA has a Log P of 0.00 at pH 1 and a Log P of 0.47 at pH 7. The partitioning of MFA in MFA Formulas A-D between cyclohexane and water at pH 1 as measured by Log P is significantly more positive than the Log P value of MFA at pH 1, showing little difference between the oil based carriers. The partitioning of MFA in MFA Formulas A-D between cyclohexane and water at pH 7 as measured by Log P only showed a slightly higher value than the Log P value for MFA at pH 7, except for MFA Formula A, which shows a slightly lower value than the Log P value for MFA at pH 7. Thus, while MFA shows a substantial pH dependent release, the MFA Formulas A-D also showed the pH dependent release behavior.

Summary of Weak Acid Partitioning Data

From the data presented above for aspirin, salicylic acid, naproxen, indomethacin, and mefenamic acid, it is clear the carriers including a sufficient amount of free fatty acid release these weak acids in a pH dependent manner so that the weak acid biologically active agents may be targeted to higher pH values as the agents leave the low pH environment of the stomach. As this targeted release of the active agents from the lipid matrix appears to be due to ionization state of the free fatty acid in the carrier relative to pH and other physiological milieu of selected regions of the GI tract. Thus, targeted release of any biologically active agent should be possible, and particularly useful for active ingredients that are a) injurious to the upper GI tract (stomach and duodenum), b) acid labile active, c) insoluble/impermeable compounds GI fluids and d) susceptible to first pass metabolism.

CLOSING

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. An orally administrable pharmaceutical composition comprising a solid, weak-acid NSAID and a carrier, wherein the carrier:
   (a) comprises at least 10 wt. % of free monocarboxylic acid having at least 8 carbons; and
   (b) wherein the carrier comprises from about 0.0001 wt. % to about 5 wt. % of zwitterionic phospholipids,
   wherein the composition release a lesser amount of NSAID at a pH <3 than at a pH >3, and wherein the pharmaceutical composition is a non-aqueous solid-in-oil suspension.

2. The pharmaceutical composition of claim 1, wherein the carrier further comprises a neutral lipid.

3. The pharmaceutical composition of claim 1, wherein the carrier comprises 0% to 0.05 wt. % phospholipids.

4. The pharmaceutical composition of claim 1, having a carrier-to-NSAID weight ratio of between 1:10 and 10:1.

5. The pharmaceutical composition of claim 3, wherein the carrier comprises one monocarboxylic acid or a plurality of monocarboxylic acids.

6. The pharmaceutical composition of claim 1, wherein the carrier comprises a mixture of different monocarboxylic acids having at least 8 carbons.

7. A pharmaceutical composition according to claim 1, that comprises up to 40 wt. % monocarboxylic acids.

8. The pharmaceutical composition of claim 7, wherein the monocarboxylic acids comprise oleic acid.

9. The pharmaceutical composition of claim 8, wherein the NSAID is selected from the group consisting of ibuprofen, piroxicam, salicylate, aspirin, naproxen, indomethacin, diclofenac, mefenamic acid, COX2 inhibitors or any mixture thereof.

10. The pharmaceutical composition of claim 9, wherein the NSAID is selected from the group consisting of aspirin, naproxen, indomethacin and mefenamic acid.

11. The pharmaceutical composition of claim 1, wherein <20% of the NSAID is released from the pharmaceutical composition in an environment of pH <3 and wherein >50% of the NSAID is released in an environment of pH >3.

12. The pharmaceutical composition of claim 1, wherein the NSAID is released at pH values of less than pH 2 at a rate of less than about 20% in thirty minutes, and wherein the NSAID is released, at pH values above about pH 3, at a rate of greater than 80% in thirty minutes.

13. The pharmaceutical composition of claim 1, further comprising a secondary complexing agent selected from the group consisting of an antioxidant, a preservative, a viscomodulator, a suspending agent, a drying agent, and mixtures thereof.

14. The pharmaceutical composition of claim 7, wherein the monocarboxylic acids comprise a mixture of oleic acid and linoleic acid.

15. The pharmaceutical composition of claim 1, wherein the amount of zwitterionic phospholipids is from about 0.5 wt. % up to about 2.5 wt. %.

16. The pharmaceutical composition of claim 1, wherein the amount of zwitterionic phospholipids is selected from the group consisting of about 0.5 wt. %, about 1 wt. %, about 2 wt. %, about 2.5 wt. %, and about 5 wt. %.

* * * * *